United States Patent
Korman et al.

(10) Patent No.: US 9,580,507 B2
(45) Date of Patent: *Feb. 28, 2017

(54) HUMAN MONOCLONAL ANTIBODIES TO PROGRAMMED DEATH LIGAND 1 (PD-L1)

(71) Applicant: E.R. Squibb & Sons, L. L. C., Princeton, NJ (US)

(72) Inventors: Alan J. Korman, Piedmont, CA (US); Mark J. Selby, San Francisco, CA (US); Changyu Wang, Union City, CA (US); Mohan Srinivasan, Cupertino, CA (US); David B. Passmore, San Carlos, CA (US); Haichun Huang, Fremont, CA (US); Haibin Chen, San Jose, CA (US)

(73) Assignee: E.R. Squibb & Sons, L. L. C., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/188,860

(22) Filed: Jun. 21, 2016

(65) Prior Publication Data

US 2016/0362495 A1    Dec. 15, 2016

Related U.S. Application Data

(62) Division of application No. 14/807,522, filed on Jul. 23, 2015, which is a division of application No. 13/746,773, filed on Jan. 22, 2013, now Pat. No. 9,102,725, which is a division of application No. 13/091,936, filed on Apr. 21, 2011, now Pat. No. 8,383,796, which is a division of application No. 11/917,727, filed as application No. PCT/US2006/026046 on Jun. 30, 2006, now Pat. No. 7,943,743.

(60) Provisional application No. 60/696,426, filed on Jul. 1, 2005.

(51) Int. Cl.
    C07K 16/28    (2006.01)
    A61K 39/395   (2006.01)
    A61K 45/06    (2006.01)
    A61K 39/00    (2006.01)

(52) U.S. Cl.
    CPC ...... *C07K 16/2827* (2013.01); *A61K 39/3955* (2013.01); *A61K 45/06* (2013.01); *A61K 2039/505* (2013.01); *C07K 2317/21* (2013.01); *C07K 2317/51* (2013.01); *C07K 2317/74* (2013.01); *C07K 2317/75* (2013.01); *C07K 2317/76* (2013.01); *C07K 2317/92* (2013.01)

(58) Field of Classification Search
    None
    See application file for complete search history.

(56) References Cited

U.S. PATENT DOCUMENTS

| | | |
|---|---|---|
| 5,324,514 A | 6/1994 | Sipos |
| 5,629,204 A | 5/1997 | Honjo et al. |
| 5,698,520 A | 12/1997 | Honjo et al. |
| 5,897,862 A | 4/1999 | Hardy et al. |
| 6,051,227 A | 4/2000 | Allison et al. |
| 6,300,064 B1 | 10/2001 | Knappik et al. |
| 6,632,927 B2 | 10/2003 | Adair et al. |
| 6,632,976 B1 | 10/2003 | Tomizuka et al. |
| 6,803,192 B1 | 10/2004 | Chen |
| 6,808,710 B1 | 10/2004 | Wood et al. |
| 6,881,557 B2 | 4/2005 | Foote |
| 6,936,704 B1 | 8/2005 | Freeman et al. |
| 6,965,018 B2 | 11/2005 | Mikesell et al. |
| 7,029,674 B2 | 4/2006 | Carreno et al. |
| 7,038,013 B2 | 5/2006 | Freeman et al. |
| 7,041,474 B2 | 5/2006 | Kingsbury et al. |
| 7,101,550 B2 | 9/2006 | Wood et al. |
| 7,105,328 B2 | 9/2006 | Wood et al. |
| 7,122,372 B2 | 10/2006 | Hardy et al. |
| 7,279,567 B2 | 10/2007 | Mikesell et al. |
| 7,358,354 B2 | 4/2008 | Mikesell et al. |
| 7,368,531 B2 | 5/2008 | Rosen et al. |
| 7,368,554 B2 | 5/2008 | Mikesell et al. |
| 7,385,036 B2 | 6/2008 | Kingsbury et al. |
| 7,396,917 B2 | 7/2008 | Bowdish et al. |
| 7,501,496 B1 | 3/2009 | Endl et al. |

(Continued)

FOREIGN PATENT DOCUMENTS

| | | |
|---|---|---|
| AU | 774391 B2 | 6/2004 |
| EP | 0670369 | 9/1995 |

(Continued)

OTHER PUBLICATIONS

Amendment after Notice of Allowance mailed Jan. 10, 2013, in U.S. Appl. No. 13/091,936, Alan, J., et al., filed Apr. 21, 2011.

Amendment and Request for Continued Examination (RCE) mailed Aug. 20, 2012, in U.S. Appl. No. 13/091,936, Alan, J., et al., filed Apr. 21, 2011.

Barbas, S.M., et al., "Human Autoantibody Recognition of DNA," Proceedings of the National Academy of Sciences of the United States of America 92(7):2529-2533, National Academy of Sciences, United States (1995).

Barbas, S.M., et al., "Recognition of DNA by Synthetic Antibodies," Journal of the American Chemical Society 116(5):2161-2162, American Chemical Society, United States (1994).

(Continued)

*Primary Examiner* — Ilia Ouspenski
(74) *Attorney, Agent, or Firm* — Sterne, Kessler, Goldstein & Fox P.L.L.C.

(57) ABSTRACT

The present disclosure provides isolated monoclonal antibodies, particularly human monoclonal antibodies that specifically bind to PD-L1 with high affinity. Nucleic acid molecules encoding the antibodies of this disclosure, expression vectors, host cells and methods for expressing the antibodies of this disclosure are also provided. Immunoconjugates, bispecific molecules and pharmaceutical compositions comprising the antibodies of the invention are also provided. The disclosure also provides methods for detecting PD-L1, as well as methods for treating various diseases, including cancer and infectious diseases, using anti-PD-L1 antibodies.

30 Claims, 61 Drawing Sheets

(56) References Cited

U.S. PATENT DOCUMENTS

| | | |
|---|---|---|
| 7,595,048 B2 | 9/2009 | Honjo et al. |
| 7,794,710 B2 | 9/2010 | Chen et al. |
| 7,943,743 B2 | 5/2011 | Korman et al. |
| 8,168,179 B2 | 5/2012 | Honjo et al. |
| 8,383,796 B2 | 2/2013 | Korman et al. |
| 9,102,725 B2 | 8/2015 | Korman et al. |
| 9,273,135 B2 | 3/2016 | Korman et al. |
| 9,358,289 B2 | 6/2016 | Kormna et al. |
| 9,393,301 B2 | 7/2016 | Honjo et al. |
| 9,402,899 B2 | 8/2016 | Honjo et al. |
| 9,439,962 B2 | 9/2016 | Honjo et al. |
| 2002/0102651 A1 | 8/2002 | Freeman et al. |
| 2002/0164600 A1 | 11/2002 | Freeman et al. |
| 2003/0031675 A1 | 2/2003 | Mikesell et al. |
| 2003/0039653 A1 | 2/2003 | Chen et al. |
| 2003/0232323 A1 | 12/2003 | Freeman et al. |
| 2004/0073957 A1 | 4/2004 | Tomizuka et al. |
| 2004/0175380 A1 | 9/2004 | Allison et al. |
| 2004/0241745 A1 | 12/2004 | Honjo et al. |
| 2005/0059051 A1 | 3/2005 | Chen |
| 2006/0083744 A1 | 4/2006 | Chen et al. |
| 2006/0110383 A1 | 5/2006 | Honjo et al. |
| 2006/0153841 A1 | 7/2006 | Freeman et al. |
| 2007/0092504 A1 | 4/2007 | Carreno et al. |
| 2007/0202100 A1 | 8/2007 | Wood et al. |
| 2008/0213778 A1 | 9/2008 | Holtzman et al. |
| 2009/0055944 A1 | 2/2009 | Korman et al. |
| 2009/0217401 A1 | 8/2009 | Korman et al. |
| 2009/0297518 A1 | 12/2009 | Honjo et al. |
| 2011/0209230 A1 | 8/2011 | Korman et al. |
| 2013/0122014 A1 | 5/2013 | Korman et al. |
| 2014/0314714 A1 | 10/2014 | Honjo et al. |
| 2015/0337038 A1 | 11/2015 | Korman et al. |
| 2016/0075782 A1 | 3/2016 | Korman et al. |
| 2016/0158355 A1 | 6/2016 | Honjo et al. |
| 2016/0158356 A1 | 6/2016 | Honjo et al. |

FOREIGN PATENT DOCUMENTS

| | | |
|---|---|---|
| EP | 0742795 | 9/1998 |
| EP | 1445264 | 8/2004 |
| EP | 1537878 A1 | 6/2005 |
| EP | 1591527 | 11/2005 |
| JP | 07291996 A | 11/1995 |
| JP | 2001527386 A | 12/2001 |
| JP | 2004512005 A | 4/2004 |
| WO | WO 97/07671 | 3/1997 |
| WO | WO 00/32231 | 6/2000 |
| WO | WO-0032752 A1 | 6/2000 |
| WO | WO 00/71078 | 11/2000 |
| WO | WO 01/14424 | 3/2001 |
| WO | WO-0114556 A1 | 3/2001 |
| WO | WO-0114557 A1 | 3/2001 |
| WO | WO-0134768 A2 | 5/2001 |
| WO | WO-0139722 A2 | 6/2001 |
| WO | WO 0183750 A2 | 11/2001 |
| WO | WO 0183750 A3 | 11/2001 |
| WO | WO 02/00692 | 1/2002 |
| WO | WO 02/00730 | 1/2002 |
| WO | WO 0232378 A2 | 4/2002 |
| WO | WO 0234205 A2 | 5/2002 |
| WO | WO 02/078731 | 10/2002 |
| WO | WO 02/079499 | 10/2002 |
| WO | WO-02086083 A2 | 10/2002 |
| WO | WO 03/006636 | 1/2003 |
| WO | WO-03008452 A2 | 1/2003 |
| WO | WO 03/011911 | 2/2003 |
| WO | WO 03/033644 | 4/2003 |
| WO | WO 03/042402 A2 | 5/2003 |
| WO | WO-03080672 A1 | 10/2003 |
| WO | WO 03/099196 | 12/2003 |
| WO | WO-2004004771 A1 | 1/2004 |
| WO | WO 2004/056875 | 7/2004 |
| WO | WO 2004/072286 | 8/2004 |
| WO | WO 2005/003298 A2 | 1/2005 |
| WO | WO 2006/021955 | 3/2006 |
| WO | WO-2006042237 A2 | 4/2006 |
| WO | WO 2006/121168 | 11/2006 |
| WO | WO 2006/124269 | 11/2006 |
| WO | WO-2007005874 A2 | 1/2007 |

OTHER PUBLICATIONS

Barber, D.L., et al., "Restoring Function in Exhausted CD8 T Cells during Chronic Viral Infection," Nature 439(7077):682-687, Nature Publishing Group, United States (2006).

Beiboer, S.H., et al., "Guided Selection of a Pan Carcinoma Specific Antibody Reveals Similar Binding Characteristics Yet Structural Divergence between the Original Murine Antibody and its Human Equivalent," Journal of Molecular Biology 296(3):833-849, Elsevier, England (2000).

Blank, C., et al., "PD-L1/B7H-1 Inhibits the Effector Phase of Tumor Rejection by T Cell Receptor (TCR) Transgenic CD8+ T Cells," Cancer Research 64(3):1140-1145, American Association for Cancer Research, United States (2004).

Brahmer, J.R., et al., "Safety and Activity of Anti-PD-L1 Antibody in Patients with Advanced Cancer," The New England Journal of Medicine 366(26):2455-2465, Massachusetts Medical Society, United States (2012).

Brown, J.A., et al., "Blockade of Programmed Death-1 Ligands on Dendritic Cells Enhances T Cell Activation and Cytokine Production," The Journal of Immunology 170(3):1257-1266, The American Association of Immunologists, United States (2003).

Certificate of Correction mailed Dec. 6, 2011, in U.S. Appl. No. 11/917,727, Alan, J., et al., filed Jun. 9, 2008.

Certificate of Correction mailed Jul. 9, 2013, in United States Patent Application No. 13/091,936, Alan, J, et al., filed Apr. 21, 2011.

Cox, J.P., et al., "A Directory of Human Germ-line V kappa Segments Reveals a Strong Bias in their Usage," European Journal of Immunology 24(4):827-836, Verlag Chemie GmbH, Germany (1994).

Dai, B., et al., "PD-1/PD-L1 Blockade can Enhance HIV-1 Gag-Specific T Cell Immunity Elicited by Dendritic Cell-Directed Lentiviral Vaccines," Molecular Therapy 20(9):1800-1809, Academic Press, United States (2012).

Final Office Action mailed Oct. 22, 2010, in U.S. Appl. No. 11/917,727, Alan, J., et al., filed Jun. 9, 2008.

International Preliminary Report on Patentability for International Application No. PCT/US2006/026046, International Bureau of WIPO, Switzerland, mailed on Jan. 9, 2008, 11 pages.

International Search Report and Written Opinion for International Application No. PCT/US2006/026046, European Patent Office, Netherlands, mailed on Apr. 3, 2007, 17 pages.

Ishida, I., et al., "TransChromo Mouse," Biotechnology & Genetic Engineering Reviews 19:73-82, Taylor & Francis, England (2002).

Issue Fee payment mailed Apr. 4, 2011, in U.S. Appl. No. 11/917,727, Alan, J., et al., filed Jun. 9, 2008.

Issue Fee payment mailed Jan. 22, 2013, in U.S. Appl. No. 13/091,936, Alan, J., et al., filed Apr. 21, 2011.

Kanai, T., et al., "Blockade of B7-H1 Suppresses the Development of Chronic Intestinal Inflammation," The Journal of Immunology 171(8):4156-4163, American Association of Immunologists, Inc., United States (2003).

Klimka, A., et al., "Human Anti-CD30 Recombinant Antibodies by Guided Phage Antibody Selection Using Cell Panning," British Journal of Cancer 83(2):252-260, Cancer Research Campaign, England (2000).

Koga, N., et al., "Blockade of the Interaction Between PD-1 and PD-L1 Accelerates Graft Arterial Disease in Cardiac Allografts," Arteriosclerosis, Thrombosis and Vascular Biology 24(11):2057-2062, American Heart Association, Inc., United States (2004).

Mukherjee, J., et al., "Human Stx2-Specific Monoclonal Antibodies Prevent Systemic Complications of Escherichia coli O157:H7 Infection," Infection and Immunity 70(2):612-619, American Society for Microbiology, United States (2002).

Non-Final Office Action mailed Jan. 31, 2012, in U.S. Appl. No. 13/091,936, Alan, J., et al., filed Apr. 21, 2011.

(56) References Cited

OTHER PUBLICATIONS

Non-Final Office Action mailed Jun. 8, 2010, in U.S. Appl. No. 11/917,727, Alan, J., et al., filed Jun. 9, 2008.
Notice of Allowance mailed Jan. 4, 2011, in U.S. Appl. No. 11/917,727, Alan, J., et al., filed Jun. 9, 2008.
Notice of Allowance mailed May 2, 2012, in U.S. Appl. No. 13/091,936, Alan, J., et al., filed Apr. 21, 2011.
Notice of Allowance mailed Oct. 23, 2012, in U.S. Appl. No. 13/091,936, Alan, J., et al., filed Apr. 21, 2011.
Panka, D.J., et al., "Variable Region Framework Differences Result in Decreased or Increased Affinity of Variant Anti-digoxin Antibodies," Proceedings of the National Academy of Sciences 85(9):3080-3084, National Academy of Sciences, United States (1988).
Porichis, F., et al., "Differential impact PD-1 and/or interleukin-10 blockade on HIV-1-specific CD4 T cell and antigen-presenting cell functions," Journal of Virology 88(5):2508-2518, American Society for Microbiology, United States (2014).
Rader, C., et al., "A Phage Display Approach for Rapid Antibody Humanization: Designed Combinatorial V Gene Libraries," Proceedings of the National Academy of Sciences of the United States of America 95(15):8910-8915, National Academy of Sciences, United States (1998).
Request for Certificate of Correction mailed Jun. 13, 2013, in U.S. Appl. No. 13/091,936, Alan, J., et al., filed Apr. 21, 2011.
Request for Certificate of Correction mailed Nov. 1, 2011, in U.S. Appl. No. 11/917,727, Alan, J., et al., filed Jun. 9, 2008.
Response to Amendment under Rule 312 mailed Jan. 18, 2013, in U.S. Appl. No. 13/091,936, Alan, J., et al., filed Apr. 21, 2011.
Response to Final Office Action mailed Dec. 21, 2010, in U.S. Appl. No. 11/917,727, Alan, J., et al., filed Jun. 9, 2008.
Response to Non-Final Office Action mailed Apr. 9, 2012, in U.S. Appl. No. 13/091,936, Alan, J., et al., filed Apr. 21, 2011.
Response to Non-Final Office Action mailed Sep. 8, 2010, in U.S. Appl. No. 11/917,727, Alan, J., et al., filed Jun. 9, 2008.
Response to Restriction Requirement mailed Mar. 15, 2010, in U.S. Appl. No. 11/917,727, Alan, J., et al., filed Jun. 9, 2008.
Restriction Requirement mailed Dec. 14, 2009, in U.S. Appl. No. 11/917,727, Alan, J., et al., filed Jun. 9, 2008.
Rudikoff, S., et al., "Single Amino Acid Substitution Altering Antigen-Binding Specificity," Proceedings of the National Academy of Sciences 79(6):1979-1983, The National Academy of Sciences, United States (1982).
Sakthivel, P., et al., "Therapeutic Intervention in Cancer and Chronic Viral Infections: Antibody Mediated Manipulation of PD-1/PD-L1 Interaction," Reviews on Recent Clinical Trials 7(1):10-23, Bentham Science Pub., United Arab Emirates (2012).
Seung, E., et al., "PD-1 Blockade in Chronically HIV-1-Infected Humanized Mice Suppresses Viral Loads," PloS One 8(10):e77780, Public Library of Science, United States(Oct. 2013).
Siewe, B., et al., "Regulatory B Cells Inhibit Cytotoxic T Lymphocyte (CTL) Activity and Elimination of Infected CD4 T Cells after In Vitro Reactivation of HIV Latent Reservoirs," PloS One 9(4):e92934, Public Library of Science, United States (Apr. 2014).
Tamura, M., et al., "Structural Correlates of an Anticarcinoma Antibody: Identification of Specificity-Determining Residues (SDRs) and Development of a Minimally Immunogenic Antibody Variant by Retention of SDRs only," Journal of Immunology 164(3):1432-1441, American Association of Immunologists, United States (2000).
Tomizuka, K., et al., "Double Trans-Chromosomic Mice: Maintenance of Two Individual Human Chromosome Fragments Containing Ig Heavy and Kappa loci and Expression of Fully Human Antibodies," Proceedings of the National Academy of Sciences of the United States of America 97(2):722-727, National Academy of Sciences, United States (2000).
Tomlinson, I.M., et al., "The Repertoire of Human Germline VH Sequences Reveals About Fifty Groups of VH segments with Different Hypervariable Loops," Journal of Molecular Biology 227(3):776-798, Elsevier, Netherlands (1992).

Xu, J.L. and Davis, M.M., "Diversity in the CDR3 Region of V(H) is Sufficient for Most Antibody Specificities," Immunity 13(1):37-45, Cell Press, United States (2000).
Blank, C., et al., "Blockade of PD-L1 (B7-H1) augments human tumor-specific T cell responses in vitro," International Journal of Cancer 119(2):317-327, International Union Against Cancer, United States (2006).
Iwai, Y., et al., "Involvement of PD-L1 on tumor cells in the escape from host immune system and tumor immunotherapy by PD-L1 blockade," Proceedings of the National Academy of Sciences of the United States of America 99(19):12293-12297, National Academy of Sciences, United States (2002).
Extended European Search Report and Search Opinion for EP Application No. 15172571.0, European Patent Office, Germany, mailed on Dec. 17, 2015.
Antonia, S.J., et al.,"Association of tumor PD-L1 Expression and Immune Biomarkers with Clinical Activity in Patients with Non-small Cell Lung Cancer (NSCLC) Treated with Nivolumab (Anti-PD-1; BMS-936558; ONO-4538)," 15th World Conference on Lung Cancer, Sydney, Australia, 15th WCLC: Best of Posters 1—IASLC Selection, P2.11-035, Oct. 27-30, 2013, accessed at http://web.oncoletter.ch/kongressberichte-videos-slides-Onkologie/id-15th-world-conference-on-lung-cancer-conference/conference-highlights.html, accessed on Jan. 8, 2015, 6 pages.
Blank, C., et al., "Interaction of PD-L1 on tumor cells with PD-1 on tumor-specific T cells as a mechanism of immune evasion: implications for tumor immunotherapy," Cancer Immunology, Immunotherapy 54:307-314, Springer Science+ Business Media, Germany (2005).
Brown, J.A., et al., "Expression and functional consequences of PD-1 ligands on natural APCS and tumors," The FASEB Journal 15(4):A345 (abstract No. 275.23), Federation of American Societies for Experimental Biology, United States (2001).
Brown, J.A., et al., "Blockade of PD-1 ligands on dendritic cells enhances T cells activation and cytokine production," FASEB Journal 16(4):710-517.4, Federation of American Societies for Experimental Biology, United States (2002).
Carreno, B.M., et al., "The B7 family of ligands and its receptors: New pathways for co-stimulation and inhibition of immune responses," Annu Rev. Immunol, 20:29-53, Annual reviews, United States (2002).
Carter, L., et al., "PD-1: PD-L inhibitory pathway affects both CD4+ and CDS+ T cells and is overcome by IL-2," Eur J Immunology 32:634-643, Wiley-VCH, Germany (2002).
Dong, H., et al., "Tumor-associated B7-H1 promotes T-cell apoptosis: A potential mechanism of immune evasion," Nat Med, 8:783-800, Nature, United States (2002).
Dong, H., Chen, L.,"B7-H1 pathway and its role in the evasion of tumor immunity," Journal of Molecular Medicine vol. 81:281-287, Springer Science+ Business Media, Germany (2002).
Dong, H., et al., "B7-H1, a third member of the B7 family, co-stimulates T-cell proliferation and interleukin-10 secretion," Nature Medicine 5(12):1365-1369, Nature America Inc., United States (1999).
Exhibit 1, "Dichotomy of the activity of PD-L1 (B7-4) and how an anti-PD-1 antibody fits into it," in Response to Patentee's Aug. 12, 2015 Reply, mailed Dec. 21, 2015 for European Patent No. EP 1537878, filed Jul. 2, 2003, 1 page.
Freeman, G.J., et al., "Engagement of the PD-1 immunoinhibitory receptor by a novel B7-family member leads to negative regulation of lymphocyte activation,",Journal of Experimental Medicine 192(7):1027-1034, Rockefeller University Press, United States (2000).
Freeman, G.J., et al., "Engagement of the PD-1 Immunoinhibitory by a Novel B7-Family Member Leads to Negative Regulation of Lymphocyte Activation," Blood 96(11):810a-811a (Abstract No. 3502) (2000).
He, Y.F., et al., "Blocking Programmed Death-1 Ligand-PD-1 Interactions by Local Gene Therapy Results in Enhancement of Antitumor Effect of Secondary Lymphoid Tissue Chemokine," Journal of Immunology 173: 4919-4928, American Association of Immunologist, United States (2004).

(56) References Cited

OTHER PUBLICATIONS

Hirano, F., et al., "Blockade of B7-H1 and PD-1 by monoclonal antibodies potentiates cancer therapeutic immunity," *Cancer Research* 65(3): 1089-1096, American Association for Cancer Research, United States (2005).

Konishi, J., et al., "B7-H1 Expression on Non-Small Cell Lung Cancer Cells and its Relationship with Tumor-Infiltrating Lymphocytes and Their PD-1 Expression," *Clin. Cancer Res 10*:5094-5100, American Association for Cancer Research, United States (2004).

Nagler, A., et al., "Phase I clinical trial of CT-011, a humanized monoclonal antibody directed against a B7 family-associated protein, in patients with advanced hematological malignancies," *Experimental Hematology*, 33:97, Elsevier, Netherlands (2005).

Nomi, T., et al., "Clinical significance and therapeutic potential of the programmed death-1 ligand/programmed death-1 pathway in human pancreatic cancer," *Clinical Cancer Research* 13(7):2151-2157, The Association, United States (2007).

Tamura, H., et al., "B7-H1 co-stimulation preferentially enhances CD28-independent T-helper cell function," *Blood 97(6)*:1809-1816, American Society of Hematology, United States (2001).

West, J.H., "CheckMate-057 Trial: The Future of PD-L1 as a Biomarker," medscape.com, accessed at http://www.medscape.com/viewarticle/845926, accessed on Sep. 17, 2015, 1 page (Jun. 5, 2015).

Yamazaki, T., et al., "Expression of programmed death 1 ligands by murine T cells and APC," *Journal of Immunology 169(10)*:5538-5545, American Association of Immunologist, United States (2002).

Zou, W. and Chen, L., "Inhibitory B7-family Molecules in the Tumour Microenvironment," *Nature Reviews Immunology 8(6)*:467-477, Nature Publishing Group, England (2008).

Zuberek, K., et al., "The role of in vivo PD-1/PD-L1 interactions in syngeneic and allogeneic antitumor responses in murine tumor models," *Blood 98(11)*: 42B, American Society of Hematology, United States (2001).

Liang, S.C., et al., "Regulation of PD-1, PD-L1, and PD-L2 expression during normal and autoimmunue responses," *Eur J Immunol* 33:2706-2716, Wiley-VCH Verlag GmbH & Co. KGaA, Germany (2003).

Schoop, R., et al., "Suppressed T-cell activation by IFN-γ-induced expression of PD-L1 on renal tubular epithelial cells," *Nephrol Dial Transplant* 19:2713-2720, Springer International, England (2004).

English Translation of Search Report dated Dec. 5, 2016, in Chinese Patent Application No. 201410639719.X.

Anti-PD-L1 3G10 VH

V segment:      1-18
    D segment:              undetermined
    J segment:      JH6b

```
           Q   V   Q   L   V   Q   S   G   A   E   V   K   K   P   G   A   S   V
  1       CAG GTT CAG CTG GTG CAG TCT GGA GCT GAG GTG AAG AAG CCT GGG GCC TCA GTG

CDR1
                                                       ~~~~~~~~~~~~~~~~~~~
           K   V   S   C   K   A   S   G   Y   T   F   T   D   Y   G   F   S   W
  55      AAG GTC TCC TGC AAG GCT TCT GGT TAC ACC TTT ACC GAC TAT GGT TTC AGC TGG

CDR2
                                                               ~~~~~~~~~~~~~~~~~~
           V   R   Q   A   P   G   Q   G   L   E   W   M   G   W   I   T   A   Y
 109      GTG CGA CAG GCC CCT GGA CAA GGG CTT GAG TGG ATG GGA TGG ATC ACC GCT TAC

CDR2
          ~~~~~~~~~~~~~~~~~~~~~~~~~~~~~~~~~~~~~~~~~~~~~~
           N   G   N   T   N   Y   A   Q   K   L   Q   G   R   V   T   M   T   T
 163      AAT GGT AAC ACA AAC TAT GCA CAG AAG CTC CAG GGC AGA GTC ACC ATG ACC ACA

D   T   S   T   S   T   V   Y   M   E   L   R   S   L   R   S   D   D
 217      GAC ACA TCC ACG AGC ACA GTC TAC ATG GAG CTG AGG AGC CTG AGA TCT GAC GAC

CDR3
                                          ~~~~~~~~~~~~~~~~~~~~~~~~~~~~~~~~~~~~
           T   A   V   Y   Y   C   A   R   D   Y   F   Y   G   M   D   V   W   G
 271      ACG GCC GTG TAT TAC TGT GCG AGA GAC TAC TTC TAC GGT ATG GAC GTC TGG GGC

Q   G   T   T   V   T   V   S   S
 325      CAA GGG ACC ACG GTC ACC GTC TCC TCA
```

Figure 1a

Anti-PD-L1 3G10 VK

V segment:    L6
J segment:    JK1

```
            E   I   V   L   T   Q   S   P   A   T   L   S   L   S   P   G   E   R
  1        GAA ATT GTG TTG ACA CAG TCT CCA GCC ACC CTG TCT TTG TCT CCA GGG GAA AGA

CDR1
                         ~~~~~~~~~~~~~~~~~~~~~~~~~~~~~~~~~~~~~~~~~~~~
            A   T   L   S   C   R   A   S   Q   S   V   S   S   Y   L   V   W   Y
 55        GCC ACC CTC TCC TGC AGG GCC AGT CAG AGT GTT AGC AGC TAC TTA GTC TGG TAC

CDR2
                                                        ~~~~~~~~~~~~~~~~~~~~~~~~~
            Q   Q   K   P   G   Q   A   P   R   L   L   I   Y   D   A   S   N   R
109        CAA CAG AAA CCT GGC CAG GCT CCC AGG CTC CTC ATC TAT GAT GCA TCC AAC AGG

CDR2
           ~~~~~~~
            A   T   G   I   P   A   R   F   S   G   S   G   S   G   T   D   F   T
163        GCC ACT GGC ATC CCA GCC AGG TTC AGT GGC AGT GGG TCT GGG ACA GAC TTC ACT

CDR3
                                                                            ~~~~~~~
            L   T   I   S   S   L   E   P   E   D   F   A   V   Y   Y   C   Q   Q
217        CTC ACC ATC AGC AGC CTA GAG CCT GAA GAT TTT GCA GTT TAT TAC TGT CAG CAG

CDR3
           ~~~~~~~~~~~~~~~~~~~~~~~~~
            R   S   N   W   P   R   T   F   G   Q   G   T   K   V   E   I   K
271        CGT AGC AAC TGG CCT CGG ACG TTC GGC CAA GGG ACC AAG GTG AAA ATC AAA
```

Figure 1b

Anti-PD-L1 12A4 VH

V segment:    1-69
    D segment:    3-10
    J segment:    JH6b

```
        Q   V   Q   L   V   Q   S   G   A   E   V   K   K   P   G   S   S   V
  1    CAG GTC CAG CTG GTG CAG TCT GGG GCT GAG GTG AAG AAG CCT GGG TCC TCG GTG

CDR1
                                                                  ~~~~~~~~~~~~~~~~~~
        K   V   S   C   K   T   S   G   D   T   F   S   T   Y   A   I   S   W
 55    AAG GTC TCC TGC AAG ACT TCT GGA GAC ACC TTC AGC ACC TAT GCT ATC AGC TGG

CDR2
                                                                  ~~~~~~~~~~~~~~~~~~
        V   R   Q   A   P   G   Q   G   L   E   W   M   G   G   I   I   P   I
109    GTG CGA CAG GCC CCT GGA CAA GGG CTT GAG TGG ATG GGA GGG ATC ATC CCT ATA

CDR2
       ~~~~~~~~~~~~~~~~~~~~~~~~~~~~~~~~~~~~~~~~~~~~~~
        F   G   K   A   H   Y   A   Q   K   F   Q   G   R   V   T   I   T   A
163    TTT GGT AAA GCA CAC TAC GCA CAG AAG TTC CAG GGC AGA GTC ACG ATT ACC GCG

D   E   S   T   S   T   A   Y   M   E   L   S   S   L   R   S   E   D
217    GAC GAA TCC ACG AGC ACA GCC TAC ATG GAG CTG AGC AGC CTG AGA TCT GAG GAC

CDR3
                                                          ~~~~~~~~~~~~~~~~~~~~~~~~~~~~~~~~~~~~~~~
        T   A   V   Y   F   C   A   R   K   F   H   F   V   S   G   S   P   F
271    ACG GCC GTG TAT TTT TGT GCG AGA AAG TTT CAC TTT GTT TCG GGA GCC CCC TTC

CDR3
       ~~~~~~~~~~~~~~~~
        G   M   D   V   W   G   Q   G   T   T   V   T   V   S   S
325    GGT ATG GAC GTC TGG GGC CAA GGG ACC ACG GTC ACC GTC TCC TCA
```

Figure 2a

Anti-PD-L1 12A4 VK

V segment:    L6
J segment:    JK1

```
          E   I   V   L   T   Q   S   P   A   T   L   S   L   S   P   G   E   R
    1    GAA ATT GTG TTG ACA CAG TCT CCA GCC ACC CTG TCT TTG TCT CCA GGG GAA AGA
                                              CDR1
                         ~~~~~~~~~~~~~~~~~~~~~~~~~~~~~~~~~~~~~~~~~
          A   T   L   S   C   R   A   S   Q   S   V   S   S   Y   L   A   W   Y
   55    GCC ACC CTC TCC TGC AGG GCC AGT CAG AGT GTT AGC AGC TAC TTA GCC TGG TAC
                                                                       CDR2
                                                           ~~~~~~~~~~~~~~~~~~~~~~
          Q   Q   K   P   G   Q   A   P   R   L   L   I   Y   D   A   S   N   R
  109    CAA CAG AAA CCT GGC CAG GCT CCC AGG CTC CTC ATC TAT GAT GCA TCC AAC AGG

CDR2
         ~~~~~~~
          A   T   G   I   P   A   R   F   S   G   S   G   S   G   T   D   F   T
  163    GCC ACT GGC ATC CCA GCC AGG TTC AGT GGC AGT GGG TCT GGG ACA GAC TTC ACT
                                                                           CDR3
                                                                           ~~~~~~~
          L   T   I   S   S   L   E   P   E   D   F   A   V   Y   Y   C   Q   Q
  217    CTC ACC ATC AGC AGC CTA GAG CCT GAA GAT TTT GCA GTT TAT TAC TGT CAG CAG

CDR3
         ~~~~~~~~~~~~~~~~~~~~~~~~
          R   S   N   W   P   T   F   G   Q   G   T   K   V   E   I   K
  271    CGT AGC AAC TGG CCG ACG TTC GGC CAA GGG ACC AAG GTG GAA ATC AAA
```

Figure 2b

```
Anti-PD-L1 10A5 VH

V segment:     1-3
    D segment:     5-5
    J segment:     JH4b

Q   V   Q   L   V   Q   S   G   A   E   V   K   K   P   G   A   S   V
  1 CAG GTC CAA CTT GTG CAG TCT GGG GCT GAG GTG AAG AAG CCT GGG GCC TCA GTG

CDR1
                                                    ~~~~~~~~~~~~~~~~~~~~
      K   V   S   C   K   A   S   G   Y   T   F   T   S   Y   D   V   H   W
 55 AAG GTT TCC TGC AAG GCT TCT GGA TAC ACC TTC ACT AGC TAT GAT GTA CAT TGG

CDR2
                                                    ~~~~~~~~~~~~~~~~~~~~
      V   R   Q   A   P   G   Q   R   L   E   W   M   G   W   L   H   A   D
109 GTG CGC CAG GCC CCC GGA CAA AGG CTT GAG TGG ATG GGA TGG CTC CAC GCT GAC

CDR2
    ~~~~~~~~~~~~~~~~~~~~~~~~~~~~~~~~~~~~~~~~~~~~
      T   G   I   T   K   F   S   Q   K   F   Q   G   R   V   T   I   T   R
163 ACT GGT ATC ACA AAA TTT TCA CAG AAG TTC CAG GGC AGA GTC ACC ATT ACC AGG

D   T   S   A   S   T   A   Y   M   E   L   S   S   L   R   S   E   D
217 GAC ACA TCC GCG AGC ACA GCC TAC ATG GAG CTG AGC AGC CTG AGA TCT GAA GAC

CDR3
                                        ~~~~~~~~~~~~~~~~~~~~~~~~~~~~~~~~~~~~
      T   A   V   Y   Y   C   A   R   E   R   I   Q   L   W   F   D   Y   W
271 ACG GCT GTG TAT TAC TGT GCG AGG GAG AGG ATA CAG CTA TGG TTT GAC TAC TGG

G   Q   G   T   L   V   T   V   S   S
325 GGC CAG GGA ACC CTG GTC ACC GTC TCC TCA
```

Figure 3a

Anti-PD-L1 10A5 VK

V segment:    L15
    J segment:    JK2

```
          D   I   Q   M   T   Q   S   P   S   S   L   S   A   S   V   G   D   R
      1   GAC ATC CAG ATG ACC CAG TCT CCA TCC TCA CTG TCT GCA TCT GTA GGA GAC AGA

CDR1
                                  ~~~~~~~~~~~~~~~~~~~~~~~~~~~~~~~~~~~~~~~~~~
          V   T   I   T   C   R   A   S   Q   G   I   S   S   W   L   A   W   Y
     55   GTC ACC ATC ACT TGT CGG GCG AGT CAG GGT ATT AGC AGC TGG TTA GCC TGG TAT

CDR2
                                                            ~~~~~~~~~~~~~~~~~~~~~
          Q   Q   K   P   E   K   A   P   K   S   L   I   Y   A   A   S   S   L
    109   CAG CAG AAA CCA GAG AAA GCC CCT AAG TCC CTG ATC TAT GCT GCA TCC AGT TTG

CDR2
          ~~~~~~~
          Q   S   G   V   P   S   R   F   S   G   S   G   S   G   T   D   F   T
    163   CAA AGT GGG GTC CCA TCA AGG TTC AGC GGC AGT GGA TCT GGG ACA GAT TTC ACT

CDR3
                                                                            ~~~~~~~
          L   T   I   S   S   L   Q   P   E   D   F   A   T   Y   Y   C   Q   Q
    217   CTC ACC ATC AGC AGC CTG CAG CCT GAA GAT TTT GCA ACT TAT TAC TGC CAA CAG

CDR3
          ~~~~~~~~~~~~~~~~~~~~~~~~~~~~
          Y   N   S   Y   P   Y   T   F   G   Q   G   T   K   L   E   I   K
    271   TAT AAT AGT TAC CCG TAC ACT TTT GGC CAG GGG ACC AAG CTG GAG ATC AAA
```

Figure 3b

Anti-PD-L1 5F8 VH

V segment:    1-69
    D segment:    6-13
    J segment:    JH4b

```
          Q   V   Q   L   V   Q   S   G   A   E   V   K   K   P   G   S   S   V
1         CAG GTC CAG CTG GTG CAG TCT GGG GCT GAG GTG AAG AAG CCT GGG TCC TCG GTG
                                                                CDR1
                                                                ~~~~~~~~~~~~~~~~~~
          K   V   S   C   K   V   S   G   G   I   F   S   T   Y   A   I   N   W
55        AAG GTC TCC TGC AAG GTT TCT GGA GGC ATC TTC AGC ACC TAT GCT ATC AAC TGG
                                                                       CDR2
                                                                       ~~~~~~~~~~~
          V   R   Q   A   P   G   Q   G   L   E   W   M   G   I   I   P   I
109       GTG CGA CAG GCC CCT GGA CAA GGG CTT GAG TGG ATG GGA GGG ATC ATC CCT ATC
                          CDR2
          ~~~~~~~~~~~~~~~~~~~~~~~~~~~~~~~~~~~~~~~~~~~~~~~~~~~~~
          F   G   T   A   N   H   A   Q   K   F   Q   G   R   V   T   I   T   A
163       TTT GGT ACA GCA AAC CAC GCA CAG AAG TTC CAG GGC AGA GTC ACG ATT ACC GCG

D   E   S   T   S   T   A   Y   M   E   L   S   S   L   R   S   E   D
217       GAC GAA TCC ACG AGC ACA GCC TAC ATG GAG CTG AGC AGC CTG AGA TCT GAG GAC
                                                                CDR3
                                                                ~~~~~~~~~~~~~~~~~~
          T   A   V   Y   Y   C   A   R   D   Q   G   I   A   A   A   L   F   D
271       ACG GCC GTG TAT TAC TGT GCG AGA GAT CAG GGT ATA GCA GCA GCC CTT TTT GAC
          CDR3
          ~~~~
          Y   W   G   Q   G   T   L   V   T   V   S   S
325       TAC TGG GGC CAG GGA ACC CTG GTC ACC GTC TCC TCA
```

Figure 4a

Anti-PD-L1 5F8 VK1

V segment:    A27
    J segment:    JK1

```
          E   I   V   L   T   Q   S   P   G   T   L   S   L   S   P   G   E   R
 1        GAA ATT GTG TTG ACG CAG TCT CCA GGC ACC CTG TCT TTG TCT CCA GGG GAA AGA
                                                CDR1
                              ~~~~~~~~~~~~~~~~~~~~~~~~~~~~~~~~~~~~~~~~~~~~~~~~~
          A   T   L   S   C   R   A   S   Q   S   V   S   S   S   Y   L   A   W
 55       GCC ACC CTC TCC TGC AGG GCC AGT CAG AGT GTT AGC AGC AGC TAC TTA GCC TGG
                                                                          CDR2
                                                                     ~~~~~~~~~~~~~~
          Y   Q   Q   K   P   G   Q   A   P   R   L   L   I   Y   G   A   S   S
 109      TAC CAG CAG AAA CCT GGC CAG GCT CCC AGG CTC CTC ATC TAT GGT GCA TCC AGC
          CDR2
          ~~~~~~~~~~~
          R   A   T   G   I   P   D   R   F   S   G   S   G   S   G   T   D   F
 163      AGG GCC ACT GGC ATC CCA GAC AGG TTC AGT GGC AGT GGG TCT GGG ACA GAC TTC

CDR3
                                                                                  ~~~
          T   L   T   I   S   R   L   E   P   E   D   F   A   V   Y   Y   C   Q
 217      ACT CTC ACC ATC AGC AGA CTG GAG CCT GAA GAT TTT GCA GTG TAT TAC TGT CAG
                CDR3
          ~~~~~~~~~~~~~~~~~~~~~~~~~~~~~~~~~~~~~
          Q   Y   G   S   S   P   W   T   F   G   Q   G   T   K   V   E   I   K
 271      CAG TAT GGT AGC TCA CCG TGG ACG TTC GGC CAA GGG ACC AAG GTG GAA ATC AAA
```

Figure 4b

Anti-PD-L1 10H10 VH

V segment:   3-9
  D segment:   4-17
  J segment:   JH4b

|     |   E   |   V   |   Q   |   L   |   V   |   E   |   S   |   G   |   G   |   G   |   L   |   V   |   Q   |   P   |   G   |   R   |   S   |   L   |
|-----|-------|-------|-------|-------|-------|-------|-------|-------|-------|-------|-------|-------|-------|-------|-------|-------|-------|-------|
| 1   | GAA   | GTG   | CAG   | CTG   | GTG   | GAG   | TCT   | GGG   | GGA   | GGC   | TTG   | GTA   | CAG   | CCT   | GGC   | AGG   | TCC   | CTG   |

CDR1

|     |   R   |   L   |   S   |   C   |   A   |   V   |   S   |   G   |   F   |   T   |   F   |   D   |   D   |   Y   |   V   |   V   |   H   |   W   |
|-----|-------|-------|-------|-------|-------|-------|-------|-------|-------|-------|-------|-------|-------|-------|-------|-------|-------|-------|
| 55  | AGA   | CTC   | TCC   | TGT   | GCA   | GTC   | TCT   | GGA   | TTC   | ACC   | TTT   | GAT   | GAT   | TAT   | GTC   | GTG   | CAC   | TGG   |

CDR2

|     |   V   |   R   |   Q   |   A   |   P   |   G   |   K   |   G   |   L   |   E   |   W   |   V   |   S   |   G   |   I   |   S   |   G   |   N   |
|-----|-------|-------|-------|-------|-------|-------|-------|-------|-------|-------|-------|-------|-------|-------|-------|-------|-------|-------|
| 109 | GTC   | CGG   | CAA   | GCT   | CCA   | GGG   | AAG   | GGC   | CTG   | GAG   | TGG   | GTC   | TCA   | GGT   | ATT   | AGT   | GGG   | AAT   |

CDR2

|     |   S   |   G   |   N   |   I   |   G   |   Y   |   A   |   D   |   S   |   V   |   K   |   G   |   R   |   F   |   T   |   I   |   S   |   R   |
|-----|-------|-------|-------|-------|-------|-------|-------|-------|-------|-------|-------|-------|-------|-------|-------|-------|-------|-------|
| 163 | AGT   | GGT   | AAC   | ATA   | GGC   | TAT   | GCG   | GAC   | TCT   | GTG   | AAG   | GGC   | CGA   | TTC   | ACC   | ATC   | TCC   | AGA   |

|     |   D   |   N   |   A   |   K   |   N   |   S   |   L   |   Y   |   L   |   Q   |   M   |   N   |   S   |   L   |   R   |   A   |   E   |   D   |
|-----|-------|-------|-------|-------|-------|-------|-------|-------|-------|-------|-------|-------|-------|-------|-------|-------|-------|-------|
| 217 | GAC   | AAC   | GCC   | AAG   | AAC   | TCC   | CTG   | TAT   | CTG   | CAA   | ATG   | AAC   | AGT   | CTG   | AGA   | GCT   | GAG   | GAC   |

CDR3

|     |   T   |   A   |   L   |   Y   |   Y   |   C   |   A   |   V   |   P   |   F   |   D   |   Y   |   W   |   G   |   Q   |   G   |   T   |   L   |
|-----|-------|-------|-------|-------|-------|-------|-------|-------|-------|-------|-------|-------|-------|-------|-------|-------|-------|-------|
| 271 | ACG   | GCC   | TTG   | TAT   | TAC   | TGT   | GCG   | GTC   | CCC   | TTT   | GAC   | TAC   | TGG   | GGC   | CAG   | GGA   | ACC   | CTG   |

|     |   V   |   T   |   V   |   S   |   S   |
|-----|-------|-------|-------|-------|-------|
| 325 | GTC   | ACC   | GTC   | TCC   | TCA   |

Figure 5a

Anti-PD-L1 10H10 VK

V segment:       L15
    J segment:       JK2

```
              D   I   Q   M   T   Q   S   P   S   S   L   S   A   S   V   G   D   R
1             GAC ATC CAG ATG ACC CAG TCT CCA TCC TCA CTG TCT GCA TCT GTA GGA GAC AGA
                                                        CDR1
                                              ~~~~~~~~~~~~~~~~~~~~~~~~~~~~~~~~~~~~
              V   T   I   T   C   R   A   S   Q   G   I   S   S   W   L   A   W   Y
55            GTC ACC ATC ACT TGT CGG GCG AGT CAG GGT ATT AGC AGC TGG TTA GCC TGG TAT
                                                                            CDR2
                                                                  ~~~~~~~~~~~~~~~~~~
              Q   Q   K   P   E   K   A   P   K   S   L   I   Y   A   A   S   S   L
109           CAG CAG AAA CCA GAG AAA GCC CCT AAG TCC CTG ATC TAT GCT GCA TCC AGT TTG
              CDR2
              ~~~~~~~
              Q   S   G   V   P   S   R   F   S   G   S   G   S   G   T   D   F   T
163           CAA AGT GGG GTC CCA TCA AGG TTC AGC GGC AGT GGA TCT GGG ACA GAT TTC ACT
                                                                                CDR3
                                                                                ~~~~~~~
              L   T   I   S   S   L   Q   P   E   D   F   A   T   Y   Y   C   Q   Q
217           CTC ACC ATC AGC AGC CTG CAG CCT GAA GAT TTT GCA ACT TAT TAC TGC CAA CAG
                   CDR3
              ~~~~~~~~~~~~~~~~~~~~~~~~~~~~~~~
              Y   N   S   Y   P   Y   T   F   G   Q   G   T   K   L   E   I   K
271           TAT AAT AGT TAC CCG TAC ACT TTT GGC CAG GGG ACC AAG CTG GAG ATC AAA
```

Figure 5b

Anti-PD-L1 1B12 VH

V segment:      1-69
    D segment:              3-10
    J segment:      JH6b

```
         Q   V   Q   L   V   Q   S   G   A   E   V   K   K   P   G   S   S   V
1        CAG GTC CAG CTG GTG CAG TCT GGG GCT GAG GTG AAG AAG CCT GGG TCC TCG GTG

CDR1
                                                      ~~~~~~~~~~~~~~~~~~~~
         K   V   S   C   K   T   S   G   D   T   F   S   S   Y   A   I   S   W
55       AAG GTC TCC TGC AAG ACT TCT GGA GAC ACC TTC AGC AGC TAT GCT ATC AGC TGG

CDR2
                                                              ~~~~~~~~~~~~~~~~~~~~
         V   R   Q   A   P   G   Q   G   L   E   W   M   G   G   I   I   P   I
109      GTG CGA CAG GCC CCT GGA CAA GGG CTT GAG TGG ATG GGA GGG ATC ATC CCT ATC

CDR2
         ~~~~~~~~~~~~~~~~~~~~~~~~~~~~~~~~~~~~~~~~~~~~~~~~~~
         F   G   R   A   H   Y   A   Q   K   F   Q   G   R   V   T   I   T   A
163      TTT GGT AGA GCA CAC TAC GCA CAG AAG TTC CAG GGC AGA GTC ACG ATT ACC GCG

D   E   S   T   S   T   A   Y   M   E   L   S   S   L   R   S   E   D
217      GAC GAA TCC ACG AGC ACA GCC TAC ATG GAG CTG AGC AGC CTG AGA TCT GAG GAC

CDR3
                                                      ~~~~~~~~~~~~~~~~~~~~~~~~~~~~~~~~
         T   A   V   Y   F   C   A   R   K   F   H   F   V   S   G   P   F
271      ACG GCC GTG TAT TTT TGT GCG AGA AAG TTT CAC TTT GTT TCG GGG AGC CCC TTC

CDR3
         ~~~~~~~~~~~~~~~~~
         G   M   D   V   W   G   Q   G   T   T   V   T   V   S   S
325      GGT ATG GAC GTC TGG GGC CAA GGG ACC ACG GTC ACC GTC TCC TCA
```

Figure 6a

Anti-PD-L1 1B12 VK

V segment:     L6
J segment:     JK1

```
        E   I   V   L   T   Q   S   P   A   T   L   S   L   S   P   G   E   R
1       GAA ATT GTG TTG ACA CAG TCT CCA GCC ACC CTG TCT TTG TCT CCA GGG GAA AGA
                                              CDR1
                                        ~~~~~~~~~~~~~~~~~~~~~~~~~~~~~~~~~~~~~~
        A   T   L   S   C   R   A   S   Q   S   V   S   S   Y   L   A   W   Y
55      GCC ACC CTC TCC TGC AGG GCC AGT CAG AGT GTT AGC AGC TAC TTA GCC TGG TAC
                                                                      CDR2
                                                                ~~~~~~~~~~~~~~~~~~
        Q   Q   K   P   G   Q   A   P   R   L   L   I   Y   D   A   S   N   R
109     CAA CAG AAA CCT GGC CAG GCT CCC AGG CTC CTC ATC TAT GAT GCA TCC AAC AGG

CDR2
        ~~~~~~~
        A   T   G   I   P   A   R   F   S   G   S   G   S   T   D   F   T
163     GCC ACT GGC ATC CCA GCC AGG TTC AGT GGC AGT GGG TCT GGG ACA GAC TTC ACT
                                                                          CDR3
                                                                        ~~~~~~~
        L   T   I   S   S   L   E   P   E   D   F   A   V   Y   Y   C   Q   Q
217     CTC ACC ATC AGC AGC CTA GAG CCT GAA GAT TTT GCA GTT TAT TAC TGT CAG CAG

CDR3
        ~~~~~~~~~~~~~~~~~~~~~~~~
        R   S   N   W   P   T   F   G   Q   G   T   K   V   E   I   K
271     CGT AGC AAC TGG CCG ACG TTC GGC CAA GGG ACC AAG GTG GAA ATC AAA
```

Figure 6b

Anti-PD-L1 7H1 VH

V segment:    1-69
    D segment:      3-10
    J segment:    JH6b

```
              Q   V   Q   L   V   Q   S   G   A   E   V   K   K   P   G   S   S   V
1            CAG GTC CAG CTG GTG CAG TCT GGG GCT GAG GTG AAG AAG CCT GGG TCC TCG GTG
                                                                         CDR1
                                                                         ~~~~~~~~~~~~~~~~~
              K   V   S   C   K   T   S   G   G   T   F   S   S   Y   A   I   S   W
55           AAG GTC TCC TGC AAG ACT TCT GGA GGC ACC TTC AGC AGC TAT GCT ATC AGC TGG
                                                                    CDR2
                                                                    ~~~~~~~~~~~~~~~~~~
              V   R   Q   A   P   G   Q   G   L   E   W   M   G   G   I   I   P   I
109          GTG CGA CAG GCC CCT GGA CAA GGG CTT GAG TGG ATG GGA GGG ATC ATC CCT ATC
                              CDR2
             ~~~~~~~~~~~~~~~~~~~~~~~~~~~~~~~~~~~~~~~~~~~~~~~~~~~~
              F   G   K   A   H   Y   A   Q   K   F   Q   G   R   V   T   I   T   A
163          TTT GGT AAA GCA CAC TAC GCA CAG AAG TTC CAG GGC AGA GTC ACG ATT ACC GCG

D   E   S   T   T   T   A   Y   M   E   L   S   S   L   R   S   E   D
217          GAC GAA TCC ACG ACC ACA GCC TAC ATG GAG CTG AGC AGC CTG AGA TCT GAG GAC
                                                                    CDR3
                                                                    ~~~~~~~~~~~~~~~~~~~~~~~
              T   A   V   Y   Y   C   A   R   K   Y   D   Y   V   S   G   S   P   F
271          ACG GCC GTG TAT TAC TGT GCG AGA AAG TAT GAC TAT GTT TCG GGG AGC CCC TTC
                 CDR3
             ~~~~~~~~~~~~~~~~~
              G   M   D   V   W   G   Q   G   T   T   V   T   V   S   S
325          GGT ATG GAC GTC TGG GGC CAA GGG ACC ACG GTC ACC GTC TCC TCA
```

Figure 7a

Anti-PD-L1 7H1 VK

V segment:    L6
    J segment:    JK1

```
         E   I   V   L   T   Q   S   P   A   T   L   S   L   S   P   G   E   R
  1     GAA ATT GTG TTG ACA CAG TCT CCA GCC ACC CTG TCT TTG TCT CCA GGG GAA AGA

CDR1
                             ~~~~~~~~~~~~~~~~~~~~~~~~~~~~~~~~~~~~~~~~~~
         A   T   L   S   C   R   A   S   Q   S   V   S   S   Y   L   A   W   Y
  55    GCC ACC CTC TCC TGC AGG GCC AGT CAG AGT GTT AGC AGC TAC TTA GCC TGG TAC

CDR2
                                                        ~~~~~~~~~~~~~~~~~~~~~~~
         Q   Q   K   P   G   Q   A   P   R   L   L   I   Y   D   A   S   N   R
  109   CAA CAG AAA CCT GGC CAG GCT CCC AGG CTC CTC ATC TAT GAT GCA TCC AAC AGG

CDR2
        ~~~~~~~~
         A   T   G   I   P   A   R   F   S   G   S   G   S   G   T   D   F   T
  163   GCC ACT GGC ATC CCA GCC AGG TTC AGT GGC AGT GGG TCT GGG ACA GAC TTC ACT

CDR3
                                                                        ~~~~~~~
         L   T   I   S   S   L   E   P   E   D   F   A   V   Y   Y   C   Q   Q
  217   CTC ACC ATC AGC AGC CTA GAG CCT GAA GAT TTT GCA GTT TAT TAC TGT CAG CAG

CDR3
        ~~~~~~~~~~~~~~~~~~
         R   S   N   W   P   T   F   G   Q   G   T   K   V   E   I   K
  271   CGT AGC AAC TGG CCG ACG TTC GGC CAA GGG ACC AAG GTG GAA ATC AAA
```

Figure 7b

Anti-PD-L1 11E6 VH

V segment:    1-69
    D segment:    6-19
    J segment:    JH6c

```
              Q   V   Q   L   V   Q   S   G   A   E   V   K   K   P   G   S   S   V
1             CAG GTC CAG CTG GTG CAG TCT GGG GCT GAG GTG AAG AAG CCT GGG TCC TCG GTG
                                                                          CDR1
                                                                          ~~~~~~~~~~~~~~~~~~
              K   V   S   C   K   A   S   G   G   T   F   S   S   Y   A   I   N   W
55            AAG GTC TCC TGC AAG GCT TCT GGA GGC ACC TTC AGC AGC TAT GCT ATC AAC TGG
                                                                          CDR2
                                                                          ~~~~~~~~~~~~~~~~~~
              V   R   Q   A   P   G   Q   G   L   E   W   M   G   G   I   I   P   I
109           GTG CGA CAG GCC CCT GGA CAA GGG CTT GAG TGG ATG GGA GGG ATC ATC CCT ATC
                              CDR2
              ~~~~~~~~~~~~~~~~~~~~~~~~~~~~~~~~~~~~~~~~~~~~~~~~~~~~~~~~
              F   G   S   A   N   Y   A   Q   K   F   Q   D   R   V   T   I   T   A
163           TTT GGT TCA GCA AAC TAC GCA CAG AAG TTC CAG GAC AGA GTC ACG ATT ACC GCG

D   E   S   T   S   A   A   Y   M   E   L   S   S   L   R   S   E   D
217           GAC GAA TCC ACG AGC GCA GCC TAC ATG GAG CTG AGC AGC CTG AGA TCT GAG GAC
                                                                          CDR3
                                                                          ~~~~~~~~~~~~~~~~~~~~~~~~~~~~~~~~~~~~
              T   A   V   Y   Y   C   A   R   D   S   S   G   W   S   R   Y   Y   M
271           ACG GCC GTA TAT TAC TGT GCG AGA GAC AGC AGT GGC TGG TCT CGG TAC TAT ATG
              CDR3
              ~~~~~~~
              D   V   W   G   Q   G   T   T   V   T   V   S   S
325           GAC GTC TGG GGC CAA GGG ACC ACG GTC ACC GTC TCC TCA
```

Figure 8a

Anti-PD-L1 11E6 VK1

V segment:    A27
J segment:    JK4

```
           E   I   V   L   T   Q   S   P   G   T   L   S   L   S   P   G   E   R
  1       GAA ATT GTG TTG ACG CAG TCT CCA GGC ACC CTG TCT TTG TCT CCA GGG GAA AGA
                                                    CDR1
                                          ~~~~~~~~~~~~~~~~~~~~~~~~~~~~~~~~~~~~~~~~
           A   T   L   S   C   R   A   S   Q   S   V   S   S   S   Y   L   A   W
 55       GCC ACC CTC TCC TGC AGG GCC AGT CAG AGT GTT AGC AGC AGC TAC TTA GCC TGG
                                                                        CDR2
                                                                 ~~~~~~~~~~~~~~~~~
           Y   Q   Q   K   P   G   Q   A   P   R   L   L   I   Y   G   A   S   S
109       TAC CAG CAG AAA CCT GGC CAG GCT CCC AGG CTC CTC ATC TAT GGT GCA TCC AGC

CDR2
          ~~~~~~~~~~~
           R   A   T   G   I   P   D   R   F   S   G   S   G   S   G   T   D   F
163       AGG GCC ACT GGC ATC CCA GAC AGG TTC AGT GGC AGT GGG TCT GGG ACA GAC TTC
                                                                                CDR3
                                                                                ~~~
           T   L   T   I   S   R   L   E   P   E   D   F   A   V   Y   Y   C   Q
217       ACT CTC ACC ATC AGC AGA CTG GAG CCT GAA GAT TTT GCA GTG TAT TAC TGT CAG
                    CDR3
          ~~~~~~~~~~~~~~~~~~~~~~~
           Q   Y   G   S   S   P   F   G   G   G   T   K   V   E   I   K
271       CAG TAT GGT AGC TCA CCT TTC GGC GGA GGG ACC AAG GTG GAG ATC AAA
```

Figure 8b

Anti-PD-L1 12B7 VH

V segment:    1-69
    D segment:        3-10
    J segment:    JH6b

```
         Q    V    Q    L    V    Q    S    G    A    E    V    K    E    P    G    S    S    V
1        CAG  GTC  CAG  CTG  GTG  CAG  TCT  GGG  GCT  GAG  GTG  AAG  GAG  CCT  GGG  TCC  TCG  GTG

CDR1
                                                                      ~~~~~~~~~~~~~~~~~~
         K    V    S    C    K    A    S    G    T    F    N    S    Y    A    I    S    W
55       AAG  GTC  TCC  TGC  AAG  GCT  TCT  GGA  GGC  ACC  TTC  AAC  AGC  TAT  GCT  ATC  AGC  TGG

CDR2
                                                                      ~~~~~~~~~~~~~~~~~~
         V    R    Q    A    P    G    Q    G    L    E    W    M    G    G    I    I    P    L
109      GTG  CGA  CAG  GCC  CCT  GGA  CAA  GGG  CTT  GAG  TGG  ATG  GGA  GGG  ATC  ATC  CCT  CTT

CDR2
         ~~~~~~~~~~~~~~~~~~~~~~~~~~~~~~~~~~~~~~~~~~~~~~~~~~
         F    G    I    A    H    Y    A    Q    K    F    Q    G    R    V    T    I    T    A
163      TTC  GGT  ATA  GCA  CAC  TAC  GCA  CAG  AAG  TTC  CAG  GGC  AGA  GTC  ACG  ATT  ACC  GCG

D    E    S    T    N    T    A    Y    M    D    L    S    S    L    R    S    E    D
217      GAC  GAA  TCC  ACG  AAC  ACA  GCC  TAT  ATG  GAC  CTG  AGC  AGC  CTG  AGA  TCT  GAG  GAC

CDR3
                                                                      ~~~~~~~~~~~~~~~~~~~~~~~~~~~~~~~
         T    A    V    Y    Y    C    A    R    K    Y    S    Y    V    S    G    S    P    F
271      ACG  GCC  GTA  TAT  TAT  TGT  GCG  AGA  AAG  TAT  TCC  TAT  GTT  TCG  GGG  AGC  CCC  TTC

CDR3
         ~~~~~~~~~~~~~~~~~~
         G    M    D    V    W    G    Q    G    T    T    V    T    V    S    S
325      GGT  ATG  GAC  GTC  TGG  GGC  CAA  GGG  ACC  ACG  GTC  ACC  GTC  TCC  TCA
```

Figure 9a

Anti-PD-L1 12B7 VK

V segment:    L6
J segment:    JK5

```
           E   I   V   L   T   Q   S   P   A   T   L   S   L   S   P   G   E   R
  1        GAA ATT GTG TTG ACA CAG TCT CCA GCC ACC CTG TCT TTG TCT CCA GGG GAA AGA
                                                    CDR1
                                       ~~~~~~~~~~~~~~~~~~~~~~~~~~~~~~~~~~~~~~~~~
           A   T   L   S   C   R   A   S   Q   S   V   S   S   Y   L   A   W   Y
 55        GCC ACC CTC TCC TGC AGG GCC AGT CAG AGT GTT AGC AGC TAC TTA GCC TGG TAC
                                                                        CDR2
                                                                ~~~~~~~~~~~~~~~~~
           Q   Q   K   P   G   Q   A   P   R   L   L   I   Y   D   A   S   N   R
109        CAA CAG AAA CCT GGC CAG GCT CCC AGG CTC CTC ATC TAT GAT GCA TCC AAC AGG

CDR2
           ~~~~~~~
           A   T   G   I   P   A   R   F   S   G   S   G   S   G   T   D   F   T
163        GCC ACT GGC ATC CCA GCC AGG TTC AGT GGC AGT GGG TCT GGG ACA GAC TTC ACT
                                                                            CDR3
                                                                        ~~~~~~~~~
           L   T   I   S   S   L   E   P   E   D   F   A   V   Y   Y   C   Q   Q
217        CTC ACC ATC AGC AGC CTA GAG CCT GAA GAT TTT GCA GTT TAT TAC TGT CAG CAG

CDR3
           ~~~~~~~~~~~~~~~~~~~~
           R   S   N   W   P   T   F   G   Q   G   T   R   L   E   I   K
271        CGT AGC AAC TGG CCC ACC TTC GGC CAA GGG ACA CGA CTG GAG ATT AAA
```

Figure 9b

Anti-PD-L1 13G4 VH

V segment:       3-9
    D segment:       3-9
    J segment:       JH4b

```
           E   V   Q   L   V   E   S   G   G   G   L   V   Q   P   G   R   S   L
1          GAA GTG CAG TTG GTG GAG TCT GGG GGA GGC TTG GTA CAG CCT GGC AGG TCC CTG

CDR1
                                                                       ~~~~~~~~~~~~~~~~~~
           R   L   S   C   A   A   S   G   I   T   F   D   D   Y   G   M   H   W
55         AGA CTC TCC TGT GCA GCC TCT GGA ATC ACC TTT GAT GAT TAT GGC ATG CAC TGG

CDR2
                                                                       ~~~~~~~~~~~~~~~~~~
           V   R   Q   A   P   G   K   G   L   E   W   V   S   G   I   S   W   N
109        GTC CGG CAA GCT CCA GGG AAG GGC CTG GAG TGG GTC TCA GGT ATT AGC TGG AAT

CDR2
           ~~~~~~~~~~~~~~~~~~~~~~~~~~~~~~~~~~~~~~~~~~~~~~~~~~
           R   G   R   I   E   Y   A   D   S   V   K   G   R   F   T   I   S   R
163        AGA GGT AGA ATA GAG TAT GCG GAC TCT GTG AAG GGC CGA TTC ACC ATC TCC AGA

D   N   A   K   N   S   L   Y   L   Q   M   N   S   L   R   A   E   D
217        GAC AAC GCC AAG AAC TCC CTG TAT CTG CAA ATG AAC AGT CTG AGA GCT GAG GAC

CDR3
                                                           ~~~~~~~~~~~~~~~~~~~~~~~~~~~~~~
           T   A   L   Y   Y   C   A   K   G   R   F   R   Y   F   D   W   F   L
271        ACG GCC TTG TAT TAC TGT GCA AAA GGG CGG TTC CGA TAT TTT GAC TGG TTT CTT

CDR3
           ~~~~~~~
           D   Y   W   G   Q   G   T   L   V   T   V   S   S
325        GAC TAC TGG GGC CAG GGA ACC CTG GTC ACC GTC TCC TCA
```

Figure 10a

Anti-PD-L1 13G4 VK

V segment:  L18
J segment:  JK3

```
          A   I   Q   L   T   Q   S   P   S   S   L   S   A   S   V   G   D   R
1         GCC ATC CAG TTG ACC CAG TCT CCA TCC TCC CTG TCT GCA TCT GTA GGA GAC AGA
                                              CDR1
                              ~~~~~~~~~~~~~~~~~~~~~~~~~~~~~~~~~~~~~~~~~~~~
          V   T   I   T   C   R   A   S   Q   G   I   S   S   A   L   A   W   Y
55        GTC ACC ATC ACT TGC CGG GCA AGT CAG GGC ATT AGC AGT GCT TTA GCC TGG TAT
                                                                       CDR2
                                                              ~~~~~~~~~~~~~~~~~~~~
          Q   Q   K   P   G   K   A   P   K   L   L   I   Y   D   A   S   S   L
109       CAG CAG AAA CCA GGG AAA GCT CCT AAG CTC CTG ATC TAT GAT GCC TCC AGT TTG
          CDR2
          ~~~~~~~~
          E   S   G   V   P   S   R   F   S   G   S   G   S   G   T   D   F   T
163       GAA AGT GGG GTC CCA TCA AGG TTC AGC GGC AGT GGA TCT GGG ACA GAT TTC ACT
                                                                              CDR3
                                                                           ~~~~~~~~
          L   T   I   S   S   L   Q   P   E   D   F   A   T   Y   Y   C   Q   Q
217       CTC ACC ATC AGC AGC CTG CAG CCT GAA GAT TTT GCA ACT TAT TAC TGT CAA CAG
                  CDR3
          ~~~~~~~~~~~~~~~~~~~~~~~~
          F   N   S   Y   P   F   T   F   G   P   G   T   K   V   D   I   K
271       TTT AAT AGT TAC CCA TTC ACT TTC GGC CCT GGG ACC AAA GTG GAT ATC AAA
```

Figure 10b

Anti-PD-L1 3G10 VH region

```
                    CDR1
1-18 germline:  Q V Q L V Q S G A E V K K P G A S V K V S C K A S G Y T F T - - - - S Y G I S W V R Q
3G10 VH:        - - - - - - - - - - - - - - - - - - - - - - - - - - - - - D - - F - - - - - - -

CDR2
1-18 germline:  A P G Q G L E W M G W I S A Y N G N T N Y A Q K L Q G R V T M T T D T S T
3G10 VH:        - - - - - - - - - - - - - - T - - - - - - - - - - - - - - - - - - - -

CDR3
1-18 germline:  A Y M E L R S L R S D D T A V Y Y C A R - - D Y F Y G M D V W G Q G T T V T V S S
3G10 VH:        V - - - - - - - - - - - - - - - - - - - - - - - - - - - - - - - - - - - - -
(JH6b)
```

Figure 11

Anti-PD-L1 12A4 VH Region

```
                          CDR1
1-69 germline:  Q V Q L V Q S G A E V K K P G S S V K V S C K A
12A4 VH:        - - - - - - - - - - - - - - - - - - - - - - T CDR1
1-69 germline:  S G G T F S S Y A I S W V R Q A P G Q G L E W M
12A4 VH:        - - D - - - T - - - - - - - - - - - - - - - -

CDR2
1-69 germline:  G I I P I F G T A N Y A Q K F Q G R V T I T A
12A4 VH:        - - - - - - - K - H - - - - - - - - - - - -

1-69 germline:  D E S T S T A Y M E L S S L R S E D T A V Y Y C
12A4 VH:        - - - - - - - - - - - - - - - - - - - - - - -

CDR3
1-69 germline:  A R
JH6b germline:       Y Y Y Y Y G M D V W G Q G T T V T
12A4 VH:        - - K F H F V S G S P F - Y G M D V W G Q G T T V T JH6b germline:  V S S
12A4 VH:        - - -
```

Figure 12

Anti-PD-L1 10A5 VH region

```
                                                         CDR1
1-3 germline    Q V Q L V Q S G A E V K K P G A S V K V S C K A S G Y T F T S Y A M H W
10A5 VH         - - - - - - - - - - - - - - - - - - - - - - - - - - - - - - - - D V -

CDR2
1-3 germline    V R Q A P G Q R L E W M G W I N A G N G N T K Y S Q K F Q G R V T I T R
10A5 VH         - - - - - - - - - - - - - - - L H - D T - I - - F - - - - - - - - - - -

CDR3
1-3 germline    D T S A S T A Y M E L S S L R S E D T A V Y Y C A R
JH4b germline                                                        E R I Q L W   F D Y W
10A5 VH         - - - - - - - - - - - - - - - - - - - - - - - - -   - - - - - -   - - - -

JH4b germline   G Q G T L V T V S S   (JH4b)
10A5 VH         - - - - - - - - - -
```

Figure 13

Anti-PD-L1 5F8 VH region

```
                                                                    CDR1
1-69 germline  Q V Q L V Q S G A E V K K P G S S V K V S C K A S G G T F S S Y A I S W
5F8 VH         - - - - - - - - - - - - - - - - - - - - - - - - - - H - - T - - - N -
                                                             V CDR2
1-69 germline  V R Q A P G Q G L E W M G G I I P I F G T A N Y A Q K F Q G R V T I T A
5F8 VH         - - - - - - - - - - - - - - - - - - - - - - H - - - - - - - - - - - -

CDR3
1-69 germline  D E S T S T A Y M E L S S L R S E D T A V Y Y C A R
JH4b germline                                                     - D Q G I A A A L F D
5F8 VH         - - - - - - - - - - - - - - - - - - - - - - - - - - - - - - - - - - -

JH4b germline  Y W G Q G T L V T V S S  (JH4b)
5F8 VH         - - - - - - - - - - - -
```

Figure 14

Anti-PD-L1 10H10 VH region

```
                              CDR1
3-9 germline      E V Q L V E S G G G L V Q P G R S L R L S C A A S G F T F D D Y A M H W V R
10H10 VH          - - - - - - - - - - - - - - - - - - - - - - - - V - - - - - - - - - V V - -

CDR2
3-9 germline      Q A P G K G L E W V S G I S W N S G S I G Y A D S V K G R F T I S R D N A K
10H10 VH          - - - - - - - - - - - - - - - - G - - N - - - - - - - - - - - - - - - - - -

CDR3
3-9 germline      N S L Y L Q M N S L R A E D T A L Y Y C A
JH4b germline                                              F D Y W G Q G T L V T V S S
10H10 VH          - - - - - - - - - - - - - - - - - - - - -  - V P - - - - - - - - - - -
(JH4b)
```

Figure 15

Anti-PD-L1 1B12 VH region

```
                                                  CDR1
1-69 germline   Q V Q L V Q S G A E V K K P G S S V K V S C K A S G G T F S S Y A I S W
1B12 VH         - - - - - - - - - - - - - - - - - - - - - - - - - - - - D - - T - - - -

CDR2
1-69 germline   V R Q A P G Q G L E W M G G I I P I F G T A N Y A Q K F Q G R V T I T A
1B12 VH         - - - - - - - - - - - - - - - - - - - R - H - - - - - - - - - - - - - -

CDR3
1-69 germline   D E S T S T A Y M E L S S L R S E D T A V Y Y C A R
JH6b germline                                                       F - - K F H F V S G S P F
1B12 VH         - - - - - - - - - - - - - - - - - - - - - - - - -   F - - K F H F V S G S P F JH6b germline   G M D V W G Q G T T V T V S S   (JH6b)
1B12 VH         - - - - - - - - - - - - - - -
```

Figure 16

Anti-PD-L1 7H1 VH region

```
                                                    CDR1
1-69 germline  Q V Q L V Q S G A E V K K P G S S V K V S C K A S G G T F S S Y A I S W
7H1 VH         - - - - - - - - - - - - - - - - - - - - - - - - - - T - - - - - - - -

CDR2
1-69 germline  V R Q A P G Q G L E W M M G G I I P I F G T A N Y A Q K F Q G R V T I T A
7H1 VH         - - - - - - - - - - - - - - - - - - - - - K - H - - - - - - - - - - - -

CDR3
1-69 germline  D E S T S T A Y M E L S S L R S E D T A V Y Y C A R
JH6b germline
7H1 VH         - - - - - - T - - - - - - - - - - - - - - - - - - - K Y D Y V S G S P F Y JH6b germline  G M D V W G Q G T T V T V S S   (JH6b)
7H1 VH         - - - - - - - - - - - - - - -
```

Figure 17

Anti-PD-L1 11E6 VH region

```
                                                            CDR1
1-69 germline    Q V Q L V Q S G A E V K K P G S S V K V S C K A S G G T F S S Y A I S W
11E6 VH          - - - - - - - - - - - - - - - - - - - - - - - - - - - - - - - - - N -

CDR2
1-69 germline    V R Q A P G Q G L E W M G G I I P I F G T A N Y A Q K F Q G R V T I T A
11E6 VH          - - - - - - - - - - - - - - - - - - - S - - - - - - D - - - - - - - -

CDR3
1-69 germline    D E S T S T A Y M E L S S L R S E D T A V Y Y C A R
JH6c germline                                                     - - - - D S S G W S R Y Y M
11E6 VH          - - - - - A - - - - - - - - - - - - - - - - - - - - - - - - - - - - - -

JH6c germline    D V W G Q G T T V T V S S   (JH6c)
11E6 VH          - - - - - - - - - - - - -
```

Figure 18

Anti-PD-L1 12B7 VH region

```
                                                               CDR1
1-69 germline    Q V Q L V Q S G A E V K K P G S S V K V S C K A S G G T F S S Y A I S W
12B7 VH          - - - - - - - - - - - - - - E - - - - - - - - - - - - - - N - - - - - -

CDR2
1-69 germline    V R Q A P G Q G L E W M G G I I P I F G T A N Y A Q K F Q G R V T I T A
12B7 VH          - - - - - - - - - - - - - - - - - - L - - - I - - H - - - - - - - - - -

CDR3
1-69 germline    D E S T S T A Y M E L S S L R S E D T A V Y Y C A R
JH6b germline
12B7 VH          - - - - - N - - - - - - - - - - - - D - - - - - - - - - K Y S Y V S G S P F Y JH6b germline    G M D V W G Q G T T V T V S S    (JH6b)
12B7 VH          - - - - - - - - - - - - - - -
```

Figure 19

Anti-PD-L1 13G4 VH region

```
                                                           CDR1
                                                 ┌──────────────────┐
3-9 germline   E V Q L V E S G G G L V Q P G R S L R L S C A A S G F T F D D Y A M H W
13G4 VH        - - - - - - - - - - - - - - - - - - - - - - - - - - - - H - - - G - - -

CDR2
                               ┌────────────────────────────┐
3-9 germline   V R Q A P G K G L E W V S G I S W N S G S I G Y A D S V K G R F T I S R
13G4 VH        - -                   - - - - - - R - R - E - - - - - - - - - - - - - -

CDR3
                                                 ┌──────────────────────────────┐
3-9 germline   D N A K N S L Y L Q M N S L R A E D T A L Y Y C A K - - G R F R Y F D W E L
13G4 VH        - -                                             - -

JH4b germline  D Y W G Q G T L V T V S S   (JH4b)
13G4 VH        - -                     - -
```

Figure 20

Anti-PD-L1 3G10 VK Region

```
                                                            CDR1
L6 germline:   E I V L T Q S P A T L S L S P G E R A T L S C R A S Q S V S S Y L A
3G10 VK#1:     - - - - - - - - - - - - - - - - - - - - - - - - - - - - - - - V CDR2
L6 germline:   W Y Q Q K P G Q A P R L L I Y D A S N R A T G I P A R F S G S G S G
3G10 VK#1:     - - - - - - - - - - - - - - - - - - - - - - - - - - - - - - - -

CDR3
L6 germline:   T D F T L T I S S L E P E D F A V Y Y C Q Q R S N W P
JK1 germline:                                                       W T F G Q G T
3G10 VK#1:     - - - - - - - - - - - - - - - - - - - - - - - R -

JK1 germline:  K V E I K   (JK1)
3G10 VK#1:     - - - - -
```

Figure 21

PD-L1 12A4 VK Region

```
                                            CDR1
L6 germline:  E I V L T Q S P A T L S L S P G E R A T L S C R A S Q S V S S Y L A W Y
12A4 VK:      - - - - - - - - - - - - - - - - - - - - - - - - - - - - - - - - - - -

CDR2
L6 germline:  Q Q K P G Q A P R L L I Y D A S N R A T G I P A R F S G S G S G T D F T
12A4 VK:      - - - - - - - - - - - - - - - - - - - - - - - - - - - - - - - - - - -

CDR3
L6 germline:  L T I S S L E P E D F A V Y Y C Q Q R S N W P
JK1 germline:                                              T F G Q G T K V E I K
12A4 VK:      - - - - - - - - - - - - - - - - - - - - - - - - - - - - - - -
```

Figure 22

Anti-PD-L1 10A5 VK region

```
                                                      CDR1
L15 germline    D I Q M T Q S P S S L S A S V G D R V T I T C R A S Q G I S S
10A5 VK         - - - - - - - - - - - - - - - - - - - - - - - - - - - - - -

CDR2
L15 germline    W L A W Y Q Q K P E K A P K S L I Y A A S S L Q S G V P S R F
10A5 VK         - - - - - - - - - - - - - - - - - - - - - - - - - - - - - -

CDR3
L15 germline    S G S G T D F T L T I S S L Q P E D F A T Y Y C Q Q Y N S
10A5 VK         - - - - - - - - - - - - - - - - - - - - - - - - - - - -

L15 germline       Y P
JK2 germline           Y T F G Q G T K L E I K     (JK2)
10A5 VK            - -   - - - - - - - - - - -
```

Figure 23

Anti-PD-L1 5F8 VK1 region

```
                                                         CDR1
A27 germline    E I V L T Q S P G T L S L S P G E R A T L S C R A S Q S V S S S Y L A W
5F8 VK1         - - - - - - - - - - - - - - - - - - - - - - - - - - - - - - - - - - -

CDR2
A27 germline    Y Q Q K P G Q A P R L L I Y G A S S R A T G I P D R F S G S G S G T D F
5F8 VK1         - - - - - - - - - - - - - - - - - - - - - - - - - - - - - - - - - - -

CDR3
A27 germline    T L T I S R L E P E D F A V Y Y C Q Q Y G S S P
JK1 germline                                                     W T F G Q G T K V E I K
5F8 VK1         - - - - - - - - - - - - - - - - - - - - - - - - - - - - - - - - -
(JK1)
```

Figure 24

Anti-PD-L1 10H10 VK region

```
                                                        CDR1
L15 germline    D I Q M T Q S P S S L S A S V G D R V T I T C R A S Q G I S S
10H10 VK        - - - - - - - - - - - - - - - - - - - - - - - - - - - - - -

CDR2
L15 germline    W L A W Y Q Q K P E K A P K S L I Y A A S S L Q S G V P S R F
10H10 VK        - - - - - - - - - - - - - - - - - - - - - - - - - - - - - -

CDR3
L15 germline    S G S G S G T D F T L T I S S L Q P E D F A T Y Y C Q Q Y N S
10H10 VK        - - - - - - - - - - - - - - - - - - - - - - - - - - - - - -

L15 germline    Y P
JK2 germline         Y T F G Q G T K L E I K    (JK2)
10H10 VK        - -  - - - - - - - - - - - -
```

Figure 25

Anti-PD-L1 1B12 VK region

```
                                                      CDR1
                                                ┌──────────────┐
L6 germline    E I V L T Q S P A T L S L S P G E R A T L S C R A S Q S V S S - -
1B12 VK        - - - - - - - - - - - - - - - - - - - - - - - - - - - - - - - -

CDR2
                                    ┌──────────────┐
L6 germline    Y L A W Y Q Q K P G Q A P R L L I Y D A S N R A T G I P A R F - -
1B12 VK        - - - - - - - - - - - - - - - - - - - - - - - - - - - - - - - -

CDR3
                                                        ┌──────────────┐
L6 germline    S G S G S G T D F T L T I S S L E P E D F A V Y Y C Q Q R S N - -
1B12 VK        - - - - - - - - - - - - - - - - - - - - - - - - - - - - - - - -

L6 germline    W P
JK1 germline        T F G Q G T K V E I K -        (JK1)
1B12 VK        - -  - - - - - - - - - - - -
```

Figure 26

Anti-PD-L1 7H1 VK region

```
                                                    CDR1
L6 germline    E I V L T Q S P A T L S L S P G E R A T L S C R A S Q S V S S
7H1 VK         - - - - - - - - - - - - - - - - - - - - - - - - - - - - - -

CDR2
L6 germline    Y L A W Y Q Q K P G Q A P R L L I Y D A S N R A T G I P A R F
7H1 VK         - -                         - - - - - - - - - -

L6 germline    S G S G S G T D F T L T I S S L E P E D F A V Y Y C Q Q R S N
7H1 VK         - - - - - - - - - - - - - - - - - - - - - - - - -    CDR3

L6 germline    W P
JK1 germline        T F G Q G T K V E I K   (JK1)
7H1 VK         - -  - - - - - - - - - -
```

Figure 27

Anti-PD-L1 11E6 VK1 region

```
                                                   CDR1
A27 germline    E I V L T Q S P G T L S L S P G E R A T L S C R A S Q S V S S S Y L A W
11E6 VK1        - - - - - - - - - - - - - - - - - - - - - - - - - - - - - - - - - - -

CDR2
A27 germline    Y Q Q K P G Q A P R L L I Y G A S S R A T G I P D R F S G S G S G T D F
11E6 VK1        - - - - - - - - - - - - - - - - - - - - - - - - - - - - - - - - - - -

CDR3
A27 germline    T L T I S R L E P E D F A V Y Y C Q Q Y G S S P
JK4 germline                                                   F G G G T K V E I K  (JK4)
11E6 VK1        - - - - - - - - - - - - - - - - - - - - - - -   - - - - - - - - -
```

Figure 28

Anti-PD-L1 11E6a VK2 region

```
                                                                CDR1
A27 germline    E I V L T Q S P G T L S L S P G E R A T L S C R A S Q S V S S S Y L A W
11E6 VK2        - - - - - - - - - - - - - - - - - - - - - - - - - - - - - - - - - - -

CDR2
A27 germline    Y Q Q K P G Q A P R L L I Y G A S S R A T G I P D R F S G S G S G T D F
11E6 VK2        - - - - - - - - - - - - - - - - - - - - - - - - - - - - - - - - - - -

CDR3
A27 germline    T L T I S R L E P E D F A V Y Y C Q Q Y G S S P
JK4 germline                                                    T F G G G T K V E I K   (JK4)
11E6 VK2        - - - - - - - - - - - - - - - - - - - - - - -  - - - - - - - - - - -
```

Figure 29

Anti-PD-L1 12B7 VK region

```
                                                     CDR1
L6 germline   E I V L T Q S P A T L S L S P G E R A T L S C R A S Q S V S S
12B7 VK       - - - - - - - - - - - - - - - - - - - - - - - - - - - - - -

CDR2
L6 germline   Y L A W Y Q Q K P G Q A P R L L I Y D A S N R A T G I P A R F
12B7 VK       - - - - - - - - - - - - - - - - - - - - - - - - - - - - - -

CDR3
L6 germline   S G S G S G T D F T L T I S S L E P E D F A V Y Y C Q Q R S N
12B7 VK       - - - - - - - - - - - - - - - - - - - - - - - - - - - - - -

L6 germline        W P
JK5 germline            T F G Q G T R L E I K    (JK5)
12B7 VK       - -  - -  - - - - - - - - - - -
```

Figure 30

Anti-PD-L1 13G4 VK region

```
                          CDR1
L18 germline    A I Q L T Q S P S S L S A S V G D R V T I T C R A S Q G I S S
13G4 VK         - - - - - - - - - - - - - - - - - - - - - - - - - - - - - -

CDR2
L18 germline    A L A W Y Q Q K P G K A P K L L I Y D A S S L E S G V P S R F
13G4 VK         - - - - - - - - - - - - - - - - - - - - - - - - - - - - - -

CDR3
L18 germline    S G S G S G T D F T L T I S S L Q P E D F A T Y Y C Q Q F N S
13G4 VK         - - - - - - - - - - - - - - - - - - - - - - - - - - - - - -

L18 germline    Y P
JK3 germline      F T F G P G T K V D I K    (JK3)
13G4 VK         - - - - - - - - - - - - -
```

Figure 31

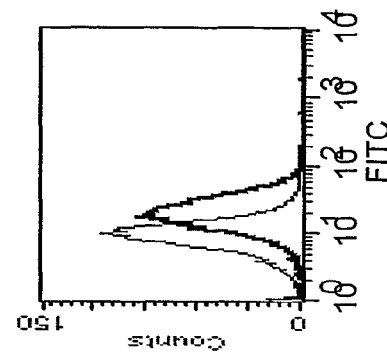
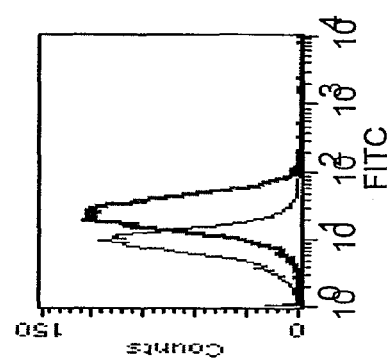
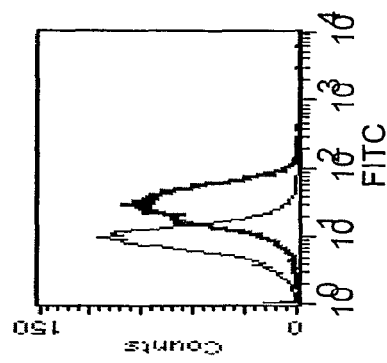

HUMAN MONOCLONAL ANTIBODIES TO PROGRAMMED DEATH LIGAND 1 (PD-L1)

CROSS-REFERENCE TO RELATED APPLICATIONS

This application is a divisional of U.S. application Ser. No. 14/807,522, filed Jul. 23, 2015, which is a divisional of U.S. application Ser. No. 13/746,773, filed Jan. 22, 2013, now U.S. Pat. No. 9,102,725, which is a divisional application of U.S. application Ser. No. 13/091,936, filed Apr. 21, 2011, now issued as U.S. Pat. No. 8,383,796, which is a divisional application of U.S. application Ser. No. 11/917,727, having 371(c) date of Jun. 9, 2008, now issued as U.S. Pat. No. 7,943,743, which is a national phase of PCT Appl. No. PCT/US2006/026046, filed Jun. 30, 2006, which claims the benefit of U.S. Provisional Patent Application No. 60/696,426, filed Jul. 1, 2005, each of which is incorporated herein by reference in its entirety.

REFERENCE TO A SEQUENCE LISTING

The instant application contains a Sequence Listing, which has been submitted in ASCII text file format via EFS-Web and is hereby incorporated by reference in its entirety. Said ASCII copy, created on Jun. 17, 2016, is named "3338_0370006_SeqListing_ST25.txt", and is 77,664 bytes in size.

BACKGROUND

Programmed death 1 (PD-1) is a member of the CD28 family of receptors, which includes CD28, CTLA-4, ICOS, PD-1, and BTLA. The initial members of the family, CD28 and ICOS, were discovered by functional effect on augmenting T cell proliferation following the addition of monoclonal antibodies (Hutloff et al. (1999) *Nature* 397:263-266; Hansen et al. (1980) *Immunogenics* 10:247-260). Two cell surface glycoprotein ligands for PD-1 have been identified, PD-L1 and PD-L2, and have been shown to downregulate T cell activation and cytokine secretion upon binding to PD-1 (Freeman et al. (2000) *J Exp Med* 192:1027-34; Latchman et al. (2001) *Nat Immunol* 2:261-8; Carter et al. (2002) *Eur J Immunol* 2:634-43; Ohigashi et al. (2005) *Clin Cancer Res* 11:2947-53). Both PD-L1 (B7-H1) and PD-L2 (B7-DC) are B7 homologs that bind to PD-1, but do not bind to other CD28 family members (Blank et al. (2004). Expression of PD-L1 on the cell surface has also been shown to be upregulated through IFN-γ stimulation.

PD-L1 expression has been found in several murine and human cancers, including human lung, ovarian and colon carcinoma and various myelomas (Iwai et al. (2002) *PNAS* 99:12293-7; Ohigashi et al. (2005) *Clin Cancer Res* 11:2947-53). PD-L1 has been suggested to play a role in tumor immunity by increasing apoptosis of antigen-specific T-cell clones (Dong et al. (2002) *Nat Med* 8:793-800). It has also been suggested that PD-L1 might be involved in intestinal mucosal inflammation and inhibition of PD-L1 suppresses wasting disease associated with colitis (Kanai et al. (2003) *J Immunol* 121:4156-63).

SUMMARY

The present invention provides isolated monoclonal antibodies, in particular human monoclonal antibodies that bind to PD-L1 and exhibit numerous desirable properties. These properties include high affinity binding to human PD-L1. Still further, antibodies of the invention have been shown to increase T-cell proliferation, IFN-γ secretion, and IL-2 secretion in a mixed lymphocyte reaction.

In one aspect, the invention pertains to an isolated monoclonal antibody, or an antigen-binding portion thereof wherein the antibody exhibits at least one of the following properties:
(a) binds to human PD-L1 with a $K_D$ of $1 \times 10^{-7}$ M or less;
(b) increases T-cell proliferation in a mixed lymphocyte reaction (MLR) assay;
(c) increases interferon-γ production in an MLR assay;
(d) increases IL-2 secretion in an MLR assay;
(e) stimulates antibody responses; or
(f) reverses the effect of T regulatory cells on T cell effector cells and/or dendritic cells.

Preferably the antibody is a human antibody, although in alternative embodiments the antibody can be, for example, a murine antibody, a chimeric antibody or humanized antibody.

In particular embodiments, the antibody binds to human PD-L1 with a $K_D$ of $5 \times 10^{-8}$ M or less, binds to human PD-L1 with a $K_D$ of $1 \times 10^{-8}$ M or less, binds to human PD-L1 with a $K_D$ of $5 \times 10^{-8}$ M or less, binds to human PD-L1 with a $K_D$ of $5 \times 10^{-9}$ M or less, or binds to human PD-L1 with a $K_D$ of between $1 \times 10$-M and $1 \times 10^{-10}$ M.

In another embodiment, the invention provides an isolated monoclonal antibody, or antigen binding portion thereof, wherein the antibody cross-competes for binding to PD-L1 with a reference antibody comprising:
(a) the human heavy chain variable region comprises an amino acid sequence selected from the group consisting of SEQ ID NOs:1, 2, 3, 4, 5, 6, 7, 8, 9, and 10; and
(b) the human light chain variable region comprises an amino acid sequence selected from the group consisting of SEQ ID NOs:11, 12, 13, 14, 15, 16, 17, 18, 19, and 20.

In various embodiments, the reference antibody comprises:
(a) a heavy chain variable region comprising the amino acid sequence of SEQ ID NO:1; and
(b) a light chain variable region comprising the amino acid sequence of SEQ ID NO:11;
or the reference antibody comprises:
(a) a heavy chain variable region comprising the amino acid sequence of SEQ ID NO:2; and
(b) a light chain variable region comprising the amino acid sequence of SEQ ID NO:12;
or the reference antibody comprises:
(a) a heavy chain variable region comprising the amino acid sequence of SEQ ID NO:3; and
(b) a light chain variable region comprising the amino acid sequence of SEQ ID NO:13;
or the reference antibody comprises:
(a) a heavy chain variable region comprising the amino acid sequence of SEQ ID NO:4; and
(b) a light chain variable region comprising the amino acid sequence of SEQ ID NO:14;
or the reference antibody comprises:
(a) a heavy chain variable region comprising the amino acid sequence of SEQ ID NO:5; and
(b) a light chain variable region comprising the amino acid sequence of SEQ ID NO:15;
or the reference antibody comprises:
(a) a heavy chain variable region comprising the amino acid sequence of SEQ ID NO:6; and
(b) a light chain variable region comprising the amino acid sequence of SEQ ID NO:16;

or the reference antibody comprises:
  (a) a heavy chain variable region comprising the amino acid sequence of SEQ ID NO:7; and
  (b) a light chain variable region comprising the amino acid sequence of SEQ ID NO:17;
or the reference antibody comprises:
  (a) a heavy chain variable region comprising the amino acid sequence of SEQ ID NO:8; and
  (b) a light chain variable region comprising the amino acid sequence of SEQ ID NO: 18;
or the reference antibody comprises:
  (a) a heavy chain variable region comprising the amino acid sequence of SEQ ID NO:9; and
  (b) a light chain variable region comprising the amino acid sequence of SEQ ID NO-19;
or the reference antibody comprises:
  (a) a heavy chain variable region comprising the amino acid sequence of SEQ ID NO:10; and
  (b) a light chain variable region comprising the amino acid sequence of SEQ ID NO:20.

In another aspect, the invention pertains to an isolated monoclonal antibody, or an antigen-binding portion thereof comprising a heavy chain variable region that is the product of or derived from a human $V_H$ 1-18 gene, wherein the antibody specifically binds PD-L1. The invention further provides an isolated monoclonal antibody, or an antigen-binding portion thereof, comprising a heavy chain variable region that is the product of or derived from a human $V_H$ 1-69 gene, wherein the antibody specifically binds PD-L1. The invention farther provides an isolated monoclonal antibody, or an antigen-binding portion thereof, comprising a heavy chain variable region that is the product of or derived from a human $V_H$ 1-3 gene, wherein the antibody specifically binds PD-L1. The invention further provides an isolated monoclonal antibody, or an antigen-binding portion thereof, comprising a heavy chain variable region that is the product of or derived from a human $V_H$ 3-9 gene, wherein the antibody specifically binds PD-L1. The invention further provides an isolated monoclonal antibody, or an antigen-binding portion thereof, comprising a light chain variable region that is the product of or derived from a human $V_K$ L6 gene, wherein the antibody specifically binds PD-L1. The invention further provides an isolated monoclonal antibody, or an antigen-binding portion thereof, comprising a light chain variable region that is the product of or derived from a human $V_K$ L15 gene, wherein the antibody specifically binds PD-L1. The invention further provides an isolated monoclonal antibody, or an antigen-binding portion thereof, comprising a light chain variable region that is the product of or derived from a human $V_K$ A27 gene, wherein the antibody specifically binds PD-L1. The invention further provides an isolated monoclonal antibody, or an antigen-binding portion thereof, comprising a light chain variable region that is the product of or derived from a human V, L18 gene, wherein the antibody specifically binds PD-L1.

In a particularly preferred embodiment, the invention provides an isolated monoclonal antibody, or an antigen-binding portion thereof, comprising:
  (a) a heavy chain variable region of a human $V_H$ 1-18 gene; and
  (b) a light chain variable region of a human $V_K$ L6 gene; wherein the antibody specifically binds to PD-L1.

In another preferred embodiment, the invention provides an isolated monoclonal antibody, or an antigen-binding portion thereof comprising:
  (a) a heavy chain variable region of a human $V_H$ 1-69 gene; and
  (b) a light chain variable region of a human $V_K$ L6 gene; wherein the antibody specifically binds to PD-L1.

In another preferred embodiment, the invention provides an isolated monoclonal antibody, or an antigen-binding portion thereof comprising:
  (a) a heavy chain variable region of a human $V_H$ 1-3 gene; and
  (b) a light chain variable region of a human $V_K$ L15 gene; wherein the antibody specifically binds to PD-L1.

In another preferred embodiment, the invention provides an isolated monoclonal antibody, or an antigen-binding portion thereof comprising:
  (a) a heavy chain variable region of a human $V_H$ 1-69 gene; and
  (b) a light chain variable region of a human $V_K$ L15 gene; wherein the antibody specifically binds to PD-L1.

In another preferred embodiment, the invention provides an isolated monoclonal antibody, or an antigen-binding portion thereof; comprising:
  (a) a heavy chain variable region of a human $V_H$ 3-9 gene; and
  (b) a light chain variable region of a human $V_K$ L15 gene; wherein the antibody specifically binds to PD-L1.

In another preferred embodiment, the invention provides an isolated monoclonal antibody, or an antigen-binding portion thereof; comprising:
  (a) a heavy chain variable region of a human VH 3-9 gene; and
  (b) a light chain variable region of a human $V_K$ L18 gene; wherein the antibody specifically binds to PD-L1.

In another aspect, the invention provides an isolated monoclonal antibody, or antigen binding portion thereof, comprising:
  a heavy chain variable region that comprises CDR1, CDR2, and CDR3 sequences; and a light chain variable region that comprises CDR1, CDR2, and CDR3 sequences, wherein:
  (a) the heavy chain variable region CDR3 sequence comprises an amino acid sequence selected from the group consisting of SEQ ID NOs:41, 42, 43, 44, 45, 46, 47, 48, 49, and 50, and conservative modifications thereof;
  (b) the light chain variable region CDR3 sequence comprises an amino acid sequence selected from the group consisting of SEQ ID NOs:71, 72, 73, 74, 75, 76, 77, 78, 79, and 80, and conservative modifications thereof; and
  (c) the antibody specifically binds to human PD-L1.

Preferably, the heavy chain variable region CDR2 sequence comprises an amino acid sequence selected from the group consisting of amino acid sequences of SEQ ID NOs:31, 32, 33, 34, 35, 36, 37, 38, 39, and 40, and conservative modifications thereof; and the light chain variable region CDR2 sequence comprises an amino acid sequence selected from the group consisting of amino acid sequences of SEQ ID NOs:61, 62, 63, 64, 65, 66, 67, 68, 69, and 70, and conservative modifications thereof. Preferably, the heavy chain variable region CDR1 sequence comprises an amino acid sequence selected from the group consisting of amino acid sequences of SEQ ID NOs:21, 22, 23, 24, 25, 26, 27, 28, 29, and 30, and conservative modifications thereof; and the light chain variable region CDR1 sequence comprises an amino acid sequence selected from the group consisting of amino acid sequences of SEQ ID NOs:51, 52, 53, 54, 55, 56, 57, 58, 59, and 60, and conservative modifications thereof.

In yet another aspect, the invention provides an isolated monoclonal antibody, or antigen binding portion thereof; comprising a heavy chain variable region and a light chain variable region, wherein:
- (a) the heavy chain variable region comprises an amino acid sequence that is at least 80% homologous to an amino acid sequence selected from the group consisting of SEQ ID NOs:1, 2, 3, 4, 5, 6, 7, 8, 9, and 10;
- (b) the light chain variable region comprises an amino acid sequence that is at least 80% homologous to an amino acid sequence selected from the group consisting of SEQ ID NOs:11, 12, 13, 14, 15, 16, 17, 18, 19, and 20; and
- (c) the antibody binds to human PD-L1 with a $K_D$ of $1 \times 10^{-7}$ M or less.

In a preferred embodiment, the antibodies additionally comprise at least one of the following properties:
- (a) the antibody increases T-cell proliferation in a mixed lymphocyte reaction (MLR) assay;
- (b) the antibody increases interferon-γ production in an MLR assay; or
- (c) the antibody increases IL-2 secretion in an MLR assay.

In preferred embodiments, the invention provides an isolated monoclonal antibody, or antigen binding portion thereof comprising:
- (a) a heavy chain variable region CDR1 comprising an amino acid sequence selected from the group consisting of SEQ ID NOs:21, 22, 23, 24, 25, 26, 27, 28, 29, and 30;
- (b) a heavy chain variable region CDR2 comprising an amino acid sequence selected from the group consisting of SEQ ID NOs:31, 32, 33, 34, 35, 36, 37, 38, 39, and 40;
- (c) a heavy chain variable region CDR3 comprising an amino acid sequence selected from the group consisting of SEQ ID NOs:41, 42, 43, 44, 45, 46, 47, 48, 49, and 50;
- (d) a light chain variable region CDR1 comprising an amino acid sequence selected from the group consisting of SEQ ID NOs:51, 52, 53, 54, 55, 56, 57, 58, 59, and 60;
- (e) a light chain variable region CDR2 comprising an amino acid sequence selected from the group consisting of SEQ ID NOs:61, 62, 63, 64, 65, 66, 67, 68, 69, and 70; and
- (f) a light chain variable region CDR3 comprising an amino acid sequence selected from the group consisting of SEQ ID NOs:71, 72, 73, 74, 75, 76, 77, 78, 79, and 80;

wherein the antibody specifically binds PD-L1.

A preferred combination comprises:
- (a) a heavy chain variable region CDR1 comprising SEQ ID NO:21;
- (b) a heavy chain variable region CDR2 comprising SEQ ID NO:31;
- (c) a heavy chain variable region CDR3 comprising SEQ ID NO:41;
- (d) a light chain variable region CDR1 comprising SEQ ID NO:51;
- (e) a light chain variable region CDR2 comprising SEQ ID NO:61; and
- (f) a light chain variable region CDR3 comprising SEQ ID NO:71.

Another preferred combination comprises:
- (a) a heavy chain variable region CDR1 comprising SEQ ID NO:22;
- (b) a heavy chain variable region CDR2 comprising SEQ ID NO:32;
- (c) a heavy chain variable region CDR3 comprising SEQ ID NO:42;
- (d) a light chain variable region CDR1 comprising SEQ ID NO:52;
- (e) a light chain variable region CDR2 comprising SEQ ID NO:62; and
- (f) a light chain variable region CDR3 comprising SEQ ID NO:72.

Another preferred combination comprises:
- (a) a heavy chain variable region CDR1 comprising SEQ ID NO:23;
- (b) a heavy chain variable region CDR2 comprising SEQ ID NO:33;
- (c) a heavy chain variable region CDR3 comprising SEQ ID NO:43;
- (d) a light chain variable region CDR1 comprising SEQ II) NO:53;
- (e) a light chain variable region CDR2 comprising SEQ ID NO:63; and
- (f) a light chain variable region CDR3 comprising SEQ ID NO:73.

Another preferred combination comprises:
- (a) a heavy chain variable region CDR1 comprising SEQ ID NO:24;
- (b) a heavy chain variable region CDR2 comprising SEQ ID NO:34;
- (c) a heavy chain variable region CDR3 comprising SEQ ID NO:44;
- (d) a light chain variable region CDR1 comprising SEQ ID NO:54;
- (e) a light chain variable region CDR2 comprising SEQ ID NO:64; and
- (f) a light chain variable region CDR3 comprising SEQ ID NO:74.

Another preferred combination comprises:
- (a) a heavy chain variable region CDR1 comprising SEQ ID NO:25;
- (b) a heavy chain variable region CDR2 comprising SEQ ID NO:35;
- (c) a heavy chain variable region CDR3 comprising SEQ ID NO:45;
- (d) a light chain variable region CDR1 comprising SEQ ID NO:55;
- (e) a light chain variable region CDR2 comprising SEQ ID NO:65; and
- (f) a light chain variable region CDR3 comprising SEQ ID) NO:75.

Another preferred combination comprises:
- (a) a heavy chain variable region CDR1 comprising SEQ ID NO:26;
- (b) a heavy chain variable region CDR2 comprising SEQ ID NO:36;
- (c) a heavy chain variable region CDR3 comprising SEQ ID NO:46;
- (d) a light chain variable region CDR1 comprising SEQ ID NO:56;
- (e) a light chain variable region CDR2 comprising SEQ ID NO:66; and
- (f) a light chain variable region CDR3 comprising SEQ ID NO:76.

Another preferred combination comprises:
- (a) a heavy chain variable region CDR1 comprising SEQ ID NO:27;
- (b) a heavy chain variable region CDR2 comprising SEQ ID NO:37;

(o) a heavy chain variable region CDR3 comprising SEQ ID NO:47;
(d) a light chain variable region CDR1 comprising SEQ ID NO:57;
(e) a light chain variable region CDR2 comprising SEQ ID NO:67; and
(f) a light chain variable region CDR3 comprising SEQ ID NO:77.

Another preferred combination comprises:
(a) a heavy chain variable region CDR1 comprising SEQ ID NO:28;
(b) a heavy chain variable region CDR2 comprising SEQ ID NO:38;
(c) a heavy chain variable region CDR3 comprising SEQ ID NO:48;
(d) a light chain variable region CDR1 comprising SEQ ID NO:58;
(e) a light chain variable region CDR2 comprising SEQ ID NO:68; and
(f) a light chain variable region CDR3 comprising SEQ ID NO:78.

Another preferred combination comprises:
(a) a heavy chain variable region CDR1 comprising SEQ ID NO:29;
(b) a heavy chain variable region CDR2 comprising SEQ ID NO:39;
(c) a heavy chain variable region CDR3 comprising SEQ ID NO:49;
(d) a light chain variable region CDR1 comprising SEQ ID NO:59;
(e) a light chain variable region CDR2 comprising SEQ ID NO:69; and
(f) a light chain variable region CDR3 comprising SEQ ID NO:79.

Another preferred combination comprises:
(a) a heavy chain variable region CDR1 comprising SEQ ID NO:30;
(b) a heavy chain variable region CDR2 comprising SEQ ID NO:40;
(c) a heavy chain variable region CDR3 comprising SEQ ID NO:50;
(d) a light chain variable region CDR1 comprising SEQ ID NO:60;
(e) a light chain variable region CDR2 comprising SEQ ID NO:70; and
(f) a light chain variable region CDR3 comprising SEQ ID NO:80.

Other preferred antibodies of the invention, or antigen binding portions thereof comprise:
(a) a heavy chain variable region comprising an amino acid sequence selected from the group consisting of SEQ ID NOs:1, 2, 3, 4, 5, 6, 7, 8, 9, and 10; and
(b) a light chain variable region comprising an amino acid sequence selected from the group consisting of SEQ ID NOs:11, 12, 13, 14, 15, 16, 17, 18, 19, and 20; wherein the antibody specifically binds PD-L1.

A preferred combination comprises:
(a) a heavy chain variable region comprising the amino acid sequence of SEQ ID NO:1; and
(b) a light chain variable region comprising the amino acid sequence of SEQ ID NO:11.

Another preferred combination comprises:
(a) a heavy chain variable region comprising the amino acid sequence of SEQ ID NO:2; and
(b) a light chain variable region comprising the amino acid sequence of SEQ ID NO:12.

Another preferred combination comprises:
(a) a heavy chain variable region comprising the amino acid sequence of SEQ ID) NO:3; and
(b) a light chain variable region comprising the amino acid sequence of SEQ ID NO:13.

Another preferred combination comprises:
(a) a heavy chain variable region comprising the amino acid sequence of SEQ ID NO:4; and
(b) a light chain variable region comprising the amino acid sequence of SEQ ID NO:14.

Another preferred combination comprises:
(a) a heavy chain variable region comprising the amino acid sequence of SEQ ID NO:5; and
(b) a light chain variable region comprising the amino acid sequence of SEQ ID NO:15.

Another preferred combination comprises:
(a) a heavy chain variable region comprising the amino acid sequence of SEQ ID NO:6; and
(b) a light chain variable region comprising the amino acid sequence of SEQ ID NO:16.

Another preferred combination comprises:
(a) a heavy chain variable region comprising the amino acid sequence of SEQ ID NO:7; and
(b) a light chain variable region comprising the amino acid sequence of SEQ ID NO:17.

Another preferred combination comprises:
(a) a heavy chain variable region comprising the amino acid sequence of SEQ ID NO-8; and
(b) a light chain variable region comprising the amino acid sequence of SEQ ID NO:18.

Another preferred combination comprises:
(a) a heavy chain variable region comprising the amino acid sequence of SEQ ID NO:9; and
(b) a light chain variable region comprising the amino acid sequence of SEQ ID NO:19.

Another preferred combination comprises:
(a) a heavy chain variable region comprising the amino acid sequence of SEQ ID NO:10; and
(b) a light chain variable region comprising the amino acid sequence of SEQ ID NO:20.

In another aspect of the instant disclosure, antibodies, or antigen-binding portions thereof, are provided that compete for binding to PD-L1 with any of the aforementioned antibodies.

The antibodies of the instant disclosure can be, for example, full-length antibodies, for example of an IgG1 or IgG4 isotype. Alternatively, the antibodies can be antibody fragments, such as Fab or Fab'2 fragments, or single chain antibodies.

The instant disclosure also provides an immunoconjugate comprising an antibody of the invention, or antigen-binding portion thereof, linked to a therapeutic agent, such as a cytotoxin or a radioactive isotope. The invention also provides a bispecific molecule comprising an antibody, or antigen-binding portion thereof, of the invention, linked to a second functional moiety having a different binding specificity than said antibody, or antigen binding portion thereof.

Compositions comprising an antibody, or antigen-binding portion thereof; or immunoconjugate or bispecific molecule of the instant disclosure and a pharmaceutically acceptable carrier are also provided.

Nucleic acid molecules encoding the antibodies, or antigen-binding portions thereof, of the invention are also encompassed by the invention, as well as expression vectors comprising such nucleic acids and host cells comprising such expression vectors. Moreover, the invention provides a transgenic mouse comprising human immunoglobulin heavy and light chain transgenes, wherein the mouse expresses an antibody of the invention, as well as hybridomas prepared from such a mouse, wherein the hybridoma produces the antibody of the invention.

In yet another aspect, the invention provides a method of modulating an immune response in a subject comprising administering to the subject the antibody, or antigen-binding portion thereof, of the invention such that the immune response in the subject is modulated. Preferably, the antibody of the invention enhances, stimulates or increases the immune response in the subject.

In a further aspect, the invention provides a method of inhibiting growth of tumor cells in a subject, comprising administering to a subject a therapeutically effective amount of an anti-PD-L1 antibody, or antigen-binding portion thereof. The antibodies of the invention are preferred for use in the method although other anti-PD-L1 antibodies can be used instead (or in combination with an anti-PD-L1 antibody of the invention). For example, a chimeric, humanized or fully human anti-PD-L1 antibody can be used in the method of inhibiting tumor growth.

In a further aspect, the invention provides a method of treating an infectious disease in a subject, comprising administering to a subject a therapeutically effective amount of an anti-PD-L1 antibody, or antigen-binding portion thereof. The antibodies of the invention are preferred for use in the method although other anti-PD-L1 antibodies can be used instead (or in combination with an anti-PD-L1 antibody of the invention). For example, a chimeric, humanized or fully human anti-PD-L1 antibody can be used in the method of treating an infectious disease.

Still further, the invention provides a method of enhancing an immune response to an antigen in a subject, comprising administering to the subject: (I) the antigen; and (ii) an anti-PD-L1 antibody, or antigen-binding portion thereof, such that an immune response to the antigen in the subject is enhanced. The antigen can be, for example, a tumor antigen, a viral antigen, a bacterial antigen or an antigen from a pathogen. The antibodies of the invention are preferred for use in the method although other anti-PD-L1 antibodies can be used instead (or in combination with an anti-PD-L1 antibody of the invention). For example, a chimeric, humanized or fully human anti-PD-L1 antibody can be used in the method of enhancing an immune response to an antigen in a subject.

The invention also provides methods for making "second generation" anti-PD-L1 antibodies based on the sequences of the anti-PD-L1 antibodies provided herein. For example, the invention provides a method for preparing an anti-PD-L1 antibody comprising:

(a) providing: (i) a heavy chain variable region antibody sequence comprising a CDR1 sequence that is selected from the group consisting of SEQ ID NOs:21, 22, 23, 24, 25, 26, 27, 28, 29, and 30, a CDR2 sequence that is selected from the group consisting of SEQ ID NOs:31, 32, 33, 34, 35, 36, 37, 38, 39, and 40; and a CDR3 sequence that is selected from the group consisting of SEQ ID NOs:41, 42, 43, 44, 45, 46, 47, 48, 49, and 50; or (ii) a light chain variable region antibody sequence comprising a CDR1 sequence that is selected from the group consisting of SEQ ID NOs:51, 52, 53, 54, 55, 56, 57, 58, 59, and 60, a CDR2 sequence that is selected from the group consisting of SEQ ID NOs:61, 62, 63, 64, 65, 66, 67, 68, 69, and 70, and a CDR3 sequence that is selected from the group consisting of SEQ ID NOs:71, 72, 73, 74, 75, 76, 77, 78, 79, and 80;

(b) altering at least one amino acid residue within at least one variable region antibody sequence, said sequence being selected from the heavy chain variable region antibody sequence and the light chain variable region antibody sequence, to create at least one altered antibody sequence; and (c) expressing the altered antibody sequence as a protein.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWING

FIG. 1A shows the nucleotide sequence (SEQ ID NO:81) and amino acid sequence (SEQ ID NO:1) of the heavy chain variable region of the 3G10 human monoclonal antibody. The CDR1 (SEQ ID NO:21), CDR2 (SEQ ID NO:31) and CDR3 (SEQ ID NO:41) regions are delineated and the V, D and J germline derivations are indicated.

FIG. 1B shows the nucleotide sequence (SEQ ID NO:91) and amino acid sequence (SEQ ID NO: 11) of the light chain variable region of the 3G10 human monoclonal antibody. The CDR1 (SEQ ID NO:51), CDR2 (SEQ ID NO:61) and CDR3 (SEQ ID NO:71) regions are delineated and the V and J germline derivations are indicated.

FIG. 2A shows the nucleotide sequence (SEQ ID NO:82) and amino acid sequence (SEQ ID NO:2) of the heavy chain variable region of the 12A4 human monoclonal antibody. The CDR1 (SEQ ID NO:22), CDR2 (SEQ ID NO:32) and CDR3 (SEQ ID NO:42) regions are delineated and the V and J germline derivations are indicated.

FIG. 2B shows the nucleotide sequence (SEQ ID NO:92) and amino acid sequence (SEQ ID NO: 12) of the light chain variable region of the 12A4 human monoclonal antibody. The CDR1 (SEQ ID NO:52), CDR2 (SEQ ID NO:62) and CDR3 (SEQ ID NO:72) regions are delineated and the V and J germline derivations are indicated.

FIG. 3A shows the nucleotide sequence (SEQ ID NO:83) and amino acid sequence (SEQ ID NO:3) of the heavy chain variable region of the 10A5 human monoclonal antibody. The CDR1 (SEQ ID NO:23), CDR2 (SEQ ID NO:33) and CDR3 (SEQ ID NO:43) regions are delineated and the V and J germline derivations are indicated.

FIG. 3B shows the nucleotide sequence (SEQ ID NO:93) and amino acid sequence (SEQ ID NO: 13) of the light chain variable region of the 10A5 human monoclonal antibody. The CDR1 (SEQ ID NO:53), CDR2 (SEQ ID NO:63) and CDR3 (SEQ ID NO:73) regions are delineated and the V and J germline derivations are indicated.

FIG. 4A shows the nucleotide sequence (SEQ ID NO:84) and amino acid sequence (SEQ ID NO:4) of the heavy chain variable region of the 5F8 human monoclonal antibody. The CDR1 (SEQ ID NO:24), CDR2 (SEQ ID NO:34) and CDR3 (SEQ ID NO:44) regions are delineated and the V and J germline derivations are indicated.

FIG. 4B shows the nucleotide sequence (SEQ ID NO-94) and amino acid sequence (SEQ ID NO: 14) of the light chain variable region of the 5F8 human monoclonal antibody. The CDR1 (SEQ ID NO:54), CDR2 (SEQ ID NO:64) and CDR3 (SEQ ID NO:74) regions are delineated and the V and J germline derivations are indicated.

FIG. 5A shows the nucleotide sequence (SEQ ID NO:85) and amino acid sequence (SEQ ID NO:5) of the heavy chain variable region of the 10H10 human monoclonal antibody. The CDR1 (SEQ ID NO:25), CDR2 (SEQ ID NO:35) and CDR3 (SEQ ID NO:45) regions are delineated and the V and J germline derivations are indicated.

FIG. 5B shows the nucleotide sequence (SEQ ID NO:95) and amino acid sequence (SEQ ID NO:15) of the light chain variable region of the 10H10 human monoclonal antibody. The CDR1 (SEQ ID NO:55), CDR2 (SEQ ID NO:65) and CDR3 (SEQ ID NO:75) regions are delineated and the V and J germline derivations are indicated.

FIG. 6A shows the nucleotide sequence (SEQ ID NO:86) and amino acid sequence (SEQ ID NO:6) of the heavy chain variable region of the 1B12 human monoclonal antibody. The CDR1 (SEQ ID NO:26), CDR2 (SEQ ID NO:36) and CDR3 (SEQ ID NO:46) regions are delineated and the V and J germline derivations are indicated.

FIG. 6B shows the nucleotide sequence (SEQ ID NO:96) and amino acid sequence (SEQ ID NO: 16) of the light chain variable region of the 1B12 human monoclonal antibody. The CDR1 (SEQ ID NO:56), CDR2 (SEQ ID NO:66) and CDR3 (SEQ ID NO:76) regions are delineated and the V and J germline derivations are indicated.

FIG. 7A shows the nucleotide sequence (SEQ ID NO:87) and amino acid sequence (SEQ ID NO:7) of the heavy chain variable region of the 7H1 human monoclonal antibody. The CDR1 (SEQ ID NO:27), CDR2 (SEQ ID NO:37) and CDR3 (SEQ ID NO:47) regions are delineated and the V and J germline derivations are indicated.

FIG. 7B shows the nucleotide sequence (SEQ ID NO:97) and amino acid sequence (SEQ ID NO:17) of the light chain variable region of the 7H1 human monoclonal antibody. The CDR1 (SEQ ID NO:57), CDR2 (SEQ ID NO:67) and CDR3 (SEQ ID NO:77) regions are delineated and the V and J germline derivations are indicated.

FIG. 8A shows the nucleotide sequence (SEQ ID NO:88) and amino acid sequence (SEQ ID NO:8) of the heavy chain variable region of the 11E6 human monoclonal antibody. The CDR1 (SEQ ID) NO:28), CDR2 (SEQ ID NO:38) and CDR3 (SEQ ID NO:48) regions are delineated and the V and J germline derivations are indicated.

FIG. 8B shows the nucleotide sequence (SEQ ID NO:98) and amino acid sequence (SEQ ID NO 18) of the light chain variable region of the 11E6 human monoclonal antibody. The CDR1 (SEQ ID NO:58), CDR2 (SEQ ID NO:68) and CDR3 (SEQ ID NO:78) regions are delineated and the V and J germline derivations are indicated.

FIG. 9A shows the nucleotide sequence (SEQ ID NO:89) and amino acid sequence (SEQ ID NO:9) of the heavy chain variable region of the 12B7 human monoclonal antibody. The CDR1 (SEQ ID NO:29), CDR2 (SEQ ID NO:39) and CDR3 (SEQ ID NO:49) regions are delineated and the V and J germline derivations are indicated.

FIG. 9B shows the nucleotide sequence (SEQ ID NO:99) and amino acid sequence (SEQ ID NO: 19) of the light chain variable region of the 12B7 human monoclonal antibody. The CDR1 (SEQ ID NO:59), CDR2 (SEQ ID NO:69) and CDR3 (SEQ ID NO:79) regions are delineated and the V and J germline derivations are Indicated.

FIG. 10A shows the nucleotide sequence (SEQ ID NO:90) and amino acid sequence (SEQ ID NO: 10) of the heavy chain variable region of the 13G4 human monoclonal antibody. The CDR1 (SEQ ID NO:30), CDR2 (SEQ ID NO:40) and CDR3 (SEQ ID NO:50) regions are delineated and the V and J germline derivations are indicated.

FIG. 10B shows the nucleotide sequence (SEQ ID NO:100) and amino acid sequence (SEQ ID NO:20) of the light chain variable region of the 13G4 human monoclonal antibody. The CDR1 (SEQ ID NO:60), CDR2 (SEQ ID NO:70) and CDR3 (SEQ ID NO:80) regions are delineated and the V and J germline derivations are indicated.

FIG. 11 shows the alignment of the amino acid sequence of the heavy chain variable region of 3G10 with the human germline $V_H$ 1-18 amino acid sequence (SEQ ID NO:101).

FIG. 12 shows the alignment of the amino acid sequence of the heavy chain variable region of 12A4 with the human germline $V_H$ 1-69 amino acid sequence (SEQ ID NO:102).

FIG. 13 shows the alignment of the amino acid sequence of the heavy chain variable region of 10A5 with the human germline $V_H$ 1-3 amino acid sequence (SEQ ID NO:103).

FIG. 14 shows the alignment of the amino acid sequence of the heavy chain variable region of 5F8 with the human germline $V_H$ 1-69 amino acid sequence (SEQ ID NO:102).

FIG. 15 shows the alignment of the amino acid sequence of the heavy chain variable region of 10H10 with the human germ line $V_H$ 3-9 amino acid sequence (SEQ ID NO:104).

FIG. 16 shows the alignment of the amino acid sequence of the heavy chain variable region of 1B12 with the human germline $V_H$ 1-69 amino acid sequence (SEQ ID NO:102).

FIG. 17 shows the alignment of the amino acid sequence of the heavy chain variable region of 7H1 with the human germline $V_H$ 1-69 amino acid sequence (SEQ ID NO:102).

FIG. 18 shows the alignment of the amino acid sequence of the heavy chain variable region of 11E6 with the human germline $V_H$ 1-69 amino acid sequence (SEQ ID NO-102).

FIG. 19 shows the alignment of the amino acid sequence of the heavy chain variable region of 12B7 with the human germline $V_H$ 1-69 amino acid sequence (SEQ ID NO: 102).

FIG. 20 shows the alignment of the amino acid sequence of the heavy chain variable region of 13G4 with the human germline $V_H$ 3-9 amino acid sequence (SEQ ID NO: 104).

FIG. 21 shows the alignment of the amino acid sequence of the light chain variable region of 3G10 with the human germline $V_k$ L6 amino acid sequence (SEQ ID NO:105).

FIG. 22 shows the alignment of the amino acid sequence of the light chain variable region of 12A4 with the human germline $V_k$ L6 amino acid sequence (SEQ ID NO:105).

FIG. 23 shows the alignment of the amino acid sequence of the light chain variable region of 10A5 with the human germline $V_k$ L15 amino acid sequence (SEQ ID NO:106).

FIG. 24 shows the alignment of the amino acid sequence of the light chain variable region of 5F8 with the human germline $V_k$ A27 amino acid sequence (SEQ ID NO: 107).

FIG. 25 shows the alignment of the amino acid sequence of the light chain variable region of 10H10 with the human germline $V_k$ L15 amino acid sequence (SEQ ID NO:106).

FIG. 26 shows the alignment of the amino acid sequence of the light chain variable region of 1B12 with the human germline $V_k$ L6 amino acid sequence (SEQ ID NO: 105).

FIG. 27 shows the alignment of the amino acid sequence of the light chain variable region of 7H1 with the human germline $V_k$ L6 amino acid sequence (SEQ ID NO:105).

FIG. 28 shows the alignment of the amino acid sequence of the light chain variable region of 11E6 with the human germline $V_k$ A27 amino acid sequence (SEQ ID NO:107).

FIG. 29 shows the alignment of the amino acid sequence of the light chain variable region of 11E6a (SEQ ID NO:109) with the human germline $V_k$ A27 amino acid sequence (SEQ ID NO:107).

FIG. 30 shows the alignment of the amino acid sequence of the light chain variable region of 12B7 with the human germline $V_k$ L6 amino acid sequence (SEQ ID NO:105).

FIG. 31 shows the alignment of the amino acid sequence of the light chain variable region of 13G4 with the human germline $V_k$ L18 amino acid sequence (SEQ ID NO:108).

FIG. 32A is a Flow cytometry plot for 3G10, FIG. 32B is a Flow cytometry plot for 10A5, and FIG. 32C is a Flow cytometry plot for 12A4.

FIGS. 37A-37C show the results of flow cytometry experiments demonstrating that the human monoclonal antibodies 3G10, 10A5, and 12A4, directed against human PD-L1, binds to PD-L1 on the cell surface of activated T cells. FIG. 37A is a Flow cytometry plot for 3G10, FIG. 37B is a Flow cytometry plot for 10A5, and FIG. 37C is a Flow cytometry plot for 12A4.

FIG. 39A is a bar graph showing concentration dependent T-cell proliferation using HuMAb 10A5; FIG. 39B is a bar graph showing concentration dependent IFN-γ secretion using HuMAb 10A5; FIG. 39C is a bar graph showing IFN-γ secretion using HuMAbs 3G10 and 12A4; FIG. 39D is a bar graph showing concentration dependent IL-2 secretion using HuMAb 10A5.

FIG. 41A is a bar graph showing concentration dependent T-cell proliferation using HuMAb 10A5; FIG. 41B is a bar graph showing concentration dependent IFN-γ secretion using HuMAb 10A5.

DETAILED DESCRIPTION

Figure 32:
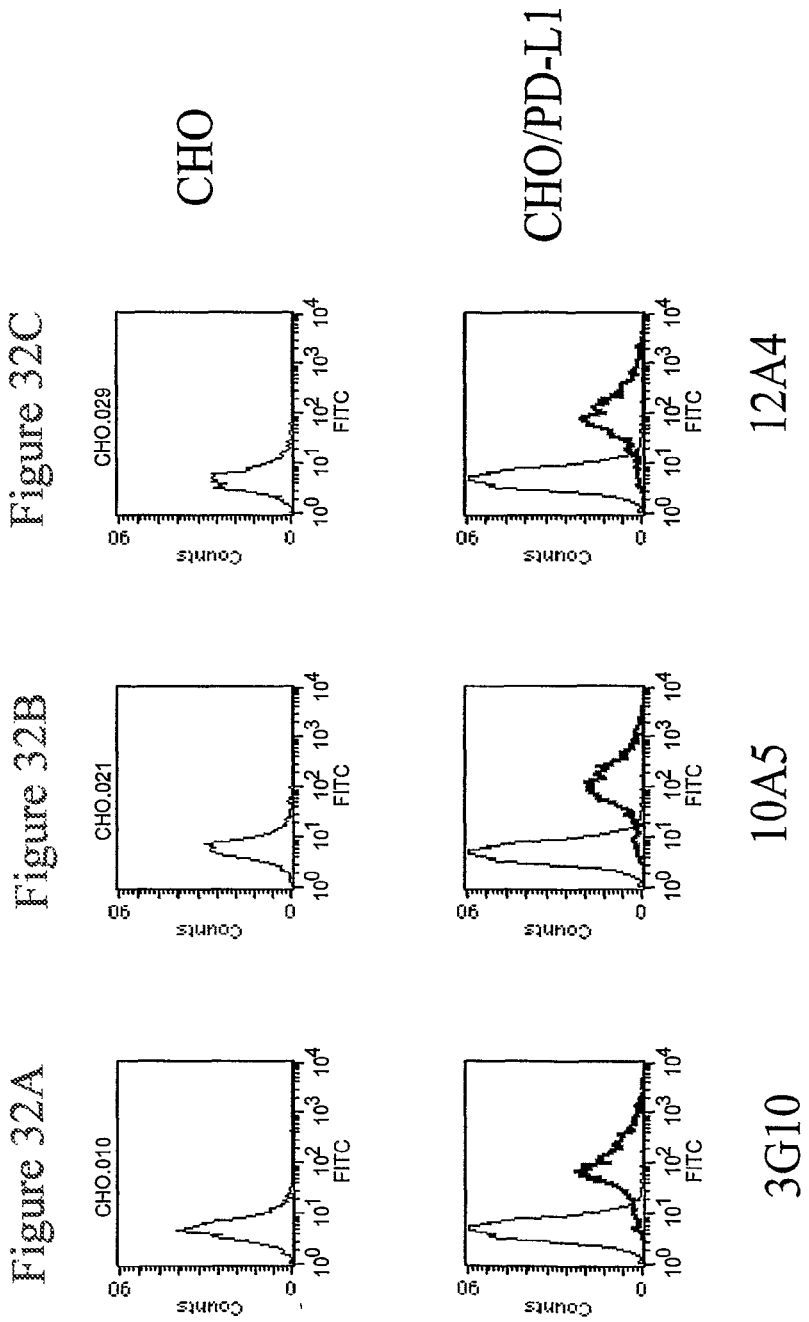
FIGS. 32A-32C show the results of flow cytometry experiments demonstrating that the human monoclonal antibodies 3G10, 10A5, and 12A4, directed against human PD-L1, binds the cell surface of CHO cells transfected with full-length human PD-L1.

In one aspect, the present disclosure relates to isolated monoclonal antibodies, particularly human monoclonal antibodies that bind specifically to PD-L1. In certain embodiments, the antibodies of the invention exhibit one or more desirable functional properties, such as high affinity binding to PD-L1, the ability to augment T cell proliferation, IFN-γ and/or IL-2 secretion in mixed lymphocyte reactions, the ability to inhibit binding of PD-L1 to the PD-1 receptor, the ability to stimulate antibody responses and/or the ability to reverse the suppressive function of T regulatory cells. Additionally or alternatively, the antibodies of the invention are derived from particular heavy and light chain germline sequences and/or comprise particular structural features such as CDR regions comprising particular amino acid sequences.

The instant disclosure provides, for example, isolated antibodies, methods of making such antibodies, immunoconjugates and bispecific molecules comprising such antibodies and pharmaceutical compositions containing the antibodies, immunconjugates or bispecific molecules of the invention.

In another aspect, the disclosure pertains to methods of inhibiting growth of tumor cells in a subject using anti-PD-L1 antibodies. The invention also relates to methods of using the antibodies to modify an immune response, as well as to treat diseases such as cancer or infectious disease, or to stimulate a protective autoimmune response or to stimulate antigen-specific immune responses (e.g., by coadministration of anti-PD-L1 with an antigen of interest).

In order that the present disclosure may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the PD-L1 receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: PR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., PD-L). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); ea e.g., Bird et al. (1988) *Science* 22:423-426; and Huston et al. (1988) *Proc. Natl. Acad Set. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds PD-L1 is substantially free of antibodies that specifically bind antigens other than PD-L1). An isolated antibody that specifically binds PD-L1 may, however, have cross-reactivity to other antigens, such as PD-L1 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies awe sequences that, while derived from and related to human germline $V_n$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human PD-L1" is Intended to refer to an antibody that binds to human PD-L1 with a $K_D$ of $1 \times 10^{-7}$ M or less, more preferably $5 \times 10^{-8}$ M or less, more preferably $1 \times 10^{-8}$ M or less, more preferably $5 \times 10^{-9}$ M or less, even more preferably between $1 \times 10^{-8}$ M and $1 \times 10^{-10}$ M or less.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as, used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

Various aspects of the disclosure are described in further detail in the following subsections.

Anti-PD-L1 Antibodies

The antibodies of the invention are characterized by particular functional features or properties of the antibodies. For example, the antibodies bind specifically to human PD-L1. Preferably, an antibody of the invention binds to PD-L1 with high affinity, for example with a $K_D$ of $1 \times 10^{-7}$ M or less. The anti-PD-L1 antibodies of the invention preferably exhibit one or more of the following characteristics:

(a) binds to human PD-L1 with a $K_D$ of $1 \times 10^{-7}$ M or less;
(b) increases T-cell proliferation in a mixed lymphocyte reaction (MLR) assay;
(c) increases interferon-γ production in an MLR assay;
(d) increases IL-2 secretion in an MLR assay
(e) stimulates antibody responses; and/or
(f) reverses the effect of T regulatory cells on T cell effector cells and/or dendritic cells.

Preferably, the antibody binds to human PD-L1 with a $K_D$ of $5 \times 10^{-8}$ M or less, binds to human PD-L1 with a $K_D$ of $1 \times 10^{-8}$ M or less, binds to human PD-L1 with a $K_D$ of $5 \times 10^{-9}$ M or less, binds to human PD-L1 with a $K_D$ of $4 \times 10^{-9}$ M or less, binds to human PD-L1 with a $K_D$ of $2 \times 10^{-9}$ M or less, or binds to human PD-L1 with a $K_D$ of between $1 \times 10^{-9}$ M and $1 \times 10^{-10}$ M or less.

Standard assays to evaluate the binding ability of the antibodies toward PD-L1 are known in the art, including for example, ELISAs, Western blots and RIAs. Suitable assays are described in detail in the Examples. The binding kinetics (e.g., binding affinity) of the antibodies also can be assessed by standard assays known in the art, such as by Biacore® analysis.

Monoclonal Antibodies 3G10, 12A4, 10A5, 5F8, 10H10, 1B12, 11E6, 12B7, and 13G4.

Preferred antibodies of the invention are the human monoclonal antibodies 30G10, 12A4, 10A5, 5F8, 10H10, 1B12, 7H1, 11E6, 12B7, and 13G4, isolated and structurally characterized as described in Examples 1 and 2. The $V_H$ amino acid sequences of 3G10, 12A4, 10A5, 5F8, 10H10, 1B12, 7H1, 11E6, 12B7, and 13G4 are shown in SEQ ID NOs:1, 2, 3, 4, 5, 6, 7, 8, 9, and 10, respectively. The $V_L$ amino acid sequences of 3G10, 12A4, 10A5, 5F8, 10H10, 1B12, 7H1, 11E6, 12B7, and 13G4 are shown in SEQ ID NOs:11, 12, 13, 14, 15, 16, 17, 18, 19, and 20, respectively.

Given that each of these antibodies can bind to PD-L1, the $V_H$ and $V_L$ sequences can be "mixed and matched" to create other anti-PD-L1 binding molecules of the invention. PD-L1 binding of such "mixed and matched" antibodies can be tested using the binding assays described above and in the Examples (e.g., ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, the invention provides an isolated monoclonal antibody, or antigen binding portion thereof comprising:

(a) a heavy chain variable region comprising an amino acid sequence selected from the group consisting of SEQ ID NOs:1, 2, 3, 4, 5, 6, 7, 8, 9, and 10; and (b) a light chain variable region comprising an amino acid sequence selected from the group consisting of SEQ ID NOs:11, 12, 13, 14, 15, 16, 17, 18, 19, and 20;

wherein the antibody specifically binds PD-L1, preferably human PD-L1.

Preferred heavy and light chain combinations include:
(a) a heavy chain variable region comprising the amino acid sequence of SEQ ID NO:1; and (b) a light chain variable region comprising the amino acid sequence of SEQ ID NO:11; or
(a) a heavy chain variable region comprising the amino acid sequence of SEQ ID NO:2; and (b) a light chain variable region comprising the amino acid sequence of SEQ ID NO:12; or
(a) a heavy chain variable region comprising the amino acid sequence of SEQ ID NO:3; and (b) a light chain variable region comprising the amino acid sequence of SEQ ID NO:13; or
(a) a heavy chain variable region comprising the amino acid sequence of SEQ ID NO:4; and (b) a light chain variable region comprising the amino acid sequence of SEQ ID NO:14; or
(a) a heavy chain variable region comprising the amino acid sequence of SEQ ID NO:5; and (b) a light chain variable region comprising the amino acid sequence of SEQ ID NO:15; or
(a) a heavy chain variable region comprising the amino acid sequence of SEQ ID NO:6; and (b) a light chain variable region comprising the amino acid sequence of SEQ ID NO:16; or
(a) a heavy chain variable region comprising the amino acid sequence of SEQ ID NO:7; and (b) a light chain variable region comprising the amino acid sequence of SEQ ID NO:17; or
(a) a heavy chain variable region comprising the amino acid sequence of SEQ ID NO:8; and (b) a light chain variable region comprising the amino acid sequence of SEQ ID NO:18; or
(a) a heavy chain variable region comprising the amino acid sequence of SEQ ID NO:9; and (b) a light chain variable region comprising the amino acid sequence of SEQ ID NO:19; or (a) a heavy chain variable region comprising the amino acid sequence of SEQ ID NO: 10; and (b) a light chain variable region comprising the amino acid sequence of SEQ ID NO:20.

In another aspect, the invention provides antibodies that comprise the heavy chain and light chain CDR1s, CDR2s and CDR3s of 3G10, 12A4, 10A5, 5F, 8, 10H10, 1B12, 7H1, 11E6, 12B7, and 13G4, or combinations thereof. The amino acid sequences of the $V_H$ CDR1s of 3G10, 12A4, 10A5, 5F81, 100, 1B12, 7H1, 11E6, 12B7, and 13G4 are shown in SEQ ID NOs:21, 22, 23, 24, 25, 26, 27, 28, 29, and 30, respectively. The amino acid sequences of the $V_H$ CDR2s of 3G10, 12A4, 10A5, 5F8, 10H10, 1B12, 7H1, 11B6, 12B7, and 13G4 are shown in SEQ ID NOs:31, 32, 33, 34, 35, 36, 37, 38, 39, and 40, respectively. The amino acid sequences of the $V_H$ CDR3s of 3G1, 12A4, 10A5, 5F8, 10H10, 1B12, 7H1, 11E6, 12B7, and 13G4 are shown in SEQ ID NOs:41, 42, 43, 44, 45, 46, 47, 48, 49, and 50, respectively. The amino acid sequences of the $V_k$ CDR1s of 3G10, 12A4, 10A5, 5F8, 10H0, 1B12, 7H11, 11E6, 12B7, and 13G4 are shown in SEQ ID NOs:51, 52, 53, 54, 55, 56, 57, 58, 59, and 60, respectively. The amino acid sequences of the $V_k$ CDR2s of 3G10, 12A4, 10A5, 5F8, 10H10, 1B12, 7H1, 11E6, 12B7, and 13G4 are shown in SEQ ID NOs:61, 62, 63, 64, 65, 66, 67, 68, 69, and 70, respectively. The amino acid sequences of the $V_k$ CDR3s of 3G10, 12A4, 10A5, 5F8, 10H10, 1B12, 7H1, 11E6, 12B7, and 13G4 are shown in SEQ ID NOs:71, 72, 73, 74, 75, 76, 77, 78, 79, and 80, respectively. The CDR regions are delineated using the Kabat system (Kabat, B. A., et al. (1991) Sequences of Proteins of Immunological Interest, Fifth Edition, U.S. Department of Health and Human Services, NIH Publication No. 91-3242).

Given that each of these antibodies can bind to PD-L1 and that antigen-binding specificity is provided primarily by the CDR1, CDR2, and CDR3 regions, the $V_H$ CDR1, CDR2, and CDR3 sequences and $V_k$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_k$ CDR1, CDR2, and CDR3) to create other anti-PD-L1 binding molecules of the invention. PD-L1 binding of such "mixed and matched" antibodies can be tested using the binding assays described above and in the Examples (e.g., ELISAs, Biacore analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular V sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies antibodies 3G10, 12A4, 10A5, 5F8, 10H10, 1B12, 7H1, 11E6, 12B7, and 13G4.

Accordingly, in another aspect, the invention provides an isolated monoclonal antibody, or antigen binding portion thereof comprising:

(a) a heavy chain variable region CDR1 comprising an amino acid sequence selected from the group consisting of SEQ ID NOs:21, 22, 23, 24, 25, 26, 27, 28, 29, and 30;

(b) a heavy chain variable region CDR2 comprising an amino acid sequence selected from the group consisting of SEQ ID NOs:31, 32, 33, 34, 35, 36, 37, 38, 39, and 40;

(c) a heavy chain variable region CDR3 comprising an amino acid sequence selected from the group consisting of SEQ ID NOs:41, 42, 43, 44, 45, 46, 47, 48, 49, and 50;

(d) a light chain variable region CDR1 comprising an amino acid sequence selected from the group consisting of SEQ ID NOs:51, 52, 53, 54, 55, 56, 57, 58, 59, and 60;

(e) a light chain variable region CDR2 comprising an amino acid sequence selected from the group consisting of SEQ ID NOs:61, 62, 63, 64, 65, 66, 67, 68, 69, and 70; and (f) a light chain variable region CDR3 comprising an amino acid sequence selected from the group consisting of SEQ ID NOs:71, 72, 73, 74, 75, 76, 77, 78, 79, and 80;

wherein the antibody specifically binds PD-L1, preferably human PD-L1.

In a preferred embodiment, the antibody comprises:

(a) a heavy chain variable region CDR1 comprising SEQ ID NO:21;

(b) a heavy chain variable region CDR2 comprising SEQ ID NO:31;

(c) a heavy chain variable region CDR3 comprising SEQ ID NO:41;

(d) a light chain variable region CDR1 comprising SEQ ID NO:51;

(c) a light chain variable region CDR2 comprising SEQ ID NO:61; and (f) a light chain variable region CDR3 comprising SEQ ID NO:71.

In another preferred embodiment the antibody comprises:

(a) a heavy chain variable region CDR1 comprising SEQ ID NO:22;

(b) a heavy chain variable region CDR2 comprising SEQ ID NO:32;

(c) a heavy chain variable region CDR3 comprising SEQ ID NO:42;

(d) a light chain variable region CDR1 comprising SEQ ID NO:52;

(e) a light chain variable region CDR2 comprising SEQ ID NO:62; and (f) a light chain variable region CDR3 comprising SEQ ID NO:72.

In another preferred embodiment the antibody comprises:

(a) a heavy chain variable region CDR1 comprising SEQ ID NO:23;

(b) a heavy chain variable region CDR2 comprising SEQ ID NO:33;

(c) a heavy chain variable region CDR3 comprising SEQ ID NO:43;

(d) a light chain variable region CDR1 comprising SEQ ID NO:53;

(e) a light chain variable region CDR2 comprising SEQ ID NO:63; and (f) a light chain variable region CDR3 comprising SEQ ID NO:73.

In another preferred embodiment the antibody comprises:

(a) a heavy chain variable region CDR1 comprising SEQ ID NO:24;

(b) a heavy chain variable region CDR2 comprising SEQ ID NO:34;

(c) a heavy chain variable region CDR3 comprising SEQ ID NO:44;

(d) a light chain variable region CDR1 comprising SEQ ID NO:54;

(e) a light chain variable region CDR2 comprising SEQ ID NO:64; and (f) a light chain variable region CDR3 comprising SEQ ID NO:74.

In another preferred embodiment the antibody comprises:
(a) a heavy chain variable region CDR1 comprising SEQ ID NO:25;
(b) a heavy chain variable region CDR2 comprising SEQ ID NO:35;
(c) a heavy chain variable region CDR3 comprising SEQ ID NO:45;
(d) a light chain variable region CDR1 comprising SEQ ID NO:55;
(e) a light chain variable region CDR2 comprising SEQ ID NO:65; and
(f) a light chain variable region CDR3 comprising SEQ ID NO:75.

In another preferred embodiment the antibody comprises:
(a) a heavy chain variable region CDR1 comprising SEQ ID NO:26;
(b) a heavy chain variable region CDR2 comprising SEQ ID NO:36;
(c) a heavy chain variable region CDR3 comprising SEQ ID NO:46;
(d) a light chain variable region CDR1 comprising SEQ ID NO:56;
(e) a light chain variable region CDR2 comprising SEQ ID NO:66; and
(f) a light chain variable region CDR3 comprising SEQ ID NO:76.

In another preferred embodiment the antibody comprises:
(a) a heavy chain variable region CDR1 comprising SEQ ID NO:27;
(b) a heavy chain variable region CDR2 comprising SEQ ID NO:37;
(c) a heavy chain variable region CDR3 comprising SEQ ID NO:47;
(d) a light chain variable region CDR1 comprising SEQ ID NO:57;
(e) a light chain variable region CDR2 comprising SEQ ID NO:67; and
(f) a light chain variable region CDR3 comprising SEQ ID NO:77.

In another preferred embodiment the antibody comprises:
(a) a heavy chain variable region CDR1 comprising SEQ ID NO:28;
(b) a heavy chain variable region CDR2 comprising SEQ ID NO:38;
(c) a heavy chain variable region CDR3 comprising SEQ ID NO:48;
(d) a light chain variable region CDR1 comprising SEQ ID NO:58;
(e) a light chain variable region CDR2 comprising SEQ ID NO:68; and
(f) a light chain variable region CDR3 comprising SEQ ID NO:78.

In another preferred embodiment the antibody comprises:
(a) a heavy chain variable region CDR1 comprising SEQ ID NO:29;
(b) a heavy chain variable region CDR2 comprising SEQ ID NO:39;
(c) a heavy chain variable region CDR3 comprising SEQ ID NO:49;
(d) a light chain variable region CDR1 comprising SEQ ID NO:59;
(e) a light chain variable region CDR2 comprising SEQ ID NO:69; and
(f) a light chain variable region CDR3 comprising SEQ ID NO:79.

In another preferred embodiment the antibody comprises:
(a) a heavy chain variable region CDR1 comprising SEQ ID NO:30;
(b) a heavy chain variable region CDR2 comprising SEQ ID NO:40;
(c) a heavy chain variable region CDR3 comprising SEQ ID NO:50;
(d) a light chain variable region CDR1 comprising SEQ ID NO:60;
(e) a light chain variable region CDR2 comprising SEQ ID NO:70; and
(f) a light chain variable region CDR3 comprising SEQ ID NO:80.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer at al., *J. Mol. Biol.* 26:833-849 (2000) (describing recombinant epithelial glycoprotein-2 (EGP-2) antibodies using only the heavy chain CDR3 sequence of the parental murine MOC-31 anti-EGP-2 antibody); Rader at al., *Proc. Natl. Acad Sa. U.S.A.* 9:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent muring antibody with affinities as high or higher than the parent murine antibody); Barbas at al., *J. Am. Chem. Soc.* 116:2161-2162 (1994) (disclosing that the CDR3 domain provides the most significant contribution to antigen binding); Barbas at al., *Proc. Natl. Acad. Sci. U.S.A.* 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., *J Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, within certain aspects, the present invention provides monoclonal antibodies comprising one or more heavy and/or light chain CDR3 domain from a non-human antibody, such as a mouse or rat antibody, wherein the monoclonal antibody is capable of specifically binding to PD-L1. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present invention provides monoclonal antibodies comprising one or more heavy and/or light chain CDR3 domain from a first human antibody, such as, for example, a human antibody obtained from a non-human animal, wherein the first human antibody is capable of specifically binding to PD-L1 and wherein the CDR3 domain from the first human antibody replaces a CDR3 domain in a human antibody that is lacking binding specificity for PD-L1 to generate a second human antibody that is capable of specifically binding to PD-L1. Within some embodiments, antibodies of the instant disclosure comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated monoclonal antibody, or an antigen-binding portion thereof comprising a heavy chain variable region that is the product of or derived from a human $V_H$ 1-18 gene, wherein the antibody specifically binds PD-L1. In another preferred embodiment, the invention provides an isolated monoclonal antibody, or an antigen-binding portion thereof comprising a heavy chain variable region that is the product of or derived from a human $V_H$ 1-69 gene, wherein the antibody specifically binds PD-L1. In another preferred embodiment, the invention provides an isolated monoclonal antibody, or an antigen-binding portion thereof comprising a heavy chain variable region that is the product of or derived from a human $V_H$ 1-3 gene, wherein the antibody specifically binds PD-L1. In another preferred embodiment, the invention provides an isolated monoclonal antibody, or an antigen-binding portion thereof, comprising a heavy chain variable region that is the product of or derived from a human $V_H$ 3-9 gene, wherein the antibody specifically binds PD-L1. In yet another preferred embodiment, the invention provides an isolated monoclonal antibody, or an antigen-binding portion thereof, comprising a light chain variable region that is the product of or derived from a human $V_K$ L6 gene, wherein the antibody specifically binds PD-L1. In yet another preferred embodiment, the invention provides an isolated monoclonal antibody, or an antigen-binding portion thereof, comprising a light chain variable region that is the product of or derived from a human $V_K$ L15 gene, wherein the antibody specifically binds PD-L1. In yet another preferred embodiment, the invention provides an isolated monoclonal antibody, or an antigen-binding portion thereof comprising a light chain variable region that is the product of or derived from a human $V_K$ A27 gene, wherein the antibody specifically binds PD-L1. In yet another preferred embodiment, the invention provides an isolated monoclonal antibody, or an antigen-binding portion thereof comprising a light chain variable region that is the product of or derived from a human $V_K$ L18 gene, wherein the antibody specifically binds PD-L1. In yet another preferred embodiment, the invention provides an isolated monoclonal antibody, or antigen-binding portion thereof, wherein the antibody:

(a) comprises a heavy chain variable region that is the product of or derived from a human $V_H$ 1-18, 1-69, 1-3 or 3-9 gene (which encodes the amino acid sequences set forth in SEQ ID NOs:101, 102, 103 and 104, respectively);

(b) comprises a light chain variable region that is the product of or derived from a human $V_K$ L6, L15, A27 or L18 gene (which encodes the amino acid sequences set forth in SEQ ID NOs:105, 106, 107 and 108, respectively); and (c) specifically binds to PD-L1, preferably human PD-L1.

An example of an antibody having $V_H$ and $V_K$ of $V_H$ 1-18 and $V_K$ L6, respectively, is 3G10. Examples of antibodies having $V_H$ and $V_K$ of $V_H$ 1-69 and $V_K$ L6, respectively, 12A4, 1B12, 7H1, and 12B7. An example of an antibody having $V_H$ and $V_K$ of $V_H$ 1-3 and $V_K$ L15, respectively, is 10A5. Examples of antibodies having $V_H$ and $V_K$ of $V_H$ 1-69 and $V_K$ A27, respectively, are 5F8, 11E6 and 11B6a. An example of an antibody having $V_R$ and $V_K$ of $V_H$ 3-9 and $V_K$ L15, respectively, is 10H10. An example of an antibody having $V_H$ and $V_K$ of $V_H$ 1-3 and $V_K$ L15, respectively, is 10A5. An example of an antibody having $V_H$ and $V_K$ of $V_H$ 3-9 and $V_K$ L18, respectively, is 13G4.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (I.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody is generally at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. In certain embodiments, a human antibody derived from a particular human germline sequence will display no more than 10 amino acid differences from the amino acid sequence encoded by the human germline immunoglobulin gene. In certain other embodiments, the human antibody may display no more than 5, or even no more than 4, 3, 2, or 1 amino acid difference from the amino acid sequence encoded by the germline immunoglobulin gone.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-PD-L1 antibodies of the invention.

For example, the invention provides an isolated monoclonal antibody, or antigen binding portion thereof comprising a heavy chain variable region and a light chain variable region, wherein:

(a) the heavy chain variable region comprises an amino acid sequence that is at least 80% homologous to an amino acid sequence selected from the group consisting of SEQ ID NOs:1, 2, 3, 4, 5, 6, 7, 8, 9, and 10;

(b) the light chain variable region comprises an amino acid sequence that is at least 80% homologous to an amino acid sequence selected from the group consisting of SEQ ID NOs:11, 12, 13, 14, 15, 16, 17, 18, 19, and 20;

(c) the antibody binds to human PD-L1 with a $K_D$ of $1\times10^{-7}$ M or less;

(d) the antibody increases T-cell proliferation in a mixed lymphocyte reaction (MLR) assay;

(e) the antibody increases interferon-γ production in an MLR assay;

(f) the antibody increases IL-2 secretion in an MLR assay, (g) the antibody stimulates antibody responses; and (h) reverses the effect of T regulatory cells on T cell effector cells and/or dendritic cells.

In other embodiments, the $V_H$ and/or $V_L$ amino acid sequences may be 85% 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs:25, 26, 27, 28, 29, and 30, followed by testing of the encoded altered antibody for retained function (I.e., the functions set forth in (c) through (h) above) using the functional assays described herein.

As used herein, the percent homology between two amino acid sequences is equivalent to the percent identity between the two sequences. The percent identity between the two sequences is function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.,* 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

In certain instances, the protein sequences of the present disclosure can be further used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 21(17):3389-3402. When utilizing BLAST and Gapped BLAST programs, the default parameters of the respective programs (e.g., XBLAST and NBLAST) can be used. See www.ncbi.nlm.nih.gov.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 3G10, 12A4, 10A5, 5F8, 10H10, 1B12, 7H1, 11E6, 12B7 or 13G4), or conservative modifications thereof, and wherein the antibodies retain the desired functional properties of the anti-PD-L1 antibodies of the invention. Accordingly, the invention provides an isolated monoclonal antibody, or antigen binding portion thereof; comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs:41, 42, 43, 44, 45, 46, 47, 48, 49, and 50, and conservative modifications thereof;

(b) the light chain variable region CDR3 sequence comprises an amino acid sequence selected from the group consisting of amino acid sequence of SEQ ID NOs:71, 72, 73, 74, 75, 76, 77, 78, 79, and 80, and conservative modifications thereof, (c) the antibody binds to human PD-L1 with a $K_D$ of $1\times10^{-7}$ M or less;

(d) the antibody increases T-cell proliferation in a mixed lymphocyte reaction (MLR) assay;

(e) the antibody increases interferon-γ production in an MLR assay;

(f) the antibody increases IL-2 secretion in an MLR assay (g) the antibody stimulates antibody responses; and (h) reverses the effect of T regulatory cells on T cell effector cells and/or dendritic cells.

In a preferred embodiment, the heavy chain variable region CDR2 sequence comprises an amino acid sequence selected from the group consisting of amino acid sequences of SEQ ID NOs:31, 32, 33, 34, 35, 36, 37, 38, 39, and 40, and conservative modifications thereof; and the light chain variable region CDR2 sequence comprises an amino acid sequence selected from the group consisting of amino acid sequences of SEQ ID NOs:61, 62, 63, 64, 65, 66, 67, 68, 69, and 70, and conservative modifications thereof. In another preferred embodiment, the heavy chain variable region CDR1 sequence comprises an amino acid sequence selected from the group consisting of amino acid sequences of SEQ ID NOs:21, 22, 23, 24, 25, 26, 27, 28, 29, and 30, and conservative modifications thereof; and the light chain variable region CDR1 sequence comprises an amino acid sequence selected from the group consisting of amino acid sequences of SEQ ID NOs:51, 52, 53, 54, 55, 56, 57, 58, 59, and 60, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (h) above) using the functional assays described herein.

Antibodies that Bind to the Same Epitope as Anti-PD-L1 Antibodies of the Invention In another embodiment, the invention provides antibodies that bind to the same epitope on human PD-L1 as any of the PD-L1 monoclonal antibodies of the invention (i.e., antibodies that have the ability to cross-compete for binding to PD-L1 with any of the monoclonal antibodies of the invention). In preferred embodiments, the reference antibody for cross-competition studies can be the monoclonal antibody 3G10 (having $V_H$ and $V_L$ sequences as shown in SEQ ID NOs:1 and 11, respectively), or the monoclonal antibody 12A4 (having $V_H$ and $V_L$ sequences as shown in SEQ ID NOs:2 and 12, respectively), or the monoclonal antibody 10A5 (having $V_H$ and $V_L$ sequences as shown in SEQ ID NOs:3 and 13, respectively), or the monoclonal antibody 10A5 (having $V_H$ and $V_L$ sequences as shown in SEQ ID NOs:3 and 13, respectively), or the monoclonal antibody 5F8 (having $V_H$ and $V_L$ sequences as shown in SEQ ID NOs:4 and 14, respectively), or the monoclonal antibody 10H10 (having $V_H$ and $V_L$ sequences as shown in SEQ ID NOs:5 and 15, respectively), or the monoclonal antibody 1B12 (having $V_H$ and $V_L$ sequences as shown in SEQ ID NOs:6 and 16, respectively), or the monoclonal antibody 7H1 (having $V_H$ and $V_L$ sequences as shown in SEQ ID NOs:7 and 17, respectively), or the monoclonal antibody 11E6 (having $V_H$ and $V_L$ sequences as shown in SEQ ID NOs:8 and 18, respectively), or the monoclonal antibody 12B7 (having $V_H$ and $V_L$ sequences as shown in SEQ ID NOs:9 and 19, respectively), or the monoclonal antibody 13G4 (having $V_H$ and $V_L$ sequences as shown in SEQ ID NOs:10 and 20, respectively). Such cross-competing antibodies can be identified based on their ability to cross-compete with 3G10, 12A4, 10A5, 5F8, 10H10, 1B12, 7H1, 11E6, 12B7 or 13G4 in standard PD-L1, binding assays. For example, BIAcore analysis, ELISA assays or flow cytometry may be used to demonstrate cross-competition with the antibodies of the current invention. The ability of a test antibody to inhibit the binding of, for example, 3G10, 12A4, 10A5, 5F8, 10H10, 1B12, 7H1, 11E6, 12B7 or 13G4, to human PD-L1 demonstrates that the test antibody can compete with 3G10, 12A4, 10A5, 5F8, 10H10, 1B12, 7H1, 11E6, 12B7 or 13G4 for binding to human PD-L1 and thus binds to the same epitope on human PD-L1 as 3G10, 12A4, 10A8, 10H10, 1B12, 7H1, 11E6, 12B7 or 13G4. In a preferred embodiment, the antibody that binds to the same epitope on human PD-L1 as 3G10, 12A4, 10A5, 5F8, 10H10, 1B12, 7H1, 11E6, 12B7 or 13G4 is a human monoclonal antibody. Such human monoclonal antibodies can be prepared and isolated as described in the Examples.

Engineered and Modified Antibodies

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 32:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.) Accordingly, another embodiment of the invention pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs:21, 22, 23, 24, 25, 26, 27, 28, 29, and 30, SEQ ID NOs:31, 32, 33, 34, 35, 36, 37, 38, 39, and 40, and SEQ ID NOs:41, 42, 43, 44, 45, 46, 47, 48, 49, and 50, respectively, and a light chain variable region comprising CDR1, CDR2, and CDR3 sequences comprising an amino acid sequence selected from the group consisting of SEQ ID NOs:51, 52, 53, 54, 55, 56, 57, 58, 59, and 60, SEQ ID NOs:61, 62, 63, 64, 65, 66, 67, 68, 69, and 70, and SEQ ID NOs:71, 72, 73, 74, 75, 76, 77, 78, 79, and 80, respectively. Thus, such antibodies contain the $V_H$ and $V_L$ CDR sequences of monoclonal antibodies 3G10, 12A4, 10A5, 5F8, 10H10, 1B12, 7H1, 11E6, 12B7 or 13G4 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A, et al. (1991) Sequences of Proteins of Immunological Interest, Fifth Edition, U.S. Department of Health and Human Services, NIH Publication No. 91-3242; Tomlinson, I. M, et al. (1992) "The Repertoire of Human Germline $V_H$ Sequences Reveals about Fifty Groups of VS Segments with Different Hypervariable Loops" J. Mol. Biol. 227:776-798; and Cox, J. P. L et al. (1994) "A Directory of Human Germ-line $V_H$ Segments Reveals a Strong Bias in their Usage" Eur. J. Immunol. 24:827-836; the contents of each of which are expressly incorporated herein by reference.

Antibody protein sequences are compared against a compiled protein sequence database using one of the sequence similarity searching methods called the Gapped BLAST (Altschul et al. (1997) *Nucleic Acids Research* 2:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (vbase.mrc-cpe.cam.ac.uk/vbase/list2.php) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter which is turned off and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx. This translates the antibody sequence in all six frames and compares those translations to the VBASE nucleotide sequences dynamically translated in all six frames.

The identities are exact amino acid matches between the antibody sequence and the protein database over the entire length of the sequence. The positives (identities+ substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of the invention are those that are structurally similar to the framework sequences used by selected antibodies of the invention, e.g., similar to the $V_H$ 1-18 framework sequences (SEQ ID NO:101) and/or the $V_H$ 1-69 framework sequences (SEQ ID NO: 102) and/or the $V_H$ 1-3 framework sequences (SEQ ID NO:103) and/or the $V_H$ 3-9 framework sequences (SEQ ID NO: 104) and/or the $V_K$ L6 framework sequences (SEQ ID NO:105) and/or the $V_K$ L15 framework sequences (SEQ ID NO:106) and/or the $V_K$ A27 framework sequences (SEQ ID NO:107) and/or the $V_K$ L18 framework sequences (SEQ ID NO: 107) used by preferred monoclonal antibodies of the invention. The V CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides isolated anti-PD-L1 monoclonal antibodies, or antigen binding portions thereof comprising a heavy chain variable region comprising: (a) a $V_H$ CDR1 region comprising an amino acid sequence selected from the group consisting of SEQ ID NOs:21, 22, 23, 24, 25, 26, 27, 28, 29, and 30, or an amino acid sequence having one, two, three, four or five amino acid substitutions, deletions or additions as compared to SEQ ID NOs:21, 22, 23, 24, 25, 26, 27, 28, 29, and 30; (b) a $V_H$ CDR2 region comprising an amino acid sequence selected from the group consisting of SEQ ID NOs:31, 32, 33, 34, 35, 36, 37, 38, 39, and 40, or an amino acid sequence having one, two, three, four or five amino acid substitutions, deletions or additions as compared to SEQ ID NOs:31, 32, 33, 34, 35, 36, 37, 38, 39, and 40; (c) a $V_H$ CDR3 region comprising an amino acid sequence selected from the group consisting of SEQ ID NOs:41, 42, 43, 44, 45, 46, 47, 48, 49, and 50, or an amino acid sequence having one, two, three, four or five amino acid substitutions, deletions or additions as compared to SEQ ID NOs:41, 42, 43, 44, 45, 46, 47, 48, 49, and 50; (d) a $V_K$ CDR1 region comprising an amino acid sequence selected from the group consisting of SEQ ID NOs:51, 52, 53, 54, 55, 56, 57, 58, 59, and 60, or an amino acid sequence having one, two, three, four or five amino acid substitutions, deletions or additions as compared to SEQ ID NOs:51, 52, 53, 54, 55, 56, 57, 58, 59, and 60; (e) a $V_K$ CDR2 region comprising an amino acid sequence selected from the group consisting of SEQ ID NOs:61, 62, 63, 64, 65, 66, 67, 68, 69, and 70, or an amino acid sequence having one, two, three, four or five amino acid substitutions, deletions or additions as compared to SEQ ID NOs:61, 62, 63, 64, 65, 66, 67, 68, 69, and 70; and (f) a $V_K$ CDR3 region comprising an amino acid sequence selected from the group consisting of SEQ ID NOs:71, 72, 73, 74, 75, 76, 77, 78, 79, and 80, or an amino acid sequence having one, two, three, four or five amino acid substitutions, deletions or additions as compared to SEQ ID NOs:71, 72, 73, 74, 75, 76, 77, 78, 79, and 80.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. For example, as described below, a number of amino acid changes in the framework regions of the anti-PD-L1 antibodies 3G10, 12A4, 10A5, 5F8, 10H10, 1B12, 7H1, 11E6, 12B7 and 13G4 that differ from the parent germline sequence. To return the framework region sequences to their germline configuration, the somatic mutations can be "backmutated" to the germline sequence by, for example, site-directed mutagenesis or PCR-mediated mutagenesis. The alignment of the $V_H$ region for 3G10 against the parent germline $V_H$ 1-18 sequence is shown in FIG. 11. The alignment of the $V_H$ region for 12A4 against the parent germline $V_H$ 1-69 sequence is shown in FIG. 12. The alignment of the $V_H$ region for 10A5 against the parent germline $V_H$ 1-3 sequence is shown in FIG. 13. The alignment of the $V_H$ region for 5F8 against the parent germline $V_H$ 1-69 sequence is shown in FIG. 14. The alignment of the $V_H$ region for 10H10 against the parent germline $V_H$ 3-9 sequence is shown in FIG. 15. The alignment of the $V_H$ region for 1B12 against the parent germline $V_H$ 1-69 sequence is shown in FIG. 16. The alignment of the $V_a$ region for 7H1 against the parent germline $V_H$ 1-69 sequence is shown in FIG. 17. The alignment of the $V_H$ region for 11E6 against the parent germline $V_H$ 1-69 sequence is shown in FIG. 18. The alignment of the Via region for 12B7 against the parent germline $V_H$ 1-69 sequence is shown in FIG. 19. The alignment of the $V_H$ region for 13G4 against the parent germline $V_H$ 3-9 sequence is shown in FIG. 20.

For example, for 3G10, amino acid residue #79 (within FR3) of $V_H$ is a valine whereas this residue in the corresponding $V_H$ 1-18 germline sequence is an alanine. To return the framework region sequences to their germline configuration, the somatic mutations can be "backmutated" to the germline sequence by, for example, site-directed mutagenesis or PCR-mediated mutagenesis (e.g., residue #79 (residue #13 of FR3) of the $V_H$ of 3G10 can be "backmutated" from valine to alanine).

As another example, for 12A4, amino acid residue #24 (within FR1) of $V_H$ is a threonine whereas this residue in the corresponding $V_H$ 1-69 germline sequence is an alanine. To return the framework region sequences to their germline configuration, for example, residue #24 of the $V_H$ of 12A4 can be "backmutated" from threonine to alanine. Such "backmutated" antibodies are also intended to be encompassed by the invention.

As another example, for 12A4, amino acid residue #27 (within FR1) of $V_H$ is an aspartic acid whereas this residue in the corresponding $V_H$ 1-69 germline sequence is a glycine. To return the framework region sequences to their germline configuration, for example, residue #27 of the $V_H$ of 12A4 can be "backmutated" from aspartic acid to glycine. Such "backmutated" antibodies are also intended to be encompassed by the invention.

As another example, for 12A4, amino acid residue #95 (within FR3) of $V_H$ is a phenylalanine whereas this residue in the corresponding $V_H$ 1-69 germline sequence is a tyrosine. To return the framework region sequences to their germline configuration, for example, residue #95 (residue #29 of PR3) of the $V_H$ of 12A4 can be "backmutated" from phenylalanine to tyrosine. Such "backmutated" antibodies are also intended to be encompassed by the invention.

As another example, for 5F8, amino acid residue #24 (within FR1) is a valine whereas this residue in the corresponding $V_H$ 1-69 germline sequence is an alanine. To return the framework region sequences to their germline configuration, for example, residue #24 of the $V_H$ of 5F8 can be "backmutated" from valine to alanine. Such "backmutated" antibodies are also intended to be encompassed by the invention.

As another example, for 5F8, amino acid residue #28 (within FR1) is an isoleucine whereas this residue in the corresponding $V_H$ 1-69 germline sequence is an threonine. To return the framework region sequences to their germline configuration, for example, residue #28 of the $V_H$ of 5F8 can be "backmutated" from isoleucine to threonine. Such "backmutated" antibodies are also intended to be encompassed by the invention.

As another example, for 10H10, amino acid residue #24 (within FR1) is a valine whereas this residue in the corresponding $V_H$ 3-9 germline sequence is an alanine. To return the framework region sequences to their germline configuration, for example, residue #24 of the $V_H$ of 10H10 can be "backmutated" from valine to alanine. Such "backmutated" antibodies are also intended to be encompassed by the invention.

As another example, for 10H10, an amino acid can be inserted following amino acid residue #97 (within FR3). This amino acid is a valine. To return the framework region sequences to their germline configuration, for example, the inserted amino acid following residue #97 of the $V_H$ of 10H10 can be "backmutated" to delete this valine. Such "backmutated" antibodies are also intended to be encompassed by the invention.

As another example, for 1B12, amino acid residue #24 (within FR1) is a threonine whereas this residue in the corresponding $V_H$ 1-69 germline sequence is an alanine. To return the framework region sequences to their germline configuration, for example, residue #24 of the $V_H$ of B12 can be "backmutated" from threonine to alanine. Such "backmutated" antibodies are also intended to be encompassed by the invention.

As another example, for 1B12, amino acid residue #27 (within FR1) is an aspartic acid whereas this residue in the corresponding $V_H$ 1-69 germline sequence is an glycine. To return the framework region sequences to their germline configuration, for example, residue #27 of the $V_H$ of 1B12 can be "backmutated" from aspartic acid to glycine. Such "backmutated" antibodies are also intended to be encompassed by the invention.

As another example, for 1B12, amino acid residue #95 (within FR3) is a phenylalanine whereas this residue in the corresponding $V_H$ 1-69 germline sequence is an tyrosine. To return the framework region sequences to their germline configuration, for example, residue #95 (residue #29 of FR3) of the $V_H$ of 1B12 can be "backmutated" from phenylalanine to tyrosine. Such "backmutated" antibodies are also intended to be encompassed by the invention.

As another example, for 7H1, amino acid residue #24 (within FR1) is a threonine whereas this residue in the corresponding $V_H$ 1-69 germline sequence is an alanine. To return the framework region sequences to their germline configuration, for example, residue #24 of the $V_H$ of 7H1 can be "backmutated" from threonine to alanine. Such "backmutated" antibodies are also intended to be encompassed by the invention.

As another example, for 7H1, amino acid residue #77 (within FR3) is a threonine whereas this residue in the corresponding $V_H$ 1-69 germline sequence is a serine. To return the framework region sequences to their germline configuration, for example, residue #72 (residue #11 of FR3) of the $V_H$ of 7H1 can be "backmutated" from threonine to serine. Such "backmutated" antibodies are also intended to be encompassed by the invention.

As another example, for 11E6, amino acid residue #78 (within FR3) is an alanine whereas this residue in the corresponding $V_H$ 1-69 germline sequence is a threonine. To return the framework region sequences to their germline configuration, for example, residue #78 (residue 12 of FR3) of the $V_H$ of 11E6 can be "backmutated" from alanine to threonine. Such "backmutated" antibodies are also intended to be encompassed by the invention.

As another example, for 12B7, amino acid residue #13 (within FR1) is a glutamic acid whereas this residue in the corresponding $V_H$ 1-69 germline sequence is an lysine. To return the framework region sequences to their germline configuration, for example, residue #13 of the $V_H$ of 12B7 can be "backmutated" glutamic acid to lysine. Such "backmutated" antibodies are also intended to be encompassed by the invention.

As another example, for 12B7, amino acid residue #30 (within FR1) is an asparagine whereas this residue in the corresponding $V_H$ 1-69 germline sequence is an serine. To return the framework region sequences to their germline configuration, for example, residue #30 of the $V_H$ of 12B7 can be "backmutated" from asparagine to serine. Such "backmutated" antibodies are also intended to be encompassed by the invention.

As another example, for 12B7, amino acid residue #77 (within FR3) is an asparagine whereas this residue in the corresponding $V_H$ 1-69 germline sequence is an serine. To return the framework region sequences to their germline configuration, for example, residue #377 (residue 11 of FR3) of the $V_H$ of 12B7 can be "backmutated" from asparagine to serine. Such "backmutated" antibodies are also intended to be encompassed by the invention.

As another example, for 12B7, amino acid residue #82 (within FR3) is an aspartic acid whereas this residue in the corresponding $V_H$ 1-69 germline sequence is a glutamic acid. To return the framework region sequences to their germline configuration, for example, residue #82 (residue #16 of FR3) of the $V_H$ of 1217 can be "backmutated" from aspartic acid to glutamic acid. Such "backmutated" antibodies are also intended to be encompassed by the invention.

As another example, for 13G4, amino acid residue #27 (within FR1) Is an isoleucine whereas this residue in the corresponding $V_H$ 1-69 germline sequence is an phenylalanine. To return the framework region sequences to their germline configuration, for example, residue #27 of the $V_H$ of 12B7 can be "backmutated" from isoleucine to phenylalanine. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Can et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of he antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta at al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcy receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al. (2001) *J. Biol. Chem.* 27:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/B333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

In certain other embodiments, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamano-Ohnuki et al. (2004) *Biotechnol Bioeng* 18:614-22). As another example, EP 1,176,195 by Hanal et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanal et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J Biol. Chem.* 2:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 12:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 1:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof; typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the anti-PD-L1 antibodies having $V_H$ and $V_K$ sequences disclosed herein can be used to create new anti-PD-L1 antibodies by modifying the $V_H$ and/or $V_K$ sequences, or the constant region(s) attached thereto. Thus, in another aspect of the invention, the structural features of an anti-PD-L1 antibody of the invention, e.g. 3G10, 12A4, 10A5, 5F8, 10H10, 1B12, 7H1, 11E6, 12B7, or 13G4, are used to create structurally related anti-PD-L1 antibodies that retain at least one functional property of the antibodies of the invention, such as binding to human PD-L1. For example, one or more CDR regions of 3G10, 12A4, 10A5, 5F8, 10H10, 1B12, 71, 11E6, 12B7, or 13G4 or mutations thereof; can be combined recombinantly with known framework regions and/or other CDRs to create additional, recombinantly-engineered, anti-PD-L1 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-PD-L1 antibody comprising:

(a) providing: (i) a heavy chain variable region antibody sequence comprising a CDR1 sequence selected from the group consisting of SEQ ID NOs:21, 22, 23, 24, 25, 26, 27, 28, 29, and 30, a CDR2 sequence selected from the group consisting of SEQ ID NOs:31, 32, 33, 34, 35, 36, 37, 38, 39, and 40, and/or a CDR3 sequence selected from the group consisting of SEQ ID NOs:41, 42, 43, 44, 45, 46, 47, 48, 49, and 50; and/or (i) a light chain variable region antibody sequence comprising a CDR1 sequence selected from the group consisting of SEQ ID NOs:51, 52, 53, 54, 55, 56, 57, 58, 59, and 60, a CDR2 sequence selected from the group consisting of SEQ ID NOs:61, 62, 63, 64, 65, 66, 67, 68, 69, and 70, and/or a CDR3 sequence selected from the group consisting of SEQ ID NOs:71, 72, 73, 74, 75, 76, 77, 78, 79, and 80;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-PD-L1 antibodies described herein, which functional properties include, but are not limited to:

(i) binds to human PD-L1 with a $K_D$ of $1 \times 10^{-7}$ M or less;
(ii) increases T-cell proliferation in a mixed lymphocyte reaction (MLR) assay;
(iii) increases interferon-γ production in an MLR assay;
(iv) increases IL-2 secretion in an MLR assay;
(v) stimulates antibody responses; and/or
(vi) reverses the effect of T regulatory cells on T cell effector cells and/or dendritic cells.

The functional properties of the altered antibodies can be assessed using standard assays available in the art and/or described herein, such as those set forth in the Examples (e.g., flow cytometry, binding assays).

In certain embodiments of the methods of engineering antibodies of the invention, mutations can be introduced randomly or selectively along all or part of an anti-PD-L1 antibody coding sequence and the resulting modified anti-PD-L1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Disclosure

Another aspect of the disclosure pertains to nucleic acid molecules that encode the antibodies of the invention. The nucleic acids may be present in whole cells, in a cell lysate, or in a partially purified or substantially pure form. A nucleic acid is "isolated" or "readered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment; the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the 3G10, 12A4, 10A5, 5F8, 10H10, 1B12, 7H1, 11E6, 12B7, and 13G4, monoclonal antibodies. DNA sequences encoding the VH sequences of 3G10, 12A4, 10A5, 5F8, 10H10, 1B12, 7H1, 11E6, 12B7, and 13G4, are shown in SEQ ID NOs:81, 82, 83, 84, 85, 86, 87, 88, 89 and 90, respectively. DNA sequences encoding the VL sequences of 3G10, 12A4, 10A5, 5F8, 10H10, 1B12, 7H1, 11E6, 12B7, and 13G4, are shown in SEQ ID NOs:91, 92, 93, 94, 95, 96, 97, 98, 99 and 100, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-Ser})_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 0.5:5879-5883; McCafferty et al., (1990) Nature 48:552-554).

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against PD-L1 can be generated using transgenic or transchromosomic mice carrying parts of the human immune system rather than the mouse system. These transgenic and transchromosomic mice include mice referred to herein as HuMAb mice and KM Mice™, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 38(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann N.Y. Acad Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5:647-656; Tuaillon et al. (1993) *Proc. Natl. Acad. Sc. USA* 90:3720-3724; Choi et al. (1993) *Nature Genetics* 4:117-123; Chen, J. et al. (1993) *EMBO J.* 12: 821-830; Tuaillon et al. (1994) 1 *Immunol.* 152:2912-2920; Taylor, L et al. (1994) *International Immunology* 6:579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM Mice™," are described in detail in PCT Publication WO 02/43478 to Ishida et al.

Still further, alternative transgenic animal systems expressing human immunoglobulin genes are available in the art and can be used to raise anti-PD-L1 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucheriapati et a.

Moreover, alternative transchromosomic animal systems expressing human immunoglobulin genes are available in the art and can be used to raise anti-PD-L1 antibodies of the invention. For example, mice carrying both a human heavy chain transchromosome and a human light chain tranchromosome, referred to as "TC mice" can be used; such mice are described in Tomizuka at al. (2000) *Proc Natl. Acad Sc. USA* 22:722-727. Furthermore, cows carrying human heavy and light chain transchromosomes have been described in the art (Kuroiwa et al. (2002) *Nature Biotechnology* 20:889-894) and can be used to raise anti-PD-L1 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of PD-L1 antigen and/or recombinant PD-L1, or an PD-L1 fusion protein, as described by Lonberg, N. et al. (1994) *Nature* 0.8(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 μg) of PD-L1 antigen can be used to immunize the human Ig mice intraperitoneally.

Detailed procedures to generate fully human monoclonal antibodies to PD-L1 are described in Example 1 below. Cumulative experience with various antigens has shown that the transgenic mice respond when initially Immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-PD-L1 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen.

Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse™ strain can be used, as described in Example 1.

Generation of Hybridomas Producing Human Monoclonal Antibodies of the Disclosure To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and IX HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be re-plated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80' C.

Generation of Transfectomas Producing Monoclonal Antibodies of the Disclosure

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof; DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et a.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a property folded and immunologically active antibody. Prokaryotic expression of antibody genes has been reported to be Ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (Including dhfr-CHO cells, described in Urlaub and Chasin, (1980) *Proc. Natl. Acad. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody Into the culture medium in which the host cells are grown. Antibodies can be recovered from the culture medium using standard protein purification methods.

Characterization of Antibody Binding to Antigen

Antibodies of the invention can be tested for binding to PD-1 by, for example, standard ELISA. Briefly, microtiter plates are coated with purified PD-L1 at 0.25 µg/ml in PBS, and then blocked with 5% bovine serum albumin in PBS. Dilutions of antibody (e.g., dilutions of plasma from PD-L1-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with PD-L1 immunogen. Hybridomas that bind with high avidity to PD-L1 are subcloned and further characterized. One clone from each hybridoma, which retains the reactivity of the parent cells (by ELISA), can be chosen for making a 5-10 vial cell bank stored at −140° C., and for antibody purification.

To purify anti-PD-L1 antibodies, selected hybridomas can be grown in two-liter spinner-flasks for monoclonal antibody purification. Supenatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD1) using 1.43 extinction coefficient. The monoclonal antibodies can be aliquoted and stored at −80° C.

To determine if the selected anti-PD-L1 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using PD-L1 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4' C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-cojugated probes. Plates are developed and analyzed as described above.

Anti-PD-L1 human IgGs can be further tested for reactivity with PD-L1 antigen by Western blotting. Briefly, PD-L1 can be prepared and subjected to sodium dodecyl sulfate polyacrylamide gel electrophoresis. After electophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Antibody Physical Properties

The antibodies of the present invention may be further characterized by the various physical properties of the anti-PD-1, antibodies. Various assays may be used to detect and/or differentiate different classes of antibodies based on these physical properties.

In some embodiments, antibodies of the present invention may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) *Ann Rev Biochem* 41:673-702; Gala F A and Morrison SL (2004) *J Immunol* 12:5489-94; Wallick et al. (1988) *J Exp Med* 0.168:1099-109; Spiro R G (2002) *Glycobiology* 12:43R-56R; Parekh et al (1985) *Nature* 316: 452-7; Mimura et al. (2000) *Mol Immunol* 2:697-706). Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-PD-L1 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present invention do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et a (2002) *Electrophores* 2: 1605-11; Ma et al. (2001) *Chmronatographia* 5:S75-89; Hunt et al (1998) *J Chromatogr A* 800:355-67). In some instances, it Is preferred to have an anti-PD-L1 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning M C (2002) *Curr Pharm Biotechnol* 3:361-71). A higher thermal stability indicates greater overall antibody stability in vivo. The melting point of an antibody may be measure using techniques such as differential scanning calorimetry (Chen et al. (2003) *Pharm Res* 20:1952-60; Ghirlando et al (1999) *Immunol Leu* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present invention is greater than 60° C., preferably greater than 65'C, even more preferably greater than 70° C. Alternatively, the thermal stability of an antibody may be measure using circular dichroism (Murray et al. (2002) *J. Chromatogr Sci* 40:343-9). The thermal stability of anti-PD-L1 antibodies disolosed herein is summarized in Table 1.

TABLE 1

| mAb | Tm1 (° C.) | Tm2 (° C.) |
|---|---|---|
| 3G10 | 70 | 75 |
| 5F8 | 72 | 74 |
| 11E6 | 64 | 73 |
| 1B12 | 69 | 72 |
| 12A4 | 68 | 72 |
| 10A5 |  | 71 |
| 12B7 |  | 70 |
| 13G4 | 66 | 69 |
| 10H10 |  | 69 |

In a preferred embodiment, antibodies are selected that do not rapidly degrade. Fragmentation of an anti-PD-L1 antibody may be measured using capillary elctrophoresis (CB) and MALDI-MS, as is well understood in the art (Alexander A J and Hughes D E (1995) *Anal Chem* 673626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Immunoconjugates

In another aspect, the present invention features an anti-PD-L1 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (H) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate Is commercially available (Mylotarg®; Wyeth-Ayerst).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat Rev. Cancer* 2:750-763; Pastan, L and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof; such as abrin, ricin A, pseudomonas exotoxin, or diphtheria toxin; a protein such as tumor necrosis factor or interferon-γ; or, biological response modifiers such as, for example, lymphokines, interleukin-1 ("IL-1") interleukin-2 ("IL-2"), interleukin-6 ("IL-6"), granulocyte macrophage colony stimulating factor ("GM-CSF"), granulocyte colony stimulating factor ("C-CSF"), or other growth factors.

Techniques for conjugating such therapeutic moiety to antibodies are well known, see, e.g., Amon et al., "Monoclonal Antibodies For immunotargeting Of Drugs In Cancer Therapy," in Monoclonal Antibodies And Cancer Therapy, Reisfold et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review." in Monoclonal Antibodies'84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985), and Thorpe at al., "The Preparation And Cytotoxic Properties Of Antibody-Toxin Conjugates," Immunol. Rev., 62:119-58 (1982).

Bispecific Molecules

In another aspect, the present invention features bispecific molecules comprising an anti-PD-L1 antibody, or a fragment thereon of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for PD-L1 and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR or FcαR expressing effector cells (e.g., monocytes, macrophages or polymorphonuclear cells (PMNs)), and to target cells expressing PD-L. These bispecific molecules target PD-L1 expressing cells to effector call and trigger Fc receptor-mediated effector cell activities, such as phagocytosis of an PD-L1 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fe binding specificity and an anti-PD-L1 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_C$ receptor or target cell antigen. The "anti-enhancement factor portion" can bind an Fe receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab)$_2$, Fv, or a single chain Fv. The antibody may also be a light chain or heavy chain dimer, or any minimal fragment thereof such as a Fv or a single chain construct as described in Ladner et a. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRI(CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ $M^{-1}$) for both IgA1 and IgA2, which is increased upon exposure to cytokines such as G-CSF or GM-CSF (Morton, H. C. et al (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immuno* 148:1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-PD-L1 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohexane-1-carboxylate (sulfo-SMCC) (see e.g., Karpovsky et al. (1984) *J. Exp. Med.* 160:1686; Liu, M A et al. (1985) *Proc. Natl. Acad Sci. USA* 82:8648). Other methods include those described in Paulus (1985) Behring Ins. Mitt. No. 78, 118-132; Brennan et al. (1985) *Science* 22:81-83), and Glennie et al. (1987) *Immunol.* 132: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbant assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B, Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-PD-L1 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e. antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated Into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-PD-L1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient in some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient in general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-PD-L1 antibody of the invention preferably results in a decrease in severity of disease symptoms, an increase in frequency and duration of disease symptom-free periods, or a prevention of impairment or disability due to the disease affliction. For example, for the treatment of PD-L1+tumors, a "therapeutically effective dosage" preferably inhibits cell growth or tumor growth by at least about 20, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 22:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. O. Bloeman et al. (1995) *FEBS Lett.* 35:140; M. Owais et al. (1995) *Antimicrob. Agents Chemother.* 3:180); surfactant protein A receptor (Briscoe et al. (1995) *Am. J. Physiol.* 1233:134); p120 (Schreier et al. (1994) *J Biol. Chem.* 2:9090); see also K. Keinanen; M. L. Laukkanen (1994) *FEBS Lett* 46:123; J. J. Killion; I. J. Fidler (1994) *Immunomethods* 4:273.

Uses and Methods of the invention

The antibodies, antibody compositions and methods of the present invention have numerous in vitro and in vivo utilities involving, for example, detection of PD-L1 or enhancement of immune response by blockade of PD-L1. In a preferred embodiment, the antibodies of the present invention are human antibodies. For example, these molecules can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject the antibody, or antigen-binding portion thereof of the invention such that the immune response in the subject Is modified. Preferably, the response is enhanced, stimulated or up-regulated.

As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vive. To achieve antigen-specific enhancement of immunity, the anti-PD-L1 antibodies can be administered together with an antigen of interest. When antibodies to PD-L1 are administered together with another agent, the two can be administered in either order or simultaneously.

The invention further provides methods for detecting the presence of human PD-L1 antigen in a sample, or measuring the amount of human PD-L1 antigen, comprising contacting the sample, and a control sample, with a human monoclonal antibody, or an antigen binding portion thereof, which specifically binds to human PD-L1, under conditions that allow for formation of a complex between the antibody or portion thereof and human PD-L1. The formation of a complex is then detected, wherein a difference complex formation between the sample compared to the control sample is indicative the presence of human PD-L1 antigen in the sample.

Cancer

Blockade of PD-L1 by antibodies can enhance the immune response to cancerous cells in the patient. PD-L1 is not expressed in normal human cells, but is abundant in a variety of human cancers (Dong et al. (2002) *Nat Med* 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) *J Mol Med* 81:281-7; Blank et al. (2004) *Cancer Immunol. Immunother.* [epub]; Konishi et al. (2004) *Clin. Cancer Res.* 10:5094-100). Immune suppression can be reversed by inhibiting the local interaction of PD-L1 to PD-1 and the effect is additive when the interaction of PD-L2 to PD-1 is blocked as well (Iwai et al. (2002) *PNAS* 92:12293-7; Brown et al. (2003) *J. Immunol.* 170:1257-66). An anti-PD-L1 antibody may be used alone to inhibit the growth of cancerous tumors. Alternatively, an anti-PD-L1 antibody may be used in conjunction with other immunogenic agents, standard cancer treatments, or other antibodies, as described below.

Accordingly, in one embodiment, the invention provides a method of inhibiting growth of tumor cells in a subject, comprising administering to the subject a therapeutically effective amount of an anti-PD-L1 antibody, or antigen-binding portion thereof. Preferably, the antibody is a human anti-PD-L1 antibody (such as any of the human anti-human PD-L1 antibodies described herein). Additionally or alternatively, the antibody may be a chimeric or humanized anti-PD-L1 antibody.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer, prostate cancer, breast cancer, colon cancer and lung cancer. Examples of other cancers that may be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small Intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) *Int. Immunol.* 17:133-144).

Optionally, antibodies to PD-L1 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) *J.*

*Immunol.* 713:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF (discussed further below).

In humans, some tumors have been shown to be immunogenic such as melanomas. It is anticipated that by raising the threshold of T cell activation by PD-L1 blockade, we may expect to activate tumor responses in the host.

PD-L1 blockade is likely to be most effective when combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayai, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90:3539-43).

The study of gene expression and large scale gene expression patterns in various tumors has led to the definition of so-called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) *Science* 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (i.e. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269:1585-1588; Tamura, Y. et al. (1997) *Science* 228:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al. (1998) *Cancer Research* 58: 5301-5304). An example of such a combination is an anti-PD-L1 antibody in combination with decarbazine for the treatment of melanoma. Another example of such a combination is an anti-PD-L1 antibody in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

PD-L1 blocking antibodies can also be used in combination with bispecific antibodies that target Fc alpha or Fc γ receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of PD-L1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13:198-200), and Fas ligand (Hahne, M. et al. (1996) *Science* 274: 1363-1365). Antibodies to each of these entities may be used in combination with anti-PD-L1 to counteract the effects of the immunosuppressive agent and favor tumor immune responses by the host.

Other antibodies which may be used to activate host immune responsiveness can be used in combination with anti-PD-L1. These include molecules on the surface of dendritic cells which activate DC function and antigen presentation. Anti-CD40 antibodies are able to substitute effectively for T cell helper activity (Ridge, J. et al. (1998) *Nature* 393: 474-478) and can be used in conjunction with PD-L1 antibodies (Ito, N. et al. (2000) *Immunobiology* 201 (5) 527-40). Activating antibodies to T cell costimulatory molecules such as OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) as well as antibodies which block the activity of negative costimulatory molecules such as CTLA-4 (e.g., U.S. Pat. No. 5,811,097) or BTLA (Watanabe, N. et al. (2003) *Nat Immunol* 4:670-9), B7-H4 (Sica, G L et al. (2003) *Immunity* 18:849-61) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. & Riddell, S. (1999) *Science* 285: 546-51). These methods may also be used to activate T cell responses to infectious agents such as CMV. Ex vivo activation in the presence of anti-PD-L1 antibodies may be expected to increase the frequency and activity of the adoptively transferred T cells.

Infectious Diseases Other methods of the invention are used to treat patients that have been exposed to particular toxins or pathogens. Accordingly, another aspect of the invention provides a method of treating an infectious disease in a subject comprising administering to the subject an anti-PD-L1 antibody, or antigen-binding portion thereof such that the subject is treated for the infectious disease. Preferably, the antibody is a human anti-human PD-L1 antibody (such as any of the human anti-PD-L1 antibodies described herein). Additionally or alternatively, the antibody can be a chimeric or humanized antibody.

Similar to its application to tumors as discussed above, antibody mediated PD-L1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, Leishmania, Staphylococcus aureus, Pseudomonas Aeruginosa. PD-L1 blockade is particularly useful against established infections by agents such as HIV that present altered antigens over the course of the infections. These novel epitopes are recognized as foreign at the time of anti-human PD-L1 administration, thus provoking a strong T cell response that Is not dampened by negative signals through PD-L1.

Some examples of pathogenic viruses causing infections treatable by methods of the invention include HIV, hepatitis (A, B, or C), herpes virus (e.g., VZV, HSV-1, HAV-6, HSV-II and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Some examples of pathogenic fungi causing infections treatable by methods of the invention include *Candida* (*albicans, krusei, glabrata, tropicalis*, etc.), *Cryptococcus neoformans*, *Aspergillus* (*fumigatus, niger*, etc.), Genus *Mucorales* (*Mucor, Absidia, rhizophus*), *Sporothrix schenkii, Blasatomyes dermatitidis, Paracocidioides brasiliensis, Coccidioides immitis* and *Histoplasma capsulatum*.

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

In all of the above methods, PD-L1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad Sc. USA* 90:6444-6448; Poljak (1994) *Structure* 2:1121-1123).

Autoimmune Reactions

Anti-PD-L1 antibodies may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B16 melanoma in van Elsas et al. supra; depigmentation in Trp-2 vaccinated mice (Overwijk, W. et al. (1999) *Proc. Natl. Acad Sci. U.S.A.* 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) *J. Immunother Emphasis Tumor Immunol* 19(1): 81-4).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of Aβ peptide in amyloid deposits in the brain; antibody responses against amyloid are able to clear these amyloid deposits (Schenk et al., (1999) *Nature* 400: 173-177).

Other self proteins may also be used as targets such as IgE for the treatment of allergy and asthma, and TNFα for rheumatoid arthritis. Finally, antibody responses to various hormones may be induced by the use of anti-PD-L1 antibody. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 antibody can be used for induction of therapeutic autoimmune responses to treat patients having an inappropriate accumulation of other self-antigens, such as amyloid deposits, including Aβ in Alzheimer's disease, cytokines such as TNFα, and IgE.

Vaccines

Anti-PD-L1 antibodies may be used to stimulate antigen-specific immune responses by coadministration of an anti-PD-L1 antibody with an antigen of interest (e.g., a vaccine). Accordingly, in another aspect the invention provides a method of enhancing an immune response to an antigen in a subject, comprising administering to the subject (i) the antigen; and (ii) an anti-PD-L1 antibody, or antigen-binding portion thereof, such that an Immune response to the antigen in the subject is enhanced. Preferably, the antibody is a human anti-human PD-L1 antibody (such as any of the human anti-PD-L1 antibodies described herein). Additionally or alternatively, the antibody can be a chimeric or humanized antibody. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Anti-PD-L1 antibodies may also be used to abrogate secondary effects associated with diseases such as T cell suppressed wasting disease with colitis (Kanai et a. (2003) *J. Immunol.* 171:4156-63). Accordingly, in another aspect the invention provides a method of abrogating leukocyte infiltration, decreasing production of IFN-γ, IL-2, and IFN-α by T cells. Preferably, the antibody is a human anti-human PD-L1 antibody (such as any of the human anti-PD-L1 antibodies described herein). Additionally or alternatively, the antibody can be a chimeric or humanized antibody.

Anti-PD-L1 antibodies may also be used to treat diseases such as chronic inflammatory diseases, such as lichen planus, a T-cell mediated chronic inflammatory mucocutaneous disease (Youtgnak-Piboonratanakit et al. (2004) *Immnol Letters* 94:215-22). Accordingly, in another aspect the invention provides a method of abrogating chronic inflammatory disease by T cells. Preferably, the antibody is a human anti-human PD-L1 antibody (such as any of the human anti-PD-L1 antibodies described herein). Additionally or alternatively, the antibody can be a chimeric or humanized antibody.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-PD-L1 antibodies of the invention can be co-administered with one or other more therapeutic agents, e g, a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-PD-L1 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present invention are kits comprising the antibody compositions of the invention (e.g., human antibodies, bispecific or multispecific molecules, or immunoconjugates) and instructions for use. The kit can further contain a least one additional reagent, or one or more additional human antibodies of the invention (e.g., a human antibody having a complementary activity which binds to an epitope in PD-L1 antigen distinct from the first human antibody). Kits typically include a label indicating the intended use of the contents of the kit. The term label includes any writing, or recorded material supplied on or with the kit, or which otherwise accompanies the kit.

The present invention is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against PD-L1

Antigen

Immunization protocols utilized as antigen both (i) a recombinant fusion protein comprising the extracellular portion of PD-L1, and (ii) membrane bound full-length PD-L1. Both antigens were generated by recombinant transfection methods in a CHO cell line.

Transgenic Mice (KM-Mouse® Colony

Fully human monoclonal antibodies to PD-L1 were prepared using the KM strain of transgenic transchromosomic mice, which expresses human antibody genes. In this mouse strain, the endogenous mouse kappa light chain gene has been homozygously disrupted as described in Chan et al. (1993) *EMBO J.* 12:811-820 and the endogenous mouse heavy chain gene has been homozygously disrupted as described in Example 1 of PCT Publication WO 01/09187. Furthermore, this mouse strain carries a human kappa light chain transgene, KCo5, as described in Fishwild et al (1996) *Nature Biotechnology* 14:845-851, and a SC20 transchromosome as described in PCT Publication WO 02/43478.

KM-Mouse® Immunizations

To generate fully human monoclonal antibodies to PD-L1, a cohort of mice of the KM-Mouse® strain were immunized with purified recombinant PD-L1-Ig and PD-L1-transfected CHO cells as antigen. General immunization schemes for HuMab mice are described in Lonberg, N. et al. (1994) *Nature* 368(6474): 856-859; Fishwild, D. et al. (1996) *Nature Biotechnology* 14: 845-851 and PCT Publication WO 98/24884. The mice were 6-16 weeks of age upon the first infusion of antigen. A purified recombinant preparation (5-50 μg) of PD-L1-Ig antigen and 5-10×10$^6$ cells were used to immunize the HuMab mice intraperitonealy (IP), subcutaneously (Sc) or via footpad injection.

Transgenic mice were immunized twice with antigen in complete Freund's adjuvant or Ribi adjuvant IP, followed by 3-21 days IP (up to a total of 11 immunizations) with the antigen in Incomplete Freund's or Ribi adjuvant. The immune response was monitored by retroorbital bleeds. The plasma was screened by ELISA (as described below), and mice with sufficient titers of anti-PD-L1 human immunogolobulin were used for fusions. Mice were boosted intravenously with antigen 3 days before sacrifice and removal of the spleen. Typically, 10-35 fusions for each antigen were performed. Several dozen mice were immunized for each antigen.

Selection of KM-Mouse® Producing Anti-PD-L1 Antibodies: To select HuMab mice producing antibodies that bound PD-L1, sera from immunized mice were tested by ELISA as described by Fishwild, D. et al. (1996). Briefly, microtiter plates were coated with purified recombinant PD-L1 fusion protein from transfected CHO cells at 1-2 µg/ml in PBS, 100 µl/wells incubated 4° C. overnight then blocked with 200 µl/well of 5% fetal bovine serum in PBS/Tween (0.05%). Dilutions of sera from PD-L1-immunized mice were added to each well and incubated for 1-2 hours at ambient temperature. The plates were washed with PBS/Tween and then incubated with a goat-anti-human IgG polyclonal antibody conjugated with horseradish peroxidase (HRP) for 1 hour at room temperature. After washing, the plates were developed with ABTS substrate (Sigma, A-1888, 0.22 mg/ml) and analyzed by spectrophotometer at OD 415-495. Mice that developed the highest titers of anti-PD-L1 antibodies were used for fusions. Fusions were performed as described below and hybridoma supernatants were tested for anti-PD-L1 activity by ELISA.

Generation of Hybridomas Producing Human Monoclonal Antibodies to PD-L1:

The mouse splenocytes, isolated from a KM mouse, were fused with PEG to a mouse myeloma cell line based upon standard protocols. The resulting hybridomas were then screened for the production of antigen-specific antibodies. Single cell suspensions of splenocytes from immunized mice were fused to one-fourth the number of SP2/0 nonsecreting mouse myeloma cells (ATCC, CRL 1581) with 50% PEG (Sigma). Cells were plated at approximately $1 \times 10^5$/well in flat bottom microtiter plate, followed by about two week incubation in selective medium containing 10% fetal bovine serum, 10% P388DI (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Individual wells were then screened by ELISA (described above) for human anti-PD-L1 monoclonal IgG antibodies. Once extensive hybridoma growth occurred, medium was monitored usually after 10-14 days. The antibody-secreting hybridomas were re-plated, screened again and, if still positive for human IgG, anti-PD-L1 monoclonal antibodies were subcloned at least twice by limiting dilution. The stable subclones were then cultured in vitro to generate small amounts of antibody in tissue culture medium for further characterization.

Hybridoma clones 3G10, 12A4, 10A5, 5F8, 10H10, 1B12, 7H1, 11E6, 12B7, and 13G4 were selected for further analysis.

Example 2

Structural Characterization of Human Monoclonal Antibodies 3G10, 12A4, and 10A5

The cDNA sequences encoding the heavy and light chain variable regions of the 3G10, 12A4, 10A5, 5F8, 10H1, 1B12, 7H1, 11E6, 12B7, and 13G4 monoclonal antibodies were obtained from the 3G10, 12A4, 10A5, 5F8, 10H10, 1B12, 7H1, 11E6, 12B7, and 13G4 hybridomas, respectively, using standard PCR techniques and were sequenced using standard DNA sequencing techniques.

The nucleotide and amino acid sequences of the heavy chain variable region of 3G10 are shown in FIG. 1A and in SEQ ID NO:81 and 1, respectively.

The nucleotide and amino acid sequences of the light chain variable region of 3G10 are shown in FIG. 1B and in SEQ ID NO:91 and 11, respectively.

Comparison of the 3G10 heavy chain immunoglobulin sequence to the known human germline immunoglobulin heavy chain sequences demonstrated that the 3G10 heavy chain utilizes a VH segment from human germline VH 1-18, an undetermined D segment, and a JH segment from human germline JH 6b. The alignment of the 3G10 VH sequence to the germline VH 1-18 sequence is shown in FIG. 11. Further analysis of the 3G10 VH sequence using the Kabat system of CDR region determination led to the delineation of the heavy chain CDR1, CDR2 and CD3 regions as shown in FIGS. 1A and 11, and in SEQ ID NO:21, 31 and 41, respectively.

Comparison of the 3G10 light chain immunoglobulin sequence to the known human germline immunoglobulin light chain sequences demonstrated that the 3G10 light chain utilizes a VL segment from human germline VK L6 and a JK segment from human germline JK 1. The alignment of the 3G10 VL sequence to the germline VK L6 sequence is shown in FIG. 21. Further analysis of the 3G010 VL sequence using the Kabat system of CDR region determination led to the delineation of the light chain CDR1, CDR2 and CD3 regions as shown in FIGS. 1B and 21, and in SEQ ID NOs:51, 61 and 71, respectively.

The nucleotide and amino acid sequences of the heavy chain variable region of 12A4 are shown in FIG. 2A and in SEQ ID NO:82 and 2, respectively.

The nucleotide and amino acid sequences of the light chain variable region of 12A4 are shown in FIG. 2B and in SEQ ID NO:92 and 12, respectively.

Comparison of the 12A4 heavy chain immunoglobulin sequence to the known human germline immunoglobulin heavy chain sequences demonstrated that the 12A4 heavy chain utilizes a VH segment from human germline VH 1-69, a D segment from human germline 3-10, and a JH segment from human germline JH 6b. The alignment of the 12A4 VH sequence to the germline VH 1-69 sequence is shown in FIG. 12. Further analysis of the 12A4 VH sequence using the Kabat system of CDR region determination led to the delineation of the heavy chain CDR1, CDR2 and CD3 regions as shown in FIGS. 2A and 12, and in SEQ ID NOs:22, 32 and 42, respectively.

Comparison of the 12A4 light chain immunoglobulin sequence to the known human germline immunoglobulin light chain sequences demonstrated that the 12A4 light chain utilizes a VL segment from human germline VK 16 and a JK segment from human germline JK 1. The alignment of the 12A4 VL sequence to the germline VK L6 sequence is shown in FIG. 22. Further analysis of the 12A4 VL sequence using the Kabat system of CDR region determination led to the delineation of the light chain CDR1, CDR2 and CD3 regions as shown in FIGS. 2B and 22, and in SEQ ID NOs:52, 62 and 72, respectively.

The nucleotide and amino acid sequences of the heavy chain variable region of 10A5 are shown in FIG. 3A and in SEQ ID NO:83 and 3, respectively.

The nucleotide and amino acid sequences of the light chain variable region of 10A5 are shown in FIG. 3B and in SEQ ID NO:93 and 13, respectively.

Comparison of the 10A5 heavy chain immunoglobulin sequence to the known human germline immunoglobulin heavy chain sequences demonstrated that the 10A5 heavy chain utilizes a VH segment from human germline VH 1-3, a D segment from human germline 5-5, and a JH segment from human germline JH 4b. The alignment of the 10A5 VH sequence to the germline VH 1-3 sequence is shown in FIG. 13. Further analysis of the 10A5 VH sequence using the Kabet system of CDR region determination led to the delineation of the heavy chain CDR1, CDR2 and CD3 regions as shown in FIGS. 3A and 13, and in SEQ ID NOs:23, 33, and 43, respectively.

Comparison of the 10A5 light chain immunoglobulin sequence to the known human germline immunoglobulin light chain sequences demonstrated that the 10A5 light chain utilizes a VL segment from human germline VK L15 and a JK segment from human germline JK 2. The alignment of the 10A5 VL sequence to the germline VK L15 sequence is shown in FIG. 23. Further analysis of the 10A5 VL sequence using the Kabat system of CDR region determination led to the delineation of the light chain CDR1, CDR2 and CD3 regions as shown in FIGS. 3B and 23, and in SEQ ID NOs:53, 63, and 73, respectively.

The nucleotide and amino acid sequences of the heavy chain variable region of 5F8 are shown in FIG. 4A and in SEQ ID NO:84 and 4, respectively.

The nucleotide and amino acid sequences of the light chain variable region of 5F8 are shown in FIG. 4B and in SEQ ID NO:94 and 14, respectively.

Comparison of the 5F8 heavy chain immunoglobulin sequence to the known human germline immunoglobulin heavy chain sequences demonstrated that the 5F8 heavy chain utilizes a VH segment from human germline VH 1-69, a D segment from human germline 6-13, and a JH segment from human germline JH 4b. The alignment of the 5F8 VH sequence to the germline VH 1-69 sequence is shown in FIG. 14. Further analysis of the 5F8 VH sequence using the Kabat system of CDR region determination led to the delineation of the heavy chain CDR1, CDR2 and CD3 regions as shown in FIGS. 4A and 14, and in SEQ ID NOs:24, 34, and 44, respectively.

Comparison of the 5F8 light chain immunoglobulin sequence to the known human germline immunoglobulin light chain sequences demonstrated that the 5F8 light chain utilizes a VL segment from human germline VK A27 and a JK segment from human germline JK 1. The alignment of the 5F8 VL sequence to the germline VK A27 sequence is shown in FIG. 24. Further analysis of the 5F8 VL sequence using the Kabat system of CDR region determination led to the delineation of the light chain CDR1, CDR2 and CD3 regions as shown in FIGS. 4B and 24, and in SEQ ID NOs:54, 64, and 74, respectively.

The nucleotide and amino acid sequences of the heavy chain variable region of 10H10 are shown in FIG. 5A and in SEQ ID NO:85 and 5, respectively.

The nucleotide and amino acid sequences of the light chain variable region of 10H10 are shown in FIG. 5B and in SEQ ID NO:95 and 15, respectively.

Comparison of the 10H10 heavy chain immunoglobulin sequence to the known human germline immunoglobulin heavy chain sequences demonstrated that the 10H10 heavy chain utilizes a VH segment from human germline VH 3-9, a D segment from human germline 4-17, and a JH segment from human germline JH 4b. The alignment of the 10H10 VH sequence to the germline VH 3-9 sequence is shown in FIG. 15. Further analysis of the 10H10 VH sequence using the Kabat system of CDR region determination led to the delineation of the heavy chain CDR1, CDR2 and CD3 regions as shown in Figures SA and 15, and in SEQ ID) NOs:25, 35, and 45, respectively.

Comparison of the 10H10 light chain immunoglobulin sequence to the known human germline immunoglobulin light chain sequences demonstrated that the 10H10 light chain utilizes a VL segment from human germline VK L15 and a JK segment from human germline JK 2. The alignment of the 10H10 VL sequence to the germline VK L15 sequence is shown in FIG. 25. Further analysis of the 10H10 VL sequence using the Kabat system of CDR region determination led to the delineation of the light chain CDR1, CDR2 and CD3 regions as shown in Figures SB and 25, and in SEQ ID NOs:55, 65, and 75, respectively.

The nucleotide and amino acid sequences of the heavy chain variable region of 1B12 are shown in FIG. 6A and in SEQ ID NO:86 and 6, respectively.

The nucleotide and amino acid sequences of the light chain variable region of 1B12 are shown in FIG. 6B and in SEQ ID) NO:96 and 16, respectively.

Comparison of the 1B12 heavy chain immunoglobulin sequence to the known human germline immunoglobulin heavy chain sequences demonstrated that the 1B12 heavy chain utilizes a VH segment from human germline VH 1-69, a D segment from human germline 3-10, and a JH segment from human germline JH 6b. The alignment of the 1B12 VH sequence to the germline VH 1-69 sequence is shown in FIG. 16. Further analysis of the 1B12 VH sequence using the Kabat system of CDR region determination led to the delineation of the heavy chain CDR1, CDR2 and CD3 regions as shown in FIGS. 6A and 16, and in SEQ ID NOs:26, 36, and 46, respectively.

Comparison of the 1B12 light chain immunoglobulin sequence to the known human germline immunoglobulin light chain sequences demonstrated that the 1B12 light chain utilizes a VL segment from human germline VK L6 and a JK segment from human germline JK 1. The alignment of the 1B12 VL sequence to the germline VK L6 sequence is shown in FIG. 26. Further analysis of the 1B12 VL sequence using the Kabat system of CDR region determination led to the delineation of the light chain CDR1, CDR2 and CD3 regions as shown in FIGS. 61 and 26, and in SEQ ID NOs:56, 66, and 76, respectively.

The nucleotide and amino acid sequences of the heavy chain variable region of 7H1 are shown in FIG. 7A and in SEQ ID NO:87 and 7, respectively.

The nucleotide and amino acid sequences of the light chain variable region of 7H1 are shown in FIG. 7B and in SEQ ID NO:97 and 17, respectively.

Comparison of the 7H1 heavy chain immunoglobulin sequence to the known human germline immunoglobulin heavy chain sequences demonstrated that the 7H1 heavy chain utilizes a VH segment from human germline VH 1-69, a D segment from human germline 3-10, and a JH segment from human germline JH 6b. The alignment of the 7H1 VH sequence to the germline VII 1-69 sequence is shown in FIG. 17. Further analysis of the 7H1 VH sequence using the Kabat system of CDR region determination led to the delineation of the heavy chain CDR1, CDR2 and CD3 regions as shown in FIGS. 7A and 17, and in SEQ ID NOs:27, 37, and 47, respectively.

Comparison of the 7H1 light chain immunoglobulin sequence to the known human germline immunoglobulin light chain sequences demonstrated that the 7H1 light chain utilizes a VL segment from human germline VK L6 and a JK segment from human germline JK 1. The alignment of the 7H1 VL sequence to the germline VK L6 sequence is shown in FIG. 27. Further analysis of the 7H1 VL sequence using the Kabat system of CDR region determination led to the delineation of the light chain CDR1, CDR2 and CD3 regions as shown in FIGS. 7B and 27, and in SEQ ID NOs:57, 67, and 77, respectively.

The nucleotide and amino acid sequences of the heavy chain variable region of 11E6 are shown in FIG. 4A and in SEQ ID NO:84 and 4, respectively.

The nucleotide and amino acid sequences of the light chain variable region of 11E6 are shown in FIG. 4l and in SEQ ID NO:94 and 14, respectively.

Comparison of the 11E6 heavy chain Immunoglobulin sequence to the known human germline immunoglobulin heavy chain sequences demonstrated that the 11E6 heavy chain utilizes a VH segment from human germline VH 1-69, a D segment from human germline 6-19, and a JH segment from human germline JH 6c. The alignment of the 11E6 VH sequence to the germline VH 1-69 sequence is shown in FIG. 18. Further analysis of the 11E6 VH sequence using the Kabat system of CDR region determination led to the delineation of the heavy chain CDR1, CDR2 and CD3 regions as shown in FIGS. 8A and 18, and in SEQ ID NOs:28, 38, and 4, respectively.

Comparison of the 11E6 light chain immunoglobulin sequence to the known human germline immunoglobulin light chain sequences demonstrated that the 11E6 light chain utilizes a VL segment from human germline VK A27 and a JK segment from human germline JK 4. The alignment of the 11E6 VL sequence to the germline VK A27 sequence is shown in FIG. 27. Further analysis of the 11E6 VL sequence using the Kabat system of CDR region determination led to the delineation of the light chain CDR1, CDR2 and CD3 regions as shown in FIGS. 8B and 28, and in SEQ ID NOs:58, 68, and 78, respectively. In addition, a second related clone included the VK sequence as shown in SEQ ii) NO:109. This antibody is denoted herein as 11E6a.

The nucleotide and amino acid sequences of the heavy chain variable region of 12B7 are shown in FIG. 9A and in SEQ ID NO:89 and 9, respectively.

The nucleotide and amino acid sequences of the light chain variable region of 12B7 are shown in FIG. 9B and in SEQ ID NO:99 and 19, respectively.

Comparison of the 12B7 heavy chain immunoglobulin sequence to the known human germline immunoglobulin heavy chain sequences demonstrated that the 12B7 heavy chain utilizes a VH segment from human germline VH 1-69, a D segment from human germline 3-10, and a JH segment from human germline JH 6b. The alignment of the 12B7 VH sequence to the germline VH 1-69 sequence is shown in FIG. 19. Further analysis of the 12B7 VH sequence using the Kabat system of CDR region determination led to the delineation of the heavy chain CDR1, CDR2 and CD3 regions as shown in FIGS. 9A and 19, and in SEQ ID NOs:29, 39, and 49, respectively.

Comparison of the 12B7 light chain immunoglobulin sequence to the known human germline immunoglobulin light chain sequences demonstrated that the 12B7 light chain utilizes a VL segment from human germline VK L6 and a JK segment from human germline JK 5. The alignment of the 12B7 VL sequence to the germline VK L6 sequence is shown in FIG. 29. Further analysis of the 12B7 VL sequence using the Kabat system of CDR region determination led to the delineation of the light chain CDR1, CDR2 and CD3 regions as shown in FIGS. 9B and 29, and in SEQ ID NOs:59, 69, and 79, respectively.

The nucleotide and amino acid sequences of the heavy chain variable region of 13G4 are shown in FIG. 10A and in SEQ ID NO:90 and 10, respectively.

The nucleotide and amino acid sequences of the light chain variable region of 13G4 are shown in FIG. 10B and in SEQ ID NO:100 and 20, respectively.

Comparison of the 13G4 heavy chain immunoglobulin sequence to the known human germline immunoglobulin heavy chain sequences demonstrated that the 13G4 heavy chain utilizes a VH segment from human germline VH 3-9, a D segment from human germline 3-9, and a JH segment from human germline JH 4b. The alignment of the 13G4 VH sequence to the germline VH 3-9 sequence is shown in FIG. 20. Further analysis of the 13G4 VH sequence using the Kabat system of CDR region determination led to the delineation of the heavy chain CDR1, CDR2 and CD3 regions as shown in FIGS. 10A and 20, and in SEQ ID NOs:30, 40, and 50, respectively.

Comparison of the 13G4 light chain immunoglobulin sequence to the known human germline immunoglobulin light chain sequences demonstrated that the 13G4 light chain utilizes a VL segment from human germline VK L18 and a JK segment from human germline JK 3. The alignment of the 13G4 VL sequence to the germline VK L18 sequence is shown in FIG. 30. Further analysis of the 13G4 VL sequence using the Kabat system of CDR region determination led to the delineation of the light chain CDR1, CDR2 and CD3 regions as shown in FIGS. 10B and 30, and in SEQ ID NOs:60, 70, and 80, respectively.

Example 3

Characterization of Binding Specificity and Binding Kinetics of Anti-PD-L1 Human Monoclonal Antibodies In this example, binding affinity and binding kinetics of anti-PD-L1 antibodies were examined by Biacore analysis. Binding specificity, and cross-competition were examined by flow cytometry.

Binding Affinity and Kinetics

Anti-PD-L1 antibodies were characterized for affinities and binding kinetics by Biacore analysis (Biacore AB, Uppsala, Sweden). Purified recombinant human PD-L1 fusion protein was covalently linked to a CM5 chip (carboxy methyl dextran coated chip) via primary amines, using standard amine coupling chemistry and kit provided by Biacore, to a density of 562 RUs. Binding was measured by flowing the antibodies in HBS EP buffer (provided by Biacore AB) at a concentration of 133 nM at a flow rate of 50 µl/min. The antigen-antibody association kinetics was followed for 1 minute and the dissociation kinetics was followed for 1 minute. The association and dissociation curves were fit to a 1:1 Langmuir binding model using BIAevaluation software (Biacore AB). To minimize the effects of avidity in the estimation of the binding constants, only the initial segment of data corresponding to association and dissociation phases were used for fitting. The $K_d$, $k_{on}$ and $k_{off}$ values that were determined are shown in Table 2.

TABLE 2

Biacore binding data for PD-L1 human monoclonal antibodies

| Sample # | Sample ID | Affinity $K_D \times 10^{-9}$ (M) | On rate $k_{on} \times 10^5$ (1/Ms) | Off rate $k_{off} \times 10^{-4}$ 1/s |
|---|---|---|---|---|
| 1 | 3G10 | 3.39 | 5.25 | 17.8 |
| 3 | 10A5 | 1.45 | 2.58 | 3.72 |

Additional binding data obtained by equilibrium binding method and analyzed on GraphPad Prizm is shown in Table 3.

TABLE 3

Biacore equilibrium binding data for PD-L1 human monoclonal antibodies.

| Clone ID | $K_D$ (nM) 37 C. | $K_D$ (nM) 25 C. |
|---|---|---|
| 12A4 | 1.94 | 0.76 |
| 7H1 | 2.15 | nd |
| 1B12 | 1.38 | 0.61 |
| 12B7 | 0.83 | 0.53 |
| 10A5 | 2.41 | 0.57 |
| 10H10 | 5.93 | 5.48 |
| 13G4 | 1.87 | 3.3 |
| 11E6 | 0.53 | 2.9 |
| 5F8 | 2.17 | 0.75 |

Binding Specificity by Flow Cytometry

Figure 33:
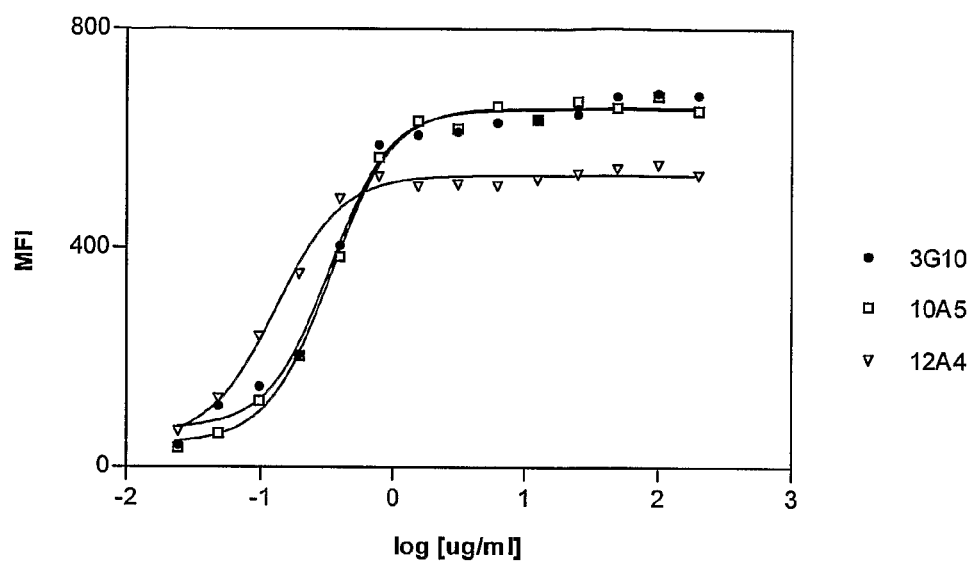
FIG. 33 shows the results of flow cytometry experiments demonstrating that the human monoclonal antibodies 3G10, 10A5, and 12A4, directed against human PD-L1, binds the cell surface of CHO cells transfected with full-length human PD-L1 in a concentration dependent manner.

Chinese hamster ovary (CHO) cell lines that express recombinant human PD-L1 at the cell surface were developed and used to determine the specificity of PD-L1 human monoclonal antibodies by flow cytometry. CHO cells were transfected with expression plasmids containing full length cDNA encoding transmembrane forms of PD-L1. Binding of the 3G10, 10A5, and 12A4 anti-PD-L1 human monoclonal antibodies was assessed by incubating the transfected cells with the anti-PD-L1 human monoclonal antibody. The cells were washed and binding was detected with a FITC-labeled anti-human IgG Ab. Flow cytometric analyses were performed using a FACScan flow cytometry (Becton Dickinson, San Jose, Calif.). The binding was compared to the parent CHO cell line. The results are shown in FIGS. 32A (HuMAb 3G10), 32B (HuMAb 10A5) and 32C (HuMAb 12A4). Binding was also tested using varying concentrations of an anti-PD-L1 antibody. The results are shown in FIG. 33. The anti-PD-L1 human monoclonal antibodies 3G10, 10A5, and 12A4 bound to the CHO cells transfected with PD-L1 in a concentration dependent manner. These data demonstrate that the anti-PD-L1 human monoclonal antibodies specifically bind to cell surface PD-L1.

Binding Specificity by ELISA

The specificity of the anti-PD-L1 monoclonal antibodies was determined using a standard ELISA assay for binding to a human PD-L1 fusion to an immunoglobulin Fc region.

Figure 34:
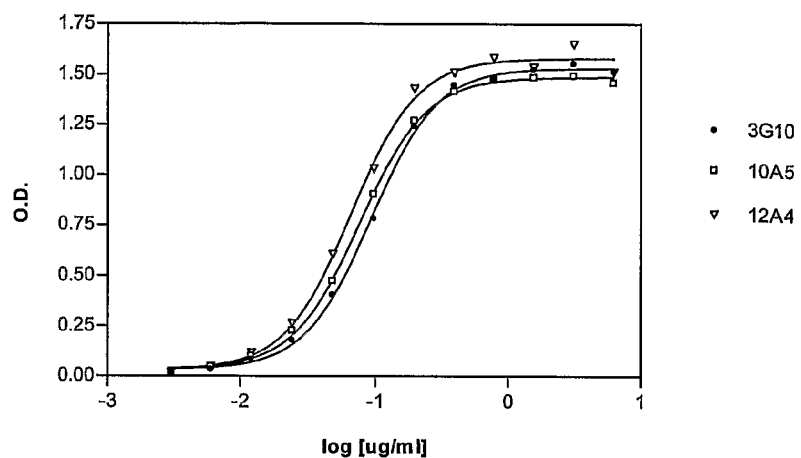
FIG. 34 shows the results of ELISA experiments demonstrating that the human monoclonal antibodies 3G10, 10A5, and 12A4, directed against human PD-L1, binds to PD-L1-Fc fusion protein.

An Fc-fusion protein of human PD-L1 was tested for binding against the anti-PD-L1 human monoclonal antibodies 3G10, 12A4, and 10A5. Standard ELISA procedures were performed. The anti-PD-L1 human monoclonal antibodies were added at different concentrations. Goat-anti-human IgG (kappa chain-specific) polyclonal antibody conjugated with horseradish peroxidase (HRP) was used as secondary antibody. The results are shown in FIG. 34. Each of the anti-PD-L11 human monoclonal antibodies 3G10, 12A4, and 10A5 bound with high specificity to PD-L1.

Example 4

Characterization of Anti-PD-L1 Antibody Binding to PD-L1 Expressed on the Cell Surface of Human and Monkey T Cells Anti-PD-L1 antibodies were tested by flow cytometry for binding to activated human or cynomolgus monkey T cells expressing PD-L1 on their surface.

Figure 35:
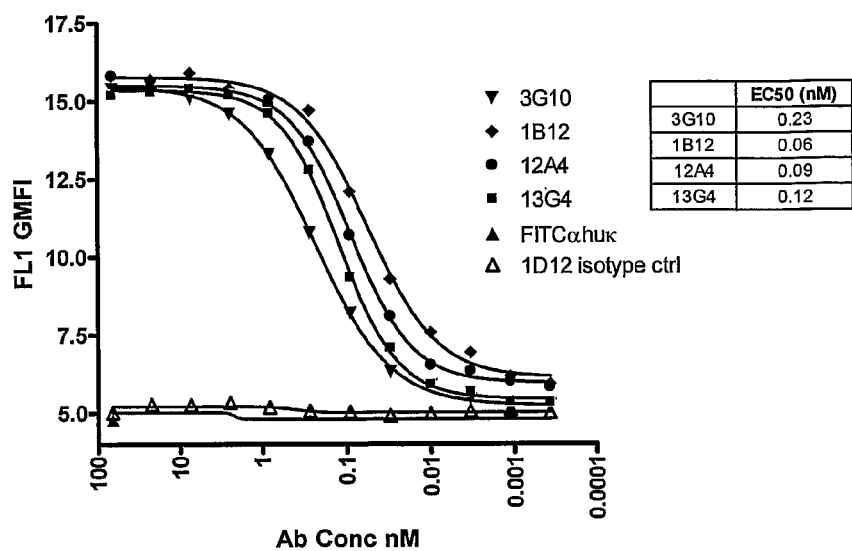
FIG. 35 shows the results of experiments demonstrating HuMab titration on stimulated human CD4+T cells.
Figure 36:
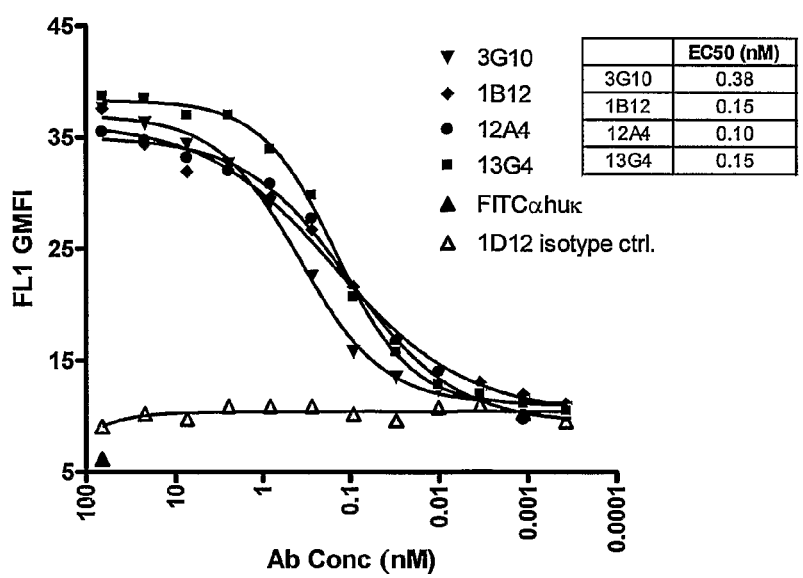
FIG. 36 shows the results of experiments demonstrating HuMab titration on stimulated cynomolgus PBMC.

Human or monkey T cells were activated by anti-CD3 antibody to induce PD-L1 expression prior to binding with a human anti-PD-L1 monoclonal antibody. Binding of the 3G10, 1B12, 13G4, and 12A4 anti-PD-L1 human monoclonal antibodies was assessed by incubating the activated cells with serial dilutions of the anti-PD-L1 human monoclonal antibodies. An isotype control antibody was used as a negative control. The cells were washed and binding was detected with a FITC-labeled anti-human Ig-kappa light chain Ab. Flow cytometric analyses were performed using a FACScalibur flow cytometer (Becton Dickinson, San Jose, Calif.). The results are shown in FIGS. 35 and 36. The anti-PD-L1 monoclonal antibodies 3G10, 1B12, 13G4, and 12A4 bound to activated human and monkey T cells. These data demonstrate that the anti-PD-L1 human monoclonal antibodies bind to human and cynomolgus monkey cell surface PD-L1.

Example 5

Characterization of Anti-PD-L1 Antibody Binding to PD-L1 Expressed on the Cell Surface of Human T Cells Anti-PD-L1 antibodies were tested for binding to activated human T cells expressing PD-L1 on their cell surface by flow cytometry.

Human T cells were activated by anti-CD3 antibody to induce PD-1, expression on T cells prior to binding with a human anti-PD-L1 monoclonal antibody. Binding of the 3G10, 10A5 and 12A4 anti-PD-L1 human monoclonal antibodies was assessed by incubating the activated T cells with the anti-PD-L1 human monoclonal antibodies at a concentration of 20 µg/ml. An isotype control antibody was used as a negative control. The cells were washed and binding was detected with a FITC-labeled anti-human IgG Ab. Flow cytometric analyses were performed using a FACScalibur flow cytometry (Becton Dickinson, San Jose, Calif.). The results are shown in FIGS. 37A (HuMAb 3G10), 37B (HuMAb 10A5) and 37C (HuMAb 12A4). The anti-PD-L1 monoclonal antibodies 3G10, 10A5, and 12A4 bound to activated human T cells (bold line), as shown in histogram plots compared to control (light line). These data demonstrate that the anti-PD-L1 human monoclonal antibodies bind to human cell surface PD-L1.

Example 6

Binding Specificity by Flow Cytometry

Figure 38:
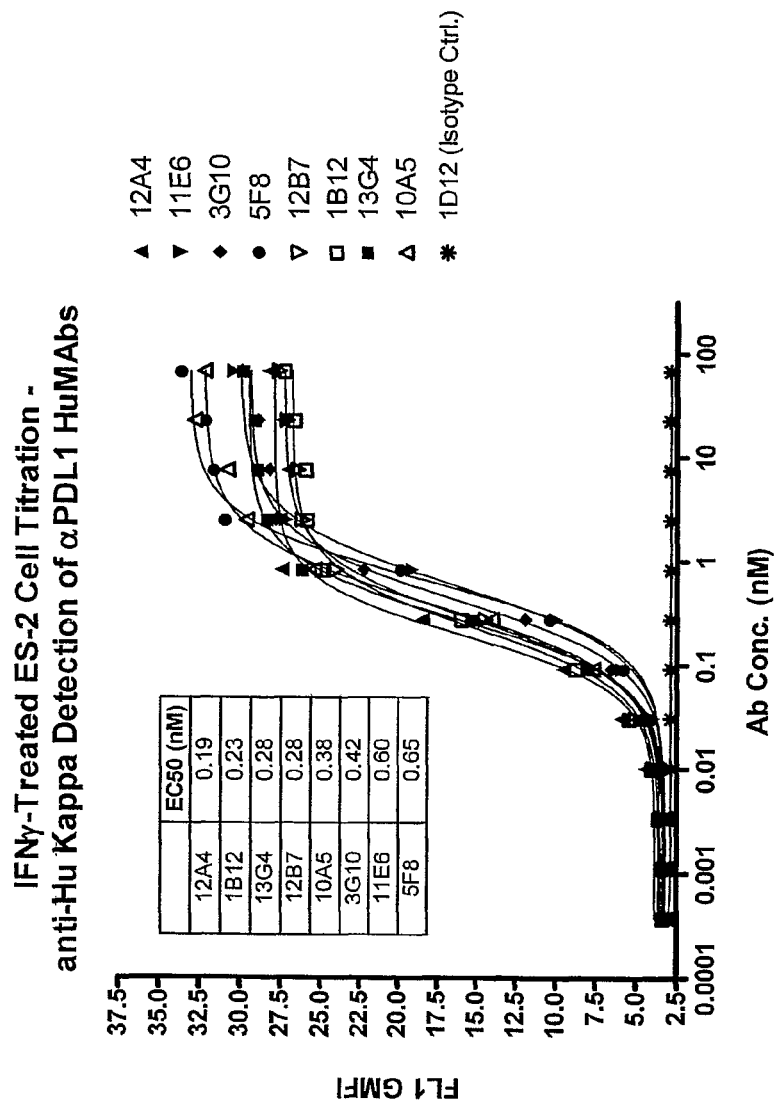
FIG. 38 demonstrates binding of HuMabs to ES-2 cells.

The ES-2 human ovarian carcinoma cell line that expresses human PD-L1 at the cell surface was used to determine the specificity of PD-L1 human monoclonal antibodies by flow cytometry. ES-2 cells were treated overnight with 500 IU/mL of recombinant hIFN-γ to increase PD-L1 expression over the basal level. Binding of the 12A4, 1B12, 3G10, 10A5, 12B7, 13G4, 11B6, and 5F8 anti-PD-L1 human monoclonal antibodies was assessed by incubating the induced cells with serial dilutions of the anti-PD-L1 human monoclonal antibody. The cells were washed and binding was detected with a PB-labeled anti-human IgG Ab. Flow cytometric analyses were performed using a FAC-Scalibur flow cytometer (Becton Dickinson, San Jose, Calif.). The binding was compared to isotype control antibody. The results are shown in FIG. 38. The anti-PD-L1 human monoclonal antibodies 12A4, 1B12, 3G10, 10A5, 12B7, 13G4, 11E6, and 5F8 bound to the hIFN-γ-induced ES-2 cells in a concentration dependent manner. These data demonstrate that the anti-PD-L1 human monoclonal antibodies specifically bind to cell surface PD-L1.

Example 7

Effect of Human Anti-PD-L1 Antibodies on Cell Proliferation and Cytokine Production in a Mixed Lymphocyte Reaction A mixed lymphocyte reaction was employed to demonstrate the effect of blocking the PD-L1/PD-1 pathway to lymphocyte effector cells. T cells in the assay were tested for proliferation, IFN-γ secretion and IL-2 secretion in the presence or absence of an anti-PD-L1 human monoclonal antibody.

Figure 39A:
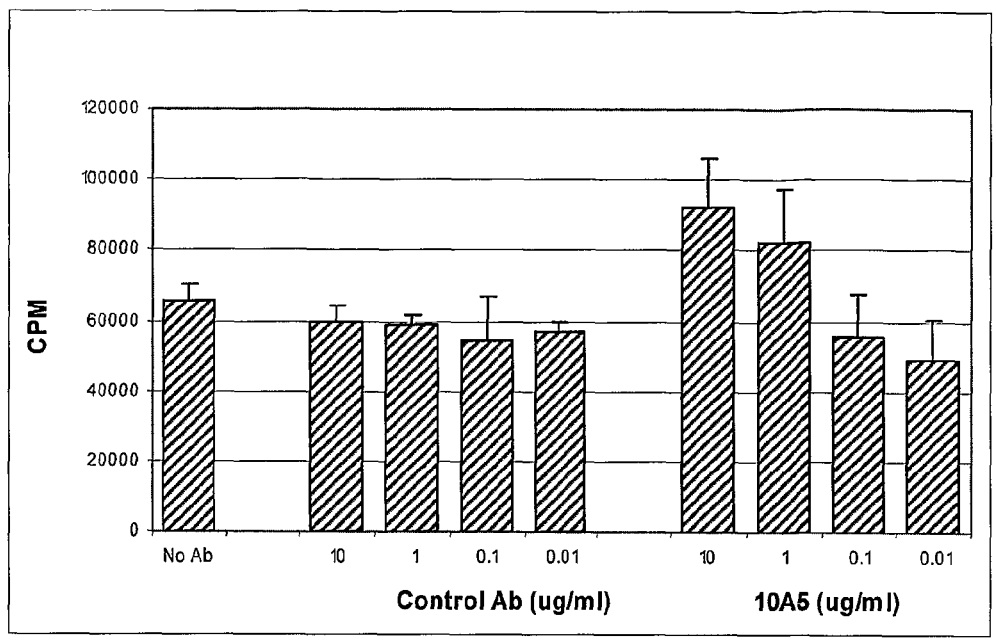
FIGS. 39A-39D show the results of experiments demonstrating that human monoclonal antibodies against human PD-L1 promote T-cell proliferation, IFN-γ secretion and IL-2 secretion in a mixed lymphocyte reaction assay.
Figure 39B:
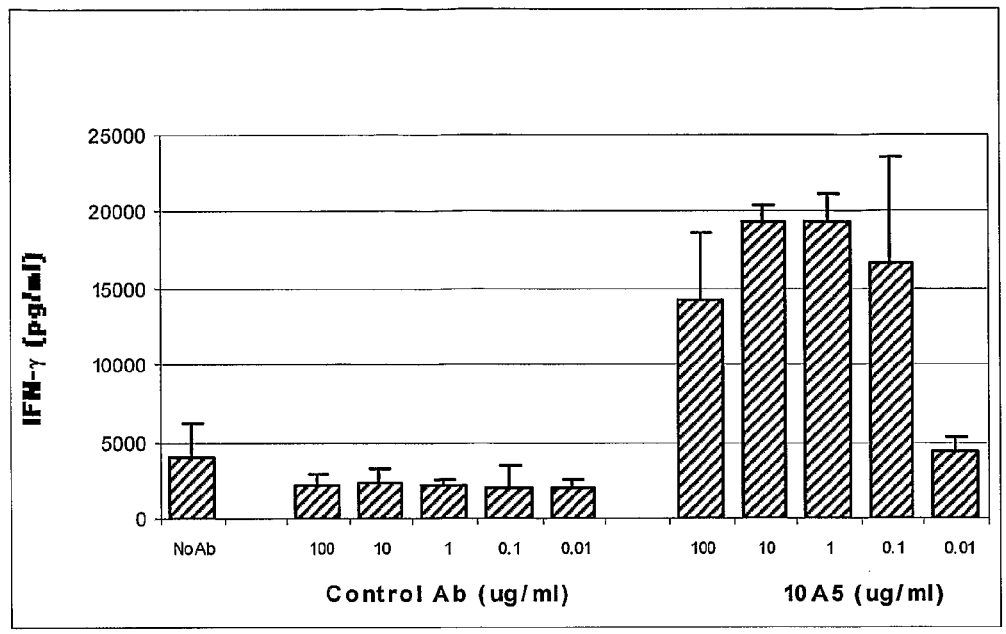
Figure 39C:
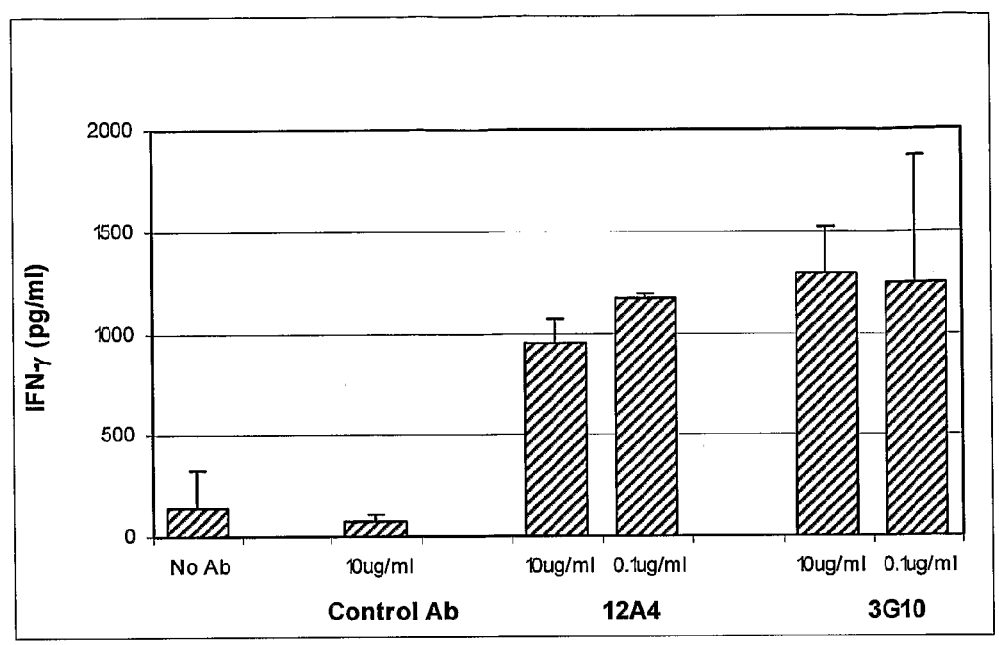
Figure 39D:
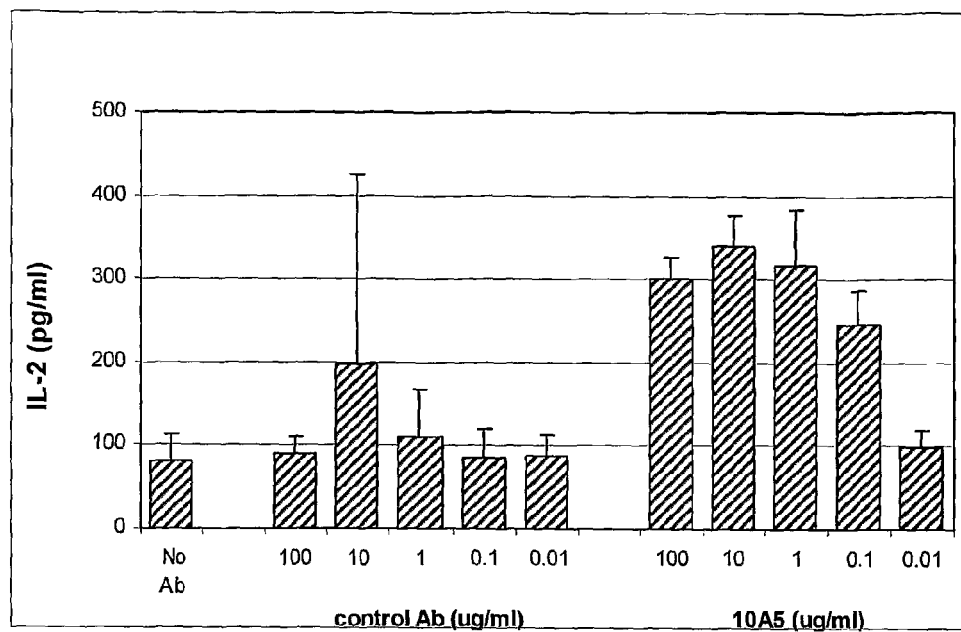

Human CD4+T-cells were purified from PBMC using a CD4+ positive selection kit (Dynal Biotech). Dendritic cells were derived from purified monocytes cultured with 1000 U/ml of L-4 and 500 U/ml of GM-CSF (R&D Biosystems) for seven days. Monocytes were prepared using a monocyte negative selection kig (Mitenyi Biotech). Each culture contained $10^5$ purified T-cells and $10^6$ allogeneic dendritic cells in a total volume of 200 µl. Anti-PD-L1 monoclonal antibody 10A5, 12A4, or 3G10 was added to each culture at different antibody concentrations. Either no antibody or an isotype control antibody was used as a negative control. The cells were cultured for 5 days at 37° C. After day 5, 100 µl of medium was taken from each culture for cytokine measurement. The levels of IFN-γ and IL-2 were measured using OptEIA ELISA kits (BD Biosciences). The cells were labeled with $^3$H-thymidine, cultured for another 18 hours, and analyzed for cell proliferation. The results are shown in FIGS. 39A (T cell proliferation), 39B (IFN-γ secretion using HuMAb 10A5), 39C (IFN-γ secretion using HuMAb 12A4 or 3G10) and 39D (IL-2 secretion). The anti-PD-L1 human monoclonal antibody 10A5 promotes T-cell proliferation, IFN-γ secretion and IL-2 secretion in a concentration dependent manner. The anti-PD-L1 human monoclonal antibodies 12A4 and 3G10 also showed an increase in IFN-γ secretion. In contrast, cultures containing the control antibody did not show an increase in T cell proliferation, IFN-γ or IL-2 secretion.

In a separate experiment, an allogeneic mixed lymphocyte reaction (MLR) was employed to demonstrate the effect of blocking the PD-L1/PD-1 pathway in lymphocyte effector cells. T cells in the assay were tested for proliferation and IFN-γ secretion in the presence or absence of an anti-PD-L1 human monoclonal antibody or isotype control antibody.

Figure 40:
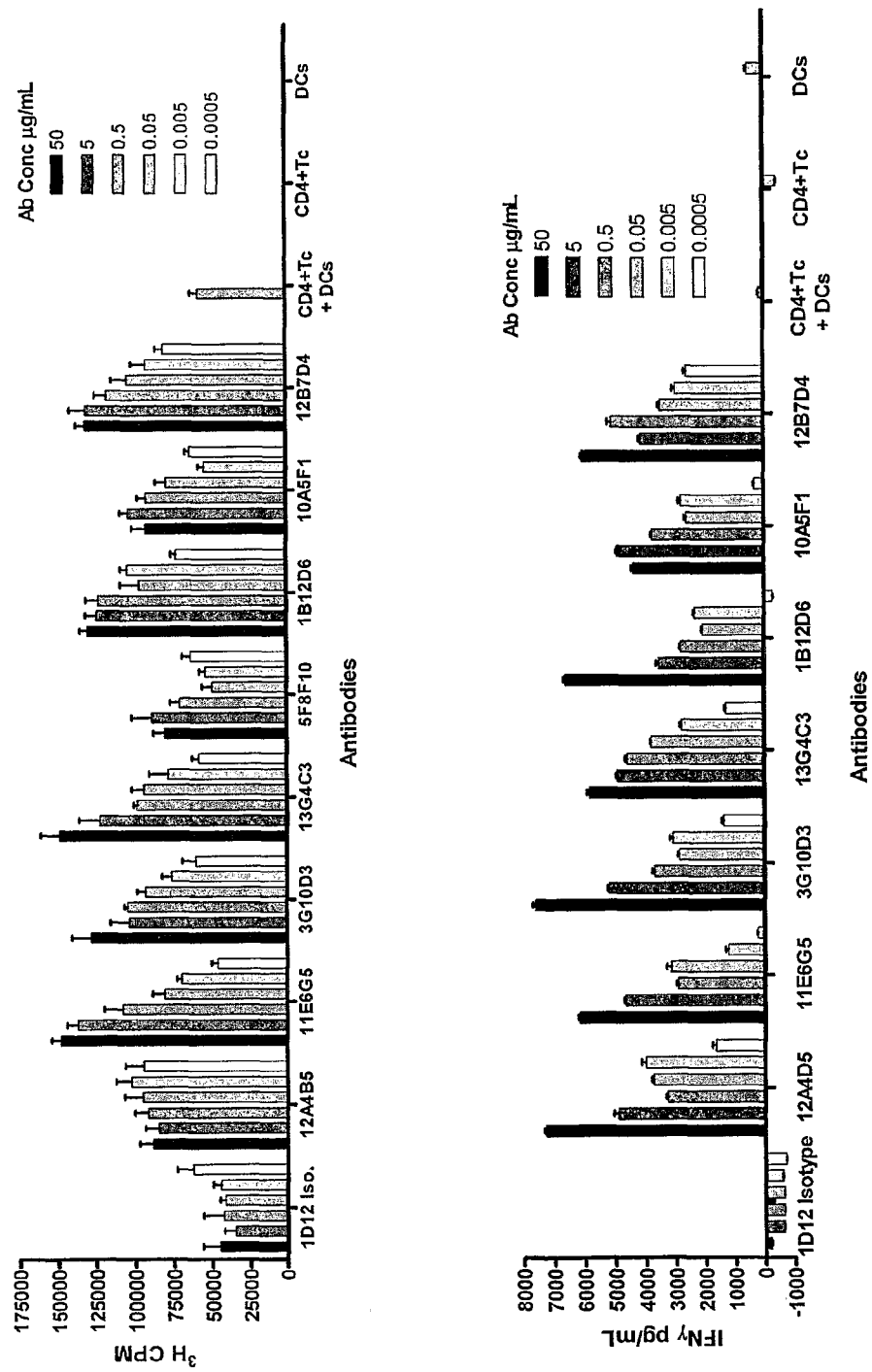
FIG. 40 demonstrates the effect of human anti-PD-L1 antibody on proliferation and IFN-γ secretion in the MLR using allogeneic dendritic cells and T cells (CD4+ effector T cells) Dendritic Cells.

Human CD4+T-cells were purified from PBMC using a CD4+ negative selection kit (Miltenyi). Monocytes were prepared using a monocyte negative selection kit (Mitenyi Biotech). Dendritic cells were derived from purified monocytes cultured with 1000 U/ml of IL-4 and 500 U/ml of GM-CSF (R&D Biosystems) for seven days. Each MLR culture contained $10^5$ purified T-ells and $10^4$ allogeneic dendritic cells in a total volume of 200 µl. Anti-PD-L1.1 monoclonal antibody 12A4, 11E6, 3G10, 13G4, 1B12, 10A5, and 12B7 were added to each culture at different antibody concentrations. Either no antibody or an isotype control antibody was used as a negative control. The cells were cultured for 5 days at 37° C. On day 5, 50 µl of medium was taken from each culture for cytokine measurement and replaced with an equal volume of culture medium containing 1 µCi of $^3$H-thymidine. The cells were cultured for another 18 hours, harvested, and analyzed for cell proliferation. The levels of IFN-γ in the culture fluid were measured using an OptEIA hIFN-γ ELISA kit (BD Biosciences). The results are shown in FIG. 40. The anti-PD-L1 human monoclonal antibodies promote T-cell proliferation and IFN-γ secretion in a concentration-dependent manner. In contrast, cultures containing the control antibody did not show an increase in T cell proliferation or IFN-γ secretion.

Example 8

Effect of Human Anti-PD-L1 Antibody on Function of T Regulatory Cells

T regulatory cells (CD4+, CD25+) are lymphocytes that suppress the immune response. The effect of the addition of T regulatory cells on proliferation and IFN-γ secretion in the allogeneic dendritic cell and T cell MLR in the presence or absence of an anti-PD-L1 human monoclonal antibody was tested.

Figure 41A:
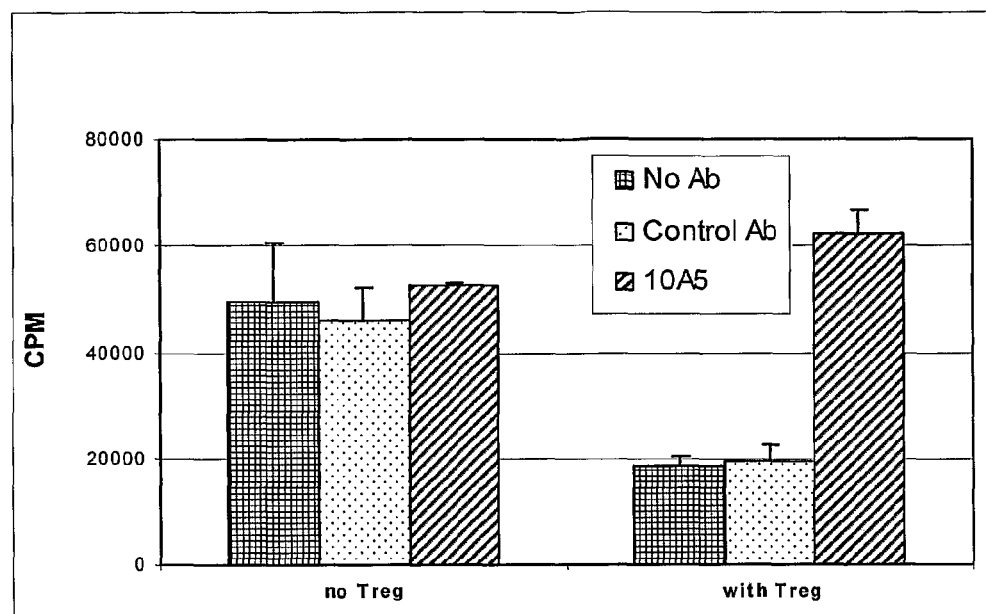
FIGS. 41A and 41B show the results of experiments demonstrating that human monoclonal antibodies against human PD-L1 promote T-cell proliferation and IFN-γ secretion in MLR containing T regulatory cells.
Figure 41B:
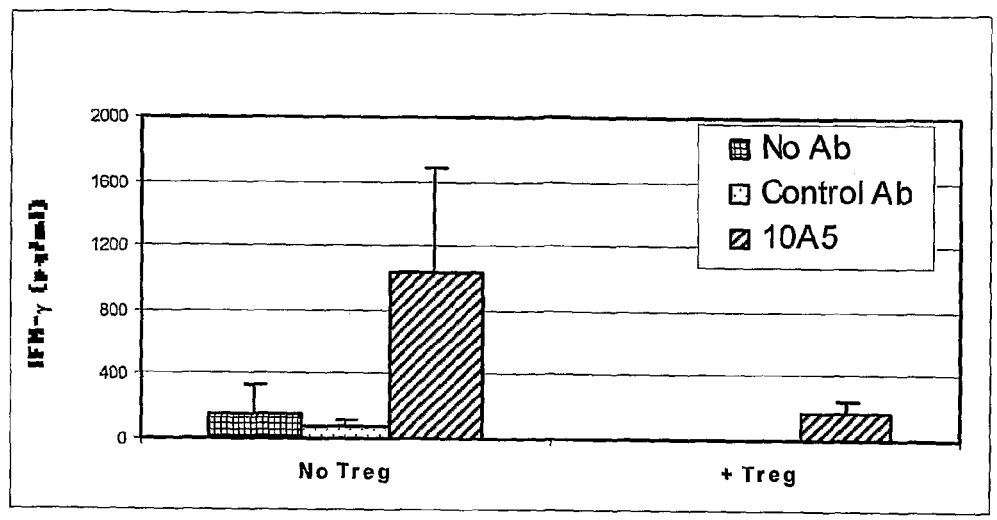
Figure 42:
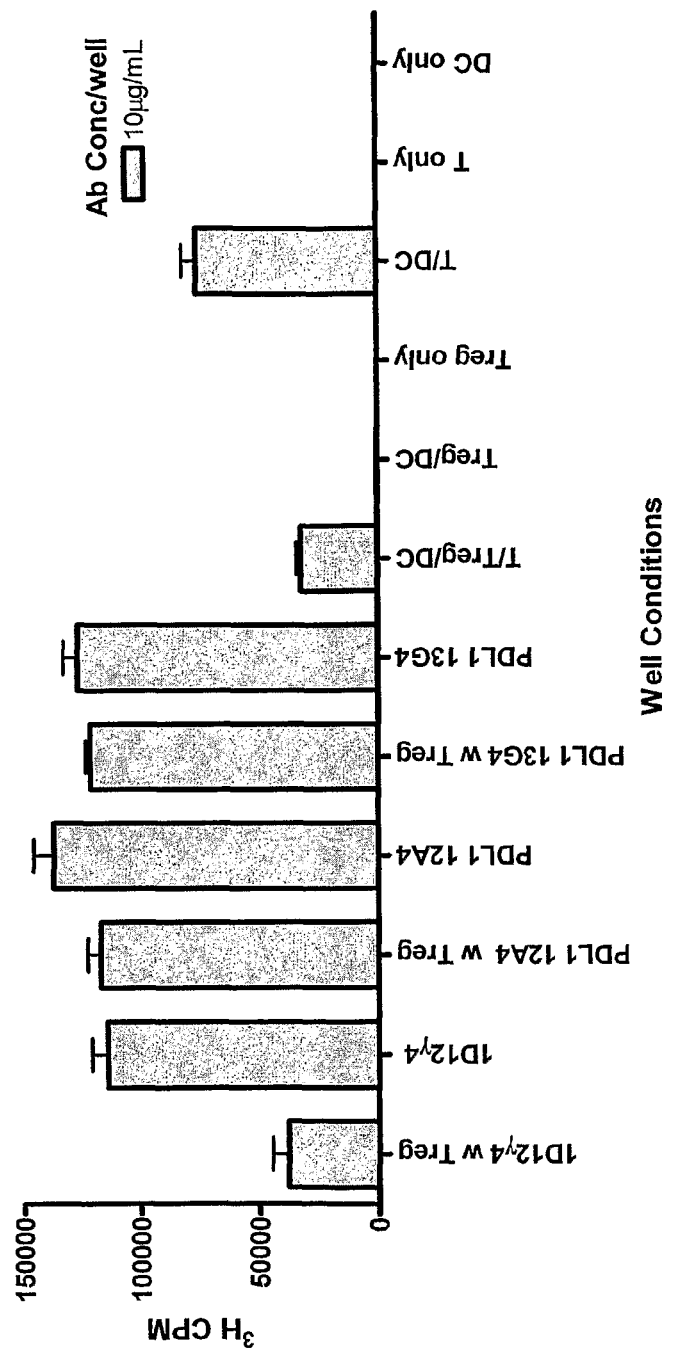
FIG. 42 demonstrates the results of anti-PD-L1 antibodies on cell proliferation in a Mixed Lymphocyte Reaction in the presence of regulatory T cells.
Figure 43:
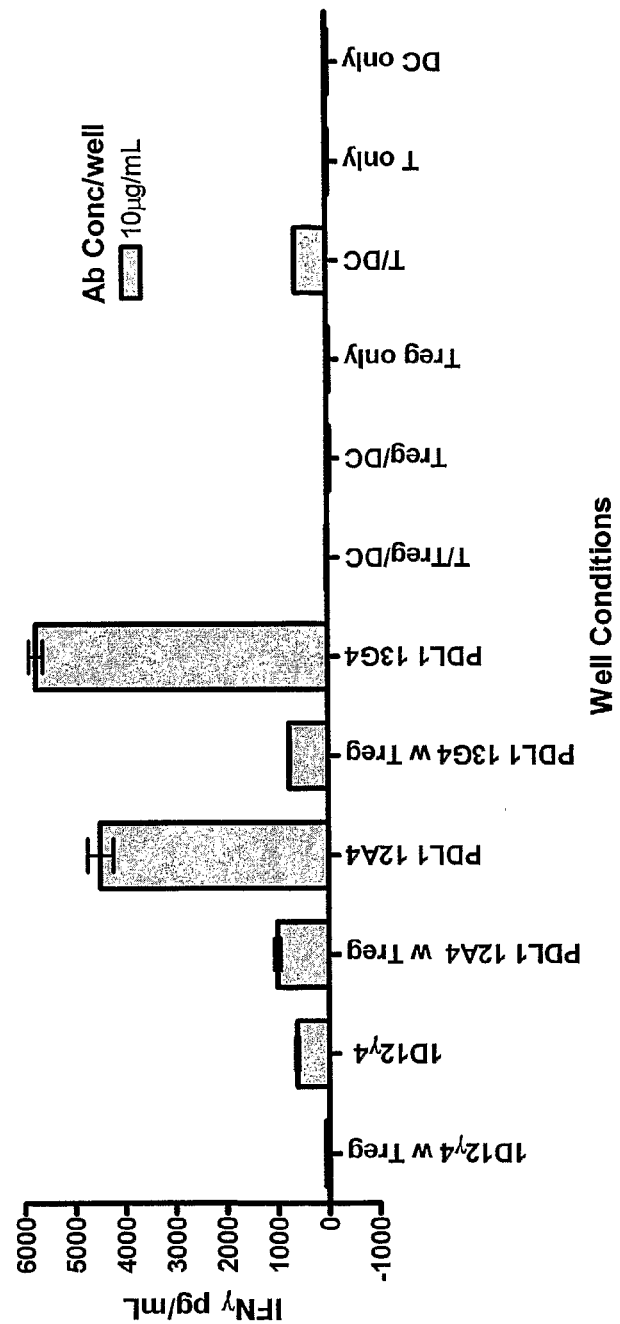
FIG. 43 demonstrates the results of anti-PD-L1 antibodies on cytokine production in a Mixed Lymphocyte Reaction in the presence of regulatory T cells.

T regulatory cells were purified from PBMC using a CD44CD25+ regulatory T cell isolation kit (Miltenyi Biotec). T regulatory cells were added into a mixed lymphocyte reaction (see above) containing purified CD4+CD25-T cells and allogeneic dendritic cells in a 2:1 ratio of CD4+CD25- to T regulatory cells. Anti-PD-L1 monoclonal antibody 10A5 was added to each culture at a concentration of 10 µg/ml. Either no antibody or an isotype control antibody was used as a negative control. The cells were cultured for 5 days at 37'C at which time the supernatants were analyzed for IFN-γ secretion using a Beadlyte cytokine detection system (Upstate). The cells were labeled with $^3$H-thymidine, cultured for another 18 hours, and analyzed for cell proliferation. The results are shown in FIGS. 41A (T cell proliferation) and 41B (IFN-γ secretion). The addition of anti-PD-L1 human monoclonal antibody 10A5 promotes both T cell proliferation and IFN-γ secretion in cell cultures of allogeneic dendritic cells, T cells and T regulatory cells, indicating that anti-PD-L1 antibodies can reverse the effect of T regulatory cells in the allogeneic DC-T cell-MLR In a separate experiment, human anti-PD-L1 antibodies 12A4 and 13G4, and a control antibody 1D12, were tested in the MLR assay with T regulatory cells. The results are shown in FIGS. 42 (T cell proliferation) and 43 (IFN-γ secretion). The addition of anti-PD-L) human monoclonal antibodies 12A4 or 13G4 partially reverses the suppression of both T cell proliferation and IFN-γ secretion in cell cultures of allogeneic dendritic cells and T cells containing T-regulatory cells, indicating that anti-PD-L1 antibodies may have an effect on T-regulatory cells.

Example 9

Figure 44:
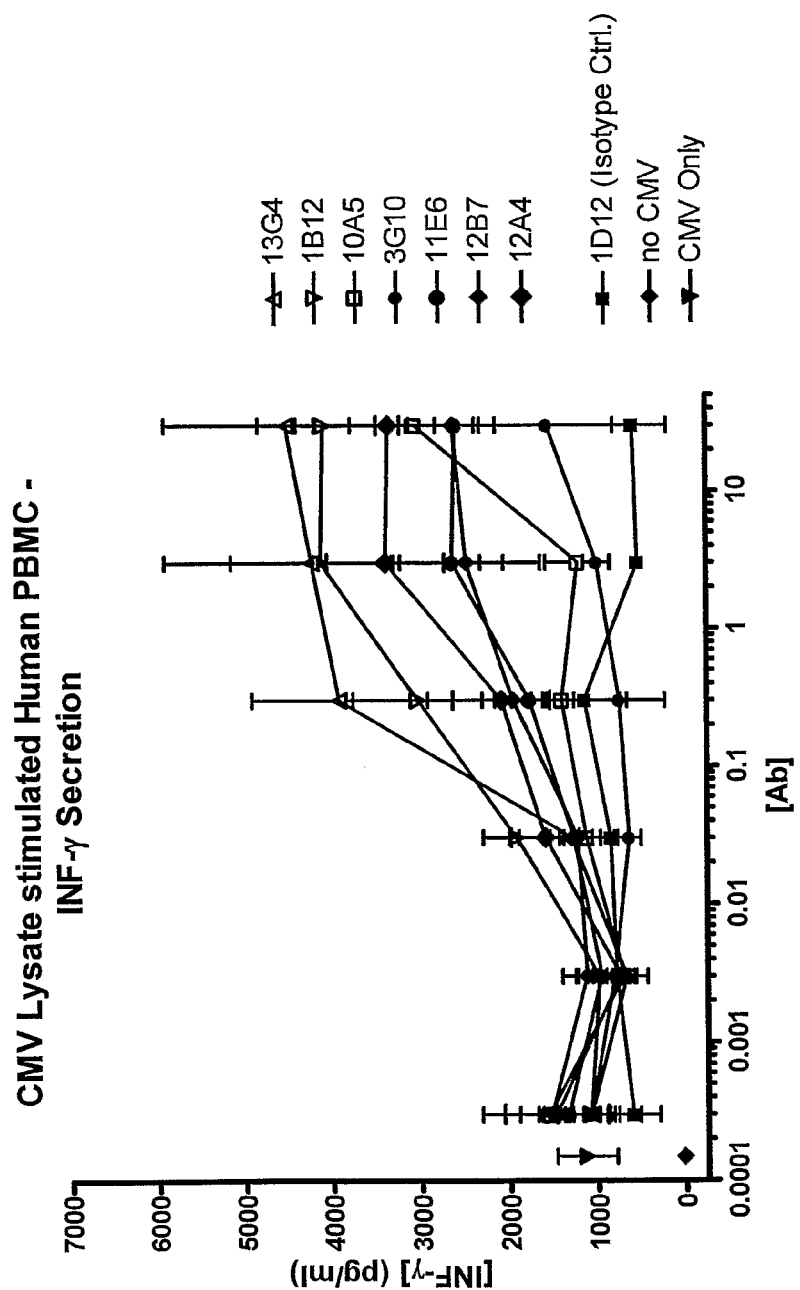
FIG. 44 demonstrates the results of anti-PD-L1 antibodies on CMV lysate stimulated human PBMC IFN-γ secretion.

Effect of Anti-PD-1 Antibodies on Cytokine Secretion by Viral Antigen-Stimulated PBMC Cells from a Positive CMV Responsive Donor CMV antigen-responsive human PBMC (Astarte Biologics, Redmond, Wash.) were cultured at 2e5 cells/well in flat bottom TC-treated 96 well plates, in the presence of 0.5 ug/ml CMV lysate (Astarte Biologics)+/− titrated anti-PD-L1 antibodies. AIM-V medium (Invitrogen) supplemented with heat-inactivated FBS (10% final) was used at a total volume of 200 ul/well. The cells were cultured for 4 days at 37° C., 5% $CO_2$ at which time culture supernatant was harvested for determination of secreted interferon-γ by ELISA (OptEIA hIFN-γ ELISA kit-BD Biosciences). The results are shown in FIG. 44. The anti-PD-L1 human monoclonal antibodies promote IFN-γ secretion by CMV-specific T-cells in a dose-dependent manner. The most robust response was generated by antibodies 13G4, 1B12, and 12A4 compared to isotype control. These results shows that anti-PD-L1 HuMAbs can stimulate IFN-γ release in a memory T cell response from PBMC cells previously stimulated against an antigen.

Example 10

Blocking of PD-L1 Ligand Binding to PD-1 by Human Anti-PD-L1 Antibodies

Anti-PD-L1 human monoclonal antibodies were tested for the ability to block binding of the ligand PD-L1 to PD-1 expressed on transfected CHO cells by using a cell cytometry assay.

Figure 45:
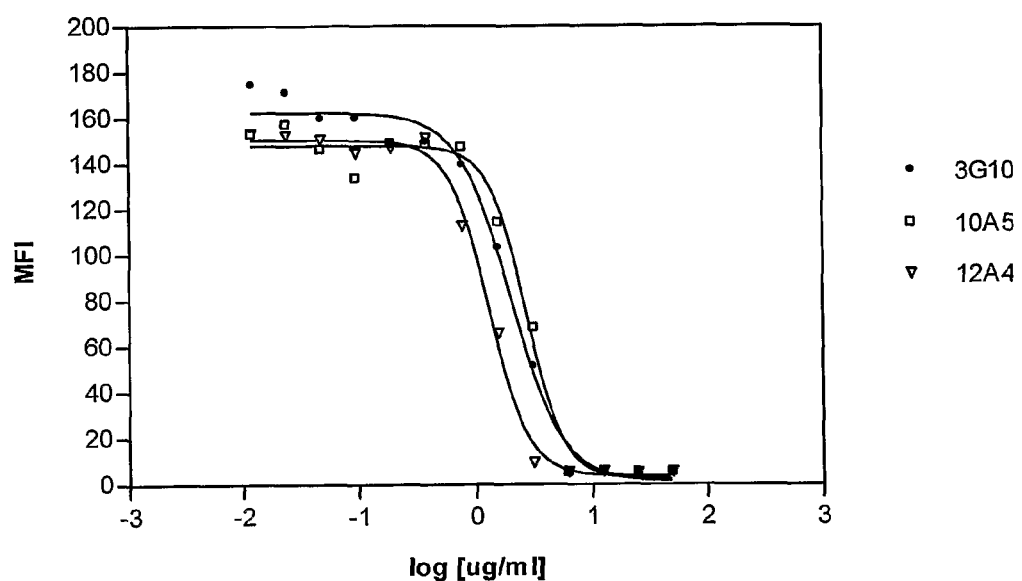
FIG. 45 shows the results of flow cytometry experiments demonstrating that human monoclonal antibodies against human PD-L1 block the binding of PD-L1 to CHO transfected cells expressing PD-1.

PD-1 expressing CHO cells were suspended in FACS buffer (PBS with 4% fetal calf serum). Various concentrations of the anti-PD-L1 HuMAbs 3G10, 10A5 or 12A4 was added to the cell suspension tubes at 4° C. for 30 minutes, followed by addition FITC-labeled PD-L1 fused to an immunoglobulin Fc-region. Flow cytometric analyses were performed using a FACScalibur flow cytometer (Becton Dickinson, San Jose, Calif.). The results are depicted in FIG. 45. The anti-PD-L1 monoclonal antibodies 3G10, 10A5, and 12A4 blocked binding of PD-L1 to CHO cells transfected with human PD-1, as measured by the mean fluorescent intensity (MFI) of staining. These data demonstrate that the anti-PD-L1 HuMAbs block binding of PD-L1 ligand to cell surface PD-1.

Example 11

Inhibition of the Binding of Soluble PD-1 to Cell-Surface PD-L1 by Human Anti-PD-L1 Antibodies Anti-PD-L1 human monoclonal antibodies were tested for the ability to block binding of a soluble dimeric version of the PD-1 receptor (PD-1-hFc) to PD-L1 expressed on hIFN-γ-induced BS-2 human ovarian carcinoma cells using a flow cytometry assay. The blocking was compared to isotype control antibody.

Figure 46:
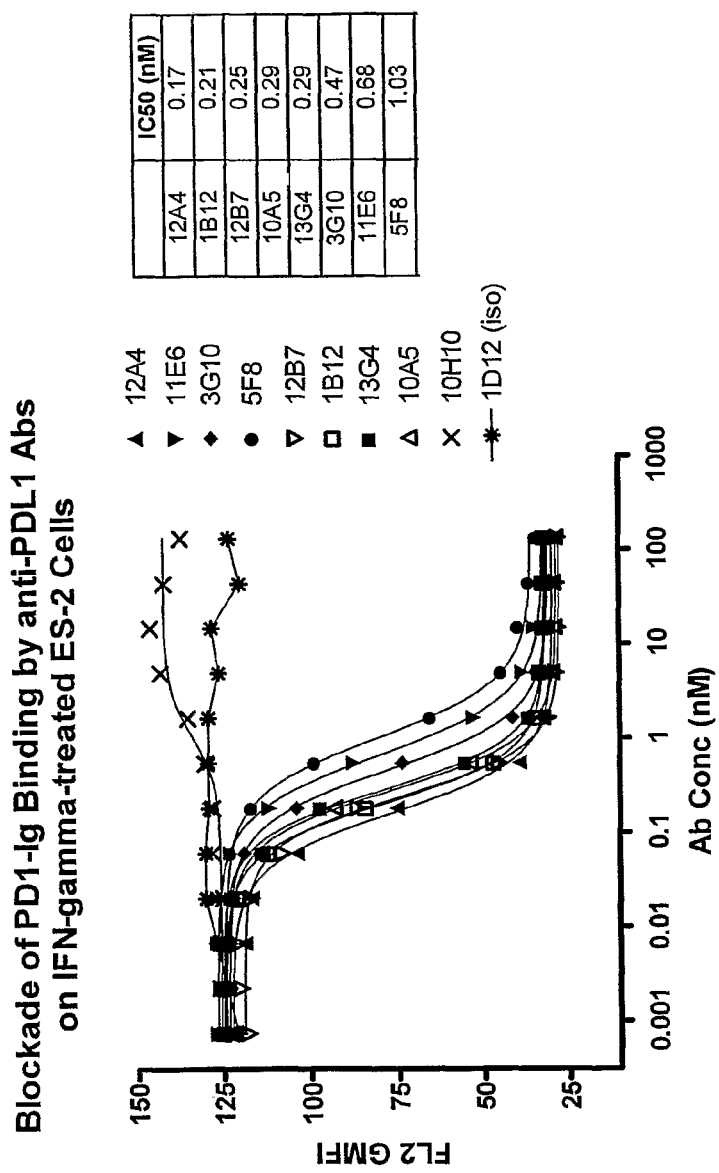
FIG. 46 shows that anti-PD-L1 antibodies block binding of PD-1 to IFNγ treated ES-2 cells.

ES-2 cells were induced overnight with 500 IU/mL of hIFN-γ to upregulate hPD-L1 cell surface expression. Induced cells were suspended in FACS buffer. Serial dilutions of the anti-PD-L1 HuMAbs 12A4, 1B12, 3G10, 10A5, 12B7, 13G4, 11E6, and 5F8 were added to the cell suspension tubes at 4° C. for 30 minutes, followed by two washes to remove unbound antibody. Next PD-1-hFc protein was added at a constant 2 ug/mL to all wells at 4° C. for 30 minutes, followed by two washes to remove unbound PD-1-hFc. Next bound PD-1-Fc was detected on the FS-2 cells by addition of biotinylated-non-blocking anti-PD-1 HuMab 26D5, which binds to PD-1 when bound to PD-L1, at 4° C. for 30 minutes, followed by two washes to remove unbound antibody. Finally, bound 26D5 antibody was detected by addition of streptavidin-PE conjugate at 4° C. for 30 minutes, followed by two washes to remove unbound conjugate. Flow cytometric analysis was performed using a FACScalibur flow cytometer (Becton Dickinson, San Jose, Calif.). The results are depicted in FIG. 46. The anti-PD-L1 monoclonal antibodies 12A4, 1B12, 3G10, 1A5, 12B7, 13G4, 11E6, and 5F8 blocked binding of PD-1 to ES-2 cells that express human PD-L1, as measured by the geometric mean fluorescent intensity (GMFI) of staining. These data demonstrate that the anti-PD-L1 HuMAbs block binding of soluble PD-1 receptor to cell surface PD-L1.

Example 12

Treatment of In Vivo Tumor Model Using Anti-PD-L1 Antibodies

Mice implanted with a cancerous tumor are treated in vivo with anti-PD-L1 antibodies to examine the in vivo effect of the antibodies on tumor growth. For the tumor studies, female AJ mice between 6-8 weeks of age (Harlan Laboratories) are randomized by weight into 6 groups. The mice are implanted subcutaneously in the right flank with $2\times10^6$ SAl/N fibrosarcoma cells dissolved in 200 μl of DMEM media on day 0. The mice are treated with PBS vehicle, or anti-PD-L1 antibodies at 10 mg/kg. The animals are dosed by intraperitoneal injection with approximately 200 μl of PBS containing antibody or vehicle on days 1, 4, 8 and 11. Each group contains 10 animals and the groups consist of: (i) a vehicle group, (ii) control mouse IgG, and (iii) an anti-PD-L1 antibody. The mice are monitored twice weekly for tumor growth for approximately 6 weeks. Using an electronic caliper, the tumors are measured three dimensionally (height×width×length) and tumor volume is calculated. Mice are euthanized when the tumors reached tumor end point (1500 $mm^3$) or show greater than 15% weight loss.

Example 13

Figure 47:
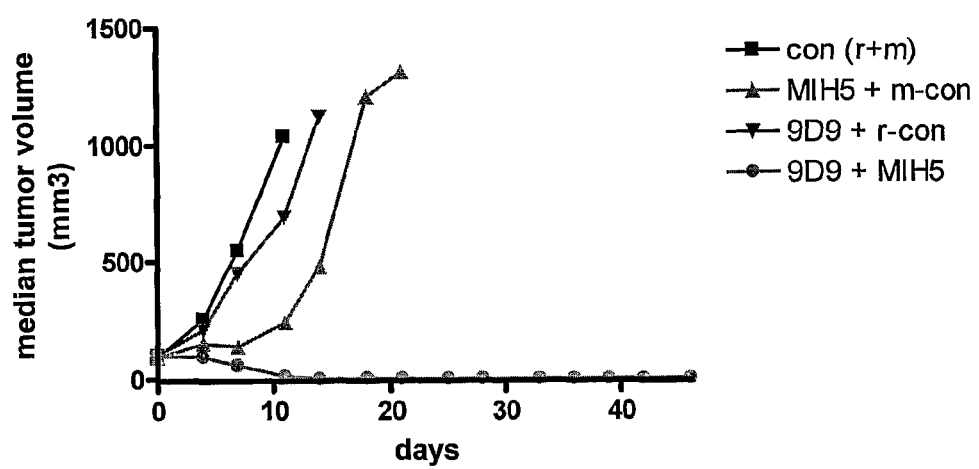
FIG. 47 shows the effect of anti-PD-L1 antibodies on tumor growth in vivo.

In Vivo Efficacy of Combination Therapy (Anti-CTLA-4 and Anti-PD-L1 Antibodies) on Tumor Establishment and Growth MC38 colorectal cancer cells (available from Dr. N. Restifo, National Cancer Institute, Bethesda, Md.; or Jeffrey Schlom, National Institutes of Health, Bethesda, Md.) were implanted in C57BL/6 mice ($2\times10^6$ cells/mouse) and selected for treatment when tumors reached a size of 100-200 $mm^3$). On day 0 (i.e., the first day of treatment), each of four groups of 10 mice each was injected intraperitoneally (IP) with one of the following (1) 10 mg/kg mouse IgG and 10 mg/kg of rat IgG (control), (2) 10 mg/kg anti-CTLA-4 monoclonal antibody 9D9 (mouse anti-mouse CTLA-4, obtained from J. Allison, Memorial Sloan-Kettering Cancer Center, New York, N.Y.) and 10 mg/kg rat IgG, (3) anti-PD-L1 monoclonal antibody MIH5 (rat anti-mouse PD-L1, eBioscience) and 10 mg/kg mouse IgG, or (4) 10 mg/kg anti-CTLA-4 antibody 9D9 and 10 mg/kg anti-PD-L1 antibody MIH5. Antibody injections were then further administered on days 3 and, 6. Using an electronic caliper, the tumors were measured three dimensionally (height×width×length) and tumor volume was calculated. Mice were euthanized when the tumors reached a designated tumor endpoint. The results are shown in FIG. 47.

This study indicates that, in the MC38 murine tumor model, anti-PD-L1 antibody treatment alone has a modest effect on tumor growth resulting in a delay of tumor growth while anti-CTLA-4 has little effect in this model. However, the combination treatment of CTLA-4 antibody and PD-L1 antibody has a significantly greater effect on tumor growth and results in tumor free mice.

Example 14

Immunohistochemistry Using Anti-PD-L1 Antibodies

To assess the tissue binding profiles of HuMab anti-PD-L1, unmodified 12A4, 13G4, 3G10 and 12B7 were examined in a panel of normal (non-neoplastic) human tissues, Including spleen, tonsil, cerebrum, cerebellum, heart, liver, lung, kidney, pancreas, pituitary, skin, and small intestine, as well as lung carcinoma tissues (1 sample/each). ES-2 cells were used as positive control. Hu-IgG$_1$ and Hu-IgG$_4$ were used as isotype control antibodies.

Snap frozen and OCT embedded normal and tumor tissues were purchased from Cooperative Human Tissue Network (Philadelphia, Pa.) or National Disease Research Institute (Philadelphia, Pa.). Cryostat sections at 5 µm were fixed with acetone for 10 min at room temperature, and stored at −80° C. until use. A Medarex developed immunohistochemistry protocol was performed using unmodified HuMab anti-PD-L1 by pre-complex of the primary antibodies (12A4, 13G4, 3G10 and 12B7) and secondary antibody (FITC conjugated Fab fragment of goat anti-Hu-IgG. Jackson ImmunoResearch Laboratories. West Grove, Pa.) before applying onto the sections. Briefly, 1 µg/ml or 5 µg/ml of the un-conjugated primary antibodies were mixed with 3 fold excess of secondary antibody respectively and incubated for 30 min at room temperature, and then excess human gamma globulin was added for another 30 min to block the unbound secondary antibody. In parallel, isotype control antibodies Hu-IgG$_1$ or Hu-IgG$_4$ were pre-complexed in the same manner. Slides were washed with PBS (Sigma, St. Louis, Mo.) twice, and then incubated with peroxidase block supplied in Dako EnVision+System (Dako. Carpinteria, Calif.) for 10 minutes. After two washes with PBS, slides were incubated with Dako protein block to block the non-specific binding sites. Subsequently, the pre-complex of primary antibodies or isotype controls were applied onto sections and incubated for 1 hr. Following three washes with PBS, slides were incubated with mouse anti-FITC antibody (20 µg/ml. Sigma) for 30 min. After another three washes with PBS, the slides were incubated with the peroxidase-conjugated anti-mouse IgG polymer supplied in the Dako EnVision+System for 30 min. Finally, slides were washed as above and reacted with DAB substrate-chromogen solution supplied in the Dako EnVision+System for 6 min. Slides were then washed with deionized water, counterstained with Mayer's hematoxylin (Dako), dehydrated, cleared and coverslipped with Permount (Fischer Scientific, Fair Lawn, N.J.) following routine histological procedure.

Weak to moderate staining was observed in ES-2 cells, as well as in tumor cells of lung carcinoma tissues. In tonsil sections, strong staining was seen in crypt epithelium that is heavily infiltrated by lymphoid cells, but not in the mucous stratified squamous epithelial cells. Moderate staining was seen in some cells in the inter-follicular region, and very weak staining was seen in scattered large cells (dendritic reticulum-like cells) in the germinal center. In lung, weak staining was found in alveoli macrophages. The staining patterns in tonsil and lung tissues were similarly seen in immunohistochemistry sections using commercial anti-PD-L1 mAb (eBiosciences, San Diego, Calif.). There was overall less Intense staining by HuMabs, especially for the staining in the germinal centers. In spleen, diffuse weak immunoreactivity in red pulp was slightly above the background staining. In addition, weak to moderate staining was displayed in Kupffer-like cells in liver and scattered cells in Peyer's patch, as well as in scattered macrophage-like cells and fibroblasts mainly in focal region of the muscularis externa of small intestine.

In cerebellum, cerebrum, heart, kidney, pancreas, pituitary and skin tissues, no meaningful staining was observed when stained with all four anti-PD-L1 HuMabs. No evident difference in staining was noted among those four antibodies except 12B7 and/or 3G10 displayed slightly stronger staining in liver and ES-2 cells.

| PD-L1 Antibody Summary | | | |
|---|---|---|---|
| SEQ ID NO: | SEQUENCE | SEQ ID NO: | SEQUENCE |
| 1 | VH a.a. 3G10 | 26 | VH CDR1 a.a. 1B12 |
| 2 | VH a.a. 12A4 | 27 | VH CDR1 a.a. 7H1 |
| 3 | VH aa 10A5 | 28 | VH CDR1 a.a. 11E6 |
| 4 | VH a.a. 5F8 | 29 | VH CDR1 a.a. 12B7 |
| 5 | VH a.a. 10H10 | 30 | VH CDR1 a.a. 13G4 |
| 6 | VH a.a. 1B12 | | |
| 7 | VH a.a. 7H1 | 31 | VH CDR2 a.a. 3G10 |
| 8 | VH a.a. 11E6 | 32 | VH CDR2 a.a. 12A4 |
| 9 | VH a.a. 12B7 | 33 | VH CDR2 a.a. 10A5 |
| 10 | VH a.a. 13G4 | 34 | VH CDR2 a.a. 5F8 |
| | | 35 | VH CDR2 a.a. 10H10 |
| 11 | VK a.a. 3G10 | 36 | VH CDR2 a.a. 1B12 |
| 12 | VK a.a. 1244 | 37 | VH CDR2 a.a. 7H1 |
| 13 | VK a.a. 10A5 | 38 | VH CDR2 a.a. 11E6 |
| 14 | VK a.a. 5F8 | 39 | VH CDR2 a.a. 12B7 |
| 15 | VK a.a. 10H10 | 40 | VH CDR2 a.a. 13G4 |
| 16 | VK a.a. 1B12 | | |
| 17 | VK a.a. 7H1 | 41 | VH CDR3 a.a. 3G10 |
| 18 | VK a.a. 11E6 | 42 | VH CDR3 a.a. 12A4 |
| 19 | VK a.a. 12B7 | 43 | VH CDR3 a.a. 10A5 |
| 20 | VK a.a. 13G4 | 44 | VH CDR3 a.a. 5F8 |
| | | 45 | VH CDR3 a.a. 10H10 |
| 21 | VH CDR1 a.a. 3G10 | 46 | VH CDR3 a.a. 1B12 |
| 22 | VH CDR1 a.a. 12A4 | 47 | VH CDR3 a.a. 7H1 |
| 23 | VH CDR1 a.a. 10A5 | 48 | VH CDR3 a.a. 11E6 |
| 24 | VH CDR1 a.a. 5F8 | 49 | VH CDR3 a.a. 12B7 |
| 25 | VH CDR1 a.a. 10H10 | 50 | VH CDR3 a.a. 13G4 |
| 51 | VK CDR1 a.a. 3G10 | 79 | VK CDR3 a.a. 12B7 |
| 52 | VK CDR1 a.a. 12A4 | 80 | VK CDR3 a.a. 13G4 |
| 53 | VK CDR1 a.a. 10A5 | | |
| 54 | VK CDR1 a.a. 5F8 | 81 | VH n.t. 3G10 |
| 55 | VK CDR1 a.a. 10H10 | 82 | VH n.t. 12A4 |
| 56 | VK CDR1 a.a. 1B12 | 83 | VH n.t. 10A5 |
| 57 | VK CDR1 a.a. 7H1 | 84 | VH n.t. 5F8 |
| 58 | VK CDR1 a.a. 11E6 | 85 | VH n.t. 10H10 |
| 59 | VK CDR1 a.a. 12B7 | 86 | VH n.t. 1B12 |
| 60 | VK CDR1 a.a. 13G4 | 87 | VH n.t. 7H1 |
| | | 88 | VH n.t. 11E6 |
| 61 | VK CDR2 a.a. 3G10 | 89 | VH n.t. 12B7 |
| 62 | VK CDR2 a.a. 12A4 | 90 | VH n.t. 13G4 |
| 63 | VK CDR2 a.a. 10A5 | | |
| 64 | VK CDR2 a.a. 5F8 | 91 | VK n.t. 3G10 |
| 65 | VK CDR2 a.a. 10H10 | 92 | VK n.t. 12A4 |
| 66 | VK CDR2 a.a. 1B12 | 93 | VK n.t. 10A5 |
| 67 | VK CDR2 a.a. 7H1 | 94 | VK n.t. 5F8 |
| 68 | VK CDR2 a.a. 11E6 | 95 | VK n.t. 10H10 |
| 69 | VK CDR2 a.a. 12B7 | 96 | VK n.t. 1B12 |
| 70 | VK CDR2 a.a. 13G4 | 97 | VK n.t. 7H1 |
| | | 98 | VK n.t. 11E6 |
| 71 | VK CDR3 a.a. 3G10 | 99 | VK n.t. 12B7 |
| 72 | VK CDR3 a.a. 12A4 | 100 | VK n.t. 13G4 |
| 73 | VK CDR3 a.a. 10A5 | | |
| 74 | VK CDR3 a.a. 5F8 | 101 | VH 1-18 germline a.a. |
| 75 | VK CDR3 a.a. 10H10 | 102 | VH 1-69 germline a.a. |
| 76 | VK CDR3 a.a. 1B12 | 103 | VH 1-3 germline a.a. |
| 77 | VK CDR3 a.a. 7H1 | 104 | VH 3-9 germline a.a. |
| 78 | VK CDR3 a.a.11E6 | | |

PD-L1 Antibody Summary

| SEQ ID NO: | SEQUENCE | SEQ ID NO: | SEQUENCE |
|---|---|---|---|
| 105 | VK L6 germline a.a. | 108 | VK L18 germline a.a. |
| 106 | VK L15 germline a.a. | 109 | VK a.a. 11E6a |
| 107 | VK A27 germline a.a. | | |

We claim:

1. A monoclonal anti-PD-L1 antibody, or an antigen-binding portion thereof, which cross-competes for binding to human PD-L1 with a reference antibody, wherein the reference antibody comprises:
   (a) a heavy chain variable region comprising amino acids having the sequence set forth in SEQ ID NO:1 and a light chain variable region comprising amino acids having the sequence set forth in SEQ ID NO:11;
   (b) a heavy chain variable region comprising amino acids having the sequence set forth in SEQ ID NO:2 and a light chain variable region comprising amino acids having the sequence set forth in SEQ ID NO:12;
   (c) a heavy chain variable region comprising amino acids having the sequence set forth in SEQ ID NO:3 and a light chain variable region comprising amino acids having the sequence set forth in SEQ ID NO:13;
   (d) a heavy chain variable region comprising amino acids having the sequence set forth in SEQ ID NO:4 and a light chain variable region comprising amino acids having the sequence set forth in SEQ ID NO:14;
   (e) a heavy chain variable region comprising amino acids having the sequence set forth in SEQ ID NO:5 and a light chain variable region comprising amino acids having the sequence set forth in SEQ ID NO:15;
   (f) a heavy chain variable region comprising amino acids having the sequence set forth in SEQ ID NO:6 and a light chain variable region comprising amino acids having the sequence set forth in SEQ ID NO:16;
   (g) a heavy chain variable region comprising amino acids having the sequence set forth in SEQ ID NO:7 and a light chain variable region comprising amino acids having the sequence set forth in SEQ ID NO:17;
   (h) a heavy chain variable region comprising amino acids having the sequence set forth in SEQ ID NO:8 and a light chain variable region comprising amino acids having the sequence set forth in SEQ ID NO:18;
   (i) a heavy chain variable region comprising amino acids having the sequence set forth in SEQ ID NO:9 and a light chain variable region comprising amino acids having the sequence set forth in SEQ ID NO:19; or
   (j) a heavy chain variable region comprising amino acids having the sequence set forth in SEQ ID NO:10 and a light chain variable region comprising amino acids having the sequence set forth in SEQ ID NO:20; and
   wherein the monoclonal anti-PD-L1 antibody or antigen-binding portion thereof comprises a heavy chain variable region (VH) and a light chain variable region (VL), wherein the VH comprises a framework region exhibiting at least 90% sequence identity to a framework region of the heavy chain variable region of the reference antibody and/or the VL comprises a framework region exhibiting at least 90% sequence identity to a framework region of the light chain variable region of the reference antibody.

2. The monoclonal anti-PD-L1 antibody or antigen-binding portion thereof of claim 1, wherein the framework region of the VH exhibits at least 95% sequence identity to the framework region of the heavy chain variable region of the reference antibody and/or the framework region of the VL exhibits at least 95% sequence identity to the framework region of the light chain variable region of the reference antibody.

3. The monoclonal anti-PD-L1 antibody or antigen-binding portion thereof of claim 1, wherein the VL exhibits at least 90% sequence identity to:
  (a) the light chain variable region comprising amino acids having the sequence set forth in SEQ ID NO:11;
  (b) the light chain variable region comprising amino acids having the sequence set forth in SEQ ID NO:12;
  (c) the light chain variable region comprising amino acids having the sequence set forth in SEQ ID NO:13;
  (d) the light chain variable region comprising amino acids having the sequence set forth in SEQ ID NO:14;
  (e) the light chain variable region comprising amino acids having the sequence set forth in SEQ ID NO:15;
  (f) the light chain variable region comprising amino acids having the sequence set forth in SEQ ID NO:16;
  (g) the light chain variable region comprising amino acids having the sequence set forth in SEQ ID NO:17;
  (h) the light chain variable region comprising amino acids having the sequence set forth in SEQ ID NO:18;
  (i) the light chain variable region comprising amino acids having the sequence set forth in SEQ ID NO:19; or
  (j) the light chain variable region comprising amino acids having the sequence set forth in SEQ ID NO:20.

4. The monoclonal anti-PD-L1 antibody or antigen-binding portion thereof of claim 1, wherein the VL comprises a FR1 selected from:
  (a) the FR1 of the light chain variable region having the amino acid sequence set forth in SEQ ID NO:11 or the FR1 of the light chain variable region having the amino acid sequence set forth in SEQ ID NO:11 with one amino acid substitution;
  (b) the FR1 of the light chain variable region having the amino acid sequence set forth in SEQ ID NO:12 or the FR1 of the light chain variable region having the amino acid sequence set forth in SEQ ID NO:12 with one amino acid substitution;
  (c) the FR1 of the light chain variable region having the amino acid sequence set forth in SEQ ID NO:13 or the FR1 of the light chain variable region having the amino acid sequence set forth in SEQ ID NO:13 with one amino acid substitution;
  (d) the FR1 of the light chain variable region having the amino acid sequence set forth in SEQ ID NO:14 or the FR1 of the light chain variable region having the amino acid sequence set forth in SEQ ID NO:14 with one amino acid substitution;
  (e) the FR1 of the light chain variable region having the amino acid sequence set forth in SEQ ID NO:15 or the FR1 of the light chain variable region having the amino acid sequence set forth in SEQ ID NO:15 with one amino acid substitution;
  (f) the FR1 of the light chain variable region having the amino acid sequence set forth in SEQ ID NO:16 or the FR1 of the light chain variable region having the amino acid sequence set forth in SEQ ID NO:16 with one amino acid substitution;
  (g) the FR1 of the light chain variable region having the amino acid sequence set forth in SEQ ID NO:17 or the FR1 of the light chain variable region having the amino acid sequence set forth in SEQ ID NO:17 with one amino acid substitution;
  (h) the FR1 of the light chain variable region having the amino acid sequence set forth in SEQ ID NO:18 or the FR1 of the light chain variable region having the amino acid sequence set forth in SEQ ID NO:18 with one amino acid substitution;
  (i) the FR1 of the light chain variable region having the amino acid sequence set forth in SEQ ID NO:19 or the FR1 of the light chain variable region having the amino acid sequence set forth in SEQ ID NO:19 with one amino acid substitution; and
  (j) the FR1 of the light chain variable region having the amino acid sequence set forth in SEQ ID NO:20 or the FR1 of the light chain variable region having the amino acid sequence set forth in SEQ ID NO:20 with one amino acid substitution.

5. The monoclonal anti-PD-L1 antibody or antigen-binding portion thereof of claim 1, wherein the VL comprises a FR2 selected from:
  (a) the FR2 of the light chain variable region having the amino acid sequence set forth in SEQ ID NO:11 or the FR2 of the light chain variable region having the amino acid sequence set forth in SEQ ID NO:11 with one amino acid substitution;
  (b) the FR2 of the light chain variable region having the amino acid sequence set forth in SEQ ID NO:12 or the FR2 of the light chain variable region having the amino acid sequence set forth in SEQ ID NO:12 with one amino acid substitution;
  (c) the FR2 of the light chain variable region having the amino acid sequence set forth in SEQ ID NO:13 or the FR2 of the light chain variable region having the amino acid sequence set forth in SEQ ID NO:13 with one amino acid substitution;
  (d) the FR2 of the light chain variable region having the amino acid sequence set forth in SEQ ID NO:14 or the FR2 of the light chain variable region having the amino acid sequence set forth in SEQ ID NO:14 with one amino acid substitution;
  (e) the FR2 of the light chain variable region having the amino acid sequence set forth in SEQ ID NO:15 or the FR2 of the light chain variable region having the amino acid sequence set forth in SEQ ID NO:15 with one amino acid substitution;
  (f) the FR2 of the light chain variable region having the amino acid sequence set forth in SEQ ID NO:16 or the FR2 of the light chain variable region having the amino acid sequence set forth in SEQ ID NO:16 with one amino acid substitution;
  (g) the FR2 of the light chain variable region having the amino acid sequence set forth in SEQ ID NO:17 or the FR2 of the light chain variable region having the amino acid sequence set forth in SEQ ID NO:17 with one amino acid substitution;
  (h) the FR2 of the light chain variable region having the amino acid sequence set forth in SEQ ID NO:18 or the FR2 of the light chain variable region having the amino acid sequence set forth in SEQ ID NO:18 with one amino acid substitution;
  (i) the FR2 of the light chain variable region having the amino acid sequence set forth in SEQ ID NO:19 or the FR2 of the light chain variable region having the amino acid sequence set forth in SEQ ID NO:19 with one amino acid substitution; and
  (j) the FR2 of the light chain variable region having the amino acid sequence set forth in SEQ ID NO:20 or the FR2 of the light chain variable region having the amino acid sequence set forth in SEQ ID NO:20 with one amino acid substitution.

6. The monoclonal anti-PD-L1 antibody or antigen-binding portion thereof of claim 1, wherein the VL comprises a FR3 selected from:
  (a) the FR3 of the light chain variable region having the amino acid sequence set forth in SEQ ID NO:11 or the FR3 of the light chain variable region having the amino acid sequence set forth in SEQ ID NO:11 with one amino acid substitution;

(b) the FR3 of the light chain variable region having the amino acid sequence set forth in SEQ ID NO:12 or the FR3 of the light chain variable region having the amino acid sequence set forth in SEQ ID NO:12 with one amino acid substitution;

(c) the FR3 of the light chain variable region having the amino acid sequence set forth in SEQ ID NO:13 or the FR3 of the light chain variable region having the amino acid sequence set forth in SEQ ID NO:13 with one amino acid substitution;

(d) the FR3 of the light chain variable region having the amino acid sequence set forth in SEQ ID NO:14 or the FR3 of the light chain variable region having the amino acid sequence set forth in SEQ ID NO:14 with one amino acid substitution;

(e) the FR3 of the light chain variable region having the amino acid sequence set forth in SEQ ID NO:15 or the FR3 of the light chain variable region having the amino acid sequence set forth in SEQ ID NO:15 with one amino acid substitution;

(f) the FR3 of the light chain variable region having the amino acid sequence set forth in SEQ ID NO:16 or the FR3 of the light chain variable region having the amino acid sequence set forth in SEQ ID NO:16 with one amino acid substitution;

(g) the FR3 of the light chain variable region having the amino acid sequence set forth in SEQ ID NO:17 or the FR3 of the light chain variable region having the amino acid sequence set forth in SEQ ID NO:17 with one amino acid substitution;

(h) the FR3 of the light chain variable region having the amino acid sequence set forth in SEQ ID NO:18 or the FR3 of the light chain variable region having the amino acid sequence set forth in SEQ ID NO:18 with one amino acid substitution;

(i) the FR3 of the light chain variable region having the amino acid sequence set forth in SEQ ID NO:19 or the FR3 of the light chain variable region having the amino acid sequence set forth in SEQ ID NO:19 with one amino acid substitution; and (j) the FR3 of the light chain variable region having the amino acid sequence set forth in SEQ ID NO:20 or the FR3 of the light chain variable region having the amino acid sequence set forth in SEQ ID NO:20 with one amino acid substitution.

7. The monoclonal anti-PD-L1 antibody or antigen-binding portion thereof of claim 1, wherein the VL comprises a FR4 selected from:

(a) the FR4 of the light chain variable region having the amino acid sequence set forth in SEQ ID NO:11 or the FR4 of the light chain variable region having the amino acid sequence set forth in SEQ ID NO:11 with one amino acid substitution;

(b) the FR4 of the light chain variable region having the amino acid sequence set forth in SEQ ID NO:12 or the FR4 of the light chain variable region having the amino acid sequence set forth in SEQ ID NO:12 with one amino acid substitution;

(c) the FR4 of the light chain variable region having the amino acid sequence set forth in SEQ ID NO:13 or the FR4 of the light chain variable region having the amino acid sequence set forth in SEQ ID NO:13 with one amino acid substitution;

(d) the FR4 of the light chain variable region having the amino acid sequence set forth in SEQ ID NO:14 or the FR4 of the light chain variable region having the amino acid sequence set forth in SEQ ID NO 14 with one amino acid substitution;

(e) the FR4 of the light chain variable region having the amino acid sequence set forth in SEQ ID NO:15 or the FR4 of the light chain variable region having the amino acid sequence set forth in SEQ ID NO:15 with one amino acid substitution;

(f) the FR4 of the light chain variable region having the amino acid sequence set forth in SEQ ID NO:16 or the FR4 of the light chain variable region having the amino acid sequence set forth in SEQ ID NO:16 with one amino acid substitution;

(g) the FR4 of the light chain variable region having the amino acid sequence set forth in SEQ ID NO:17 or the FR4 of the light chain variable region having the amino acid sequence set forth in SEQ ID NO:17 with one amino acid substitution;

(h) the FR4 of the light chain variable region having the amino acid sequence set forth in SEQ ID NO:18 or the FR4 of the light chain variable region having the amino acid sequence set forth in SEQ ID NO:18 with one amino acid substitution;

(i) the FR4 of the light chain variable region having the amino acid sequence set forth in SEQ ID NO:19 or the FR4 of the light chain variable region having the amino acid sequence set forth in SEQ ID NO:19 with one amino acid substitution; and (j) the FR4 of the light chain variable region having the amino acid sequence set forth in SEQ ID NO:20 or the FR4 of the light chain variable region having the amino acid sequence set forth in SEQ ID NO:20 with one amino acid substitution.

8. The monoclonal anti-PD-L1 antibody or antigen-binding portion thereof of claim 1, wherein the VH comprises a FR1 selected from:

(a) the FR1 of the heavy chain variable region having the amino acid sequence set forth in SEQ ID NO:1 or the FR1 of the heavy chain variable region having the amino acid sequence set forth in SEQ ID NO:1 with one amino acid substitution;

(b) the FR1 of the heavy chain variable region having the amino acid sequence set forth in SEQ ID NO:2 or the FR1 of the heavy chain variable region having the amino acid sequence set forth in SEQ ID NO:2 with one amino acid substitution;

(c) the FR1 of the heavy chain variable region having the amino acid sequence set forth in SEQ ID NO:3 or the FR1 of the heavy chain variable region having the amino acid sequence set forth in SEQ ID NO:3 with one amino acid substitution;

(d) the FR1 of the heavy chain variable region having the amino acid sequence set forth in SEQ ID NO:4 or the FR1 of the heavy chain variable region having the amino acid sequence set forth in SEQ ID NO:4 with one amino acid substitution;

(e) the FR1 of the heavy chain variable region having the amino acid sequence set forth in SEQ ID NO:5 or the FR1 of the heavy chain variable region having the amino acid sequence set forth in SEQ ID NO:5 with one amino acid substitution;

(f) the FR1 of the heavy chain variable region having the amino acid sequence set forth in SEQ ID NO:6 or the FR1 of the heavy chain variable region having the amino acid sequence set forth in SEQ ID NO:6 with one amino acid substitution;
(g) the FR1 of the heavy chain variable region having the amino acid sequence set forth in SEQ ID NO:7 or the FR1 of the heavy chain variable region having the amino acid sequence set forth in SEQ ID NO:7 with one amino acid substitution;
(h) the FR1 of the heavy chain variable region having the amino acid sequence set forth in SEQ ID NO:8 or the FR1 of the heavy chain variable region having the amino acid sequence set forth in SEQ ID NO:8 with one amino acid substitution;
(i) the FR1 of the heavy chain variable region having the amino acid sequence set forth in SEQ ID NO:9 or the FR1 of the heavy chain variable region having the amino acid sequence set forth in SEQ ID NO:9 with one amino acid substitution; and
(j) the FR1 of the heavy chain variable region having the amino acid sequence set forth in SEQ ID NO:10 or the FR1 of the heavy chain variable region having the amino acid sequence set forth in SEQ ID NO:10 with one amino acid substitution.

9. The monoclonal anti-PD-L1 antibody or antigen-binding portion thereof of claim 1, wherein the VH comprises a FR2 selected from:
(a) the FR2 of the heavy chain variable region having the amino acid sequence set forth in SEQ ID NO:1 or the FR2 of the heavy chain variable region having the amino acid sequence set forth in SEQ ID NO:1 with one amino acid substitution;
(b) the FR2 of the heavy chain variable region having the amino acid sequence set forth in SEQ ID NO:2 or the FR2 of the heavy chain variable region having the amino acid sequence set forth in SEQ ID NO:2 with one amino acid substitution;
(c) the FR2 of the heavy chain variable region having the amino acid sequence set forth in SEQ ID NO:3 or the FR2 of the heavy chain variable region having the amino acid sequence set forth in SEQ ID NO:3 with one amino acid substitution;
(d) the FR2 of the heavy chain variable region having the amino acid sequence set forth in SEQ ID NO:4 or the FR2 of the heavy chain variable region having the amino acid sequence set forth in SEQ ID NO:4 with one amino acid substitution;
(e) the FR2 of the heavy chain variable region having the amino acid sequence set forth in SEQ ID NO:5 or the FR2 of the heavy chain variable region having the amino acid sequence set forth in SEQ ID NO:5 with one amino acid substitution;
(f) the FR2 of the heavy chain variable region having the amino acid sequence set forth in SEQ ID NO:6 or the FR2 of the heavy chain variable region having the amino acid sequence set forth in SEQ ID NO:6 with one amino acid substitution;
(g) the FR2 of the heavy chain variable region having the amino acid sequence set forth in SEQ ID NO:7 or the FR2 of the heavy chain variable region having the amino acid sequence set forth in SEQ ID NO:7 with one amino acid substitution;
(h) the FR2 of the heavy chain variable region having the amino acid sequence set forth in SEQ ID NO:8 or the FR2 of the heavy chain variable region having the amino acid sequence set forth in SEQ ID NO:8 with one amino acid substitution;
(i) the FR2 of the heavy chain variable region having the amino acid sequence set forth in SEQ ID NO:9 or the FR2 of the heavy chain variable region having the amino acid sequence set forth in SEQ ID NO:9 with one amino acid substitution; and
(j) the FR2 of the heavy chain variable region having the amino acid sequence set forth in SEQ ID NO:10 or the FR2 of the heavy chain variable region having the amino acid sequence set forth in SEQ ID NO:10 with one amino acid substitution.

10. The monoclonal anti-PD-L1 antibody or antigen-binding portion thereof of claim 1, wherein the VH comprises a FR3 selected from:
(a) the FR3 of the heavy chain variable region having the amino acid sequence set forth in SEQ ID NO:1 or the FR3 of the heavy chain variable region having the amino acid sequence set forth in SEQ ID NO:1 with one amino acid substitution;
(b) the FR3 of the heavy chain variable region having the amino acid sequence set forth in SEQ ID NO:2 or the FR3 of the heavy chain variable region having the amino acid sequence set forth in SEQ ID NO:2 with one amino acid substitution;
(c) the FR3 of the heavy chain variable region having the amino acid sequence set forth in SEQ ID NO:3 or the FR3 of the heavy chain variable region having the amino acid sequence set forth in SEQ ID NO:3 with one amino acid substitution;
(d) the FR3 of the heavy chain variable region having the amino acid sequence set forth in SEQ ID NO:4 or the FR3 of the heavy chain variable region having the amino acid sequence set forth in SEQ ID NO:4 with one amino acid substitution;
(e) the FR3 of the heavy chain variable region having the amino acid sequence set forth in SEQ ID NO:5 or the FR3 of the heavy chain variable region having the amino acid sequence set forth in SEQ ID NO:5 with one amino acid substitution;
(f) the FR3 of the heavy chain variable region having the amino acid sequence set forth in SEQ ID NO:6 or the FR3 of the heavy chain variable region having the amino acid sequence set forth in SEQ ID NO:6 with one amino acid substitution;
(g) the FR3 of the heavy chain variable region having the amino acid sequence set forth in SEQ ID NO:7 or the FR3 of the heavy chain variable region having the amino acid sequence set forth in SEQ ID NO:7 with one amino acid substitution;
(h) the FR3 of the heavy chain variable region having the amino acid sequence set forth in SEQ ID NO:8 or the FR3 of the heavy chain variable region having the amino acid sequence set forth in SEQ ID NO:8 with one amino acid substitution;
(i) the FR3 of the heavy chain variable region having the amino acid sequence set forth in SEQ ID NO:9 or the FR3 of the heavy chain variable region having the amino acid sequence set forth in SEQ ID NO:9 with one amino acid substitution; and
(j) the FR3 of the heavy chain variable region having the amino acid sequence set forth in SEQ ID NO:10 or the FR3 of the heavy chain variable region having the amino acid sequence set forth in SEQ ID NO:10 with one amino acid substitution.

11. The monoclonal anti-PD-L1 antibody or antigen-binding portion thereof of claim 1, wherein the VH comprises a FR4 selected from:
(a) the FR4 of the heavy chain variable region having the amino acid sequence set forth in SEQ ID NO:1 or the FR4 of the heavy chain variable region having the amino acid sequence set forth in SEQ ID NO:1 with one amino acid substitution;

(b) the FR4 of the heavy chain variable region having the amino acid sequence set forth in SEQ ID NO:2 or the FR4 of the heavy chain variable region having the amino acid sequence set forth in SEQ ID NO:2 with one amino acid substitution;

(c) the FR4 of the heavy chain variable region having the amino acid sequence set forth in SEQ ID NO:3 or the FR4 of the heavy chain variable region having the amino acid sequence set forth in SEQ ID NO:3 with one amino acid substitution;

(d) the FR4 of the heavy chain variable region having the amino acid sequence set forth in SEQ ID NO:4 or the FR4 of the heavy chain variable region having the amino acid sequence set forth in SEQ ID NO:4 with one amino acid substitution;

(e) the FR4 of the heavy chain variable region having the amino acid sequence set forth in SEQ ID NO:5 or the FR4 of the heavy chain variable region having the amino acid sequence set forth in SEQ ID NO:5 with one amino acid substitution;

(f) the FR4 of the heavy chain variable region having the amino acid sequence set forth in SEQ ID NO:6 or the FR4 of the heavy chain variable region having the amino acid sequence set forth in SEQ ID NO:6 with one amino acid substitution;

(g) the FR4 of the heavy chain variable region having the amino acid sequence set forth in SEQ ID NO:7 or the FR4 of the heavy chain variable region having the amino acid sequence set forth in SEQ ID NO:7 with one amino acid substitution;

(h) the FR4 of the heavy chain variable region having the amino acid sequence set forth in SEQ ID NO:8 or the FR4 of the heavy chain variable region having the amino acid sequence set forth in SEQ ID NO:8 with one amino acid substitution;

(i) the FR4 of the heavy chain variable region having the amino acid sequence set forth in SEQ ID NO:9 or the FR4 of the heavy chain variable region having the amino acid sequence set forth in SEQ ID NO:9 with one amino acid substitution; and (j) the FR4 of the heavy chain variable region having the amino acid sequence set forth in SEQ ID NO:10 or the FR4 of the heavy chain variable region having the amino acid sequence set forth in SEQ ID NO:10 with one amino acid substitution.

12. The monoclonal anti-PD-L1 antibody or antigen-binding portion thereof of claim 1, wherein the VH is of a human IgG1, a human IgG2, a human IgG3, or a human IgG4 isotype.

13. The monoclonal anti-PD-L1 antibody or antigen-binding portion thereof of claim 12, wherein the VH is of a human IgG4 isotype.

14. The monoclonal anti-PD-L1 antibody or antigen-binding portion thereof of claim 12, wherein the VH is of a human IgG1 isotype and is modified by replacing at least one amino acid residue with a different amino acid residue to alter one or more effector functions of the monoclonal anti-PD-L1 antibody or antigen-binding portion thereof.

15. The monoclonal anti-PD-L1 antibody or antigen-binding portion thereof of claim 1, which binds to human PD-L1 with a KD of $5\times10^{-9}$ M or less.

16. The monoclonal anti-PD-L1 antibody or antigen-binding portion thereof of claim 1, which binds to human PD-L1 with a KD of $2\times10^{-9}$ M or less.

17. The monoclonal anti-PD-L1 antibody or antigen-binding portion thereof of claim 1, which binds to human PD-L1 with a KD of $1\times10^{-9}$ M or less.

18. The monoclonal anti-PD-L1 antibody or antigen-binding portion thereof of claim 1, wherein the reference antibody binds to human PD-L1 with a KD of about $5\times10^{-9}$ M.

19. The monoclonal anti-PD-L1 antibody or antigen-binding portion thereof of claim 1, wherein the reference antibody binds to human PD-L1 with a KD of $2\times10^{-9}$ M or less.

20. The monoclonal anti-PD-L1 antibody or antigen-binding portion thereof of claim 1, wherein the reference antibody binds to human PD-L1 with a KD of $1\times10^{-9}$ M or less.

21. The monoclonal anti-PD-L1 antibody or antigen-binding portion thereof of claim 1, which exhibits the following properties:
  (a) binds with high affinity to human PD-L1 with a KD of about $2\times10^{-9}$ M or less as determined by surface plasmon resonance analysis using a Biacore system;
  (b) inhibits binding of PD-L1 to a PD-1 receptor;
  (c) augments T cell proliferation, IFN-$\gamma$ and IL-2 secretion in mixed lymphocyte reaction assays;
  (d) stimulates antibody responses; and
  (e) reverses the suppressive effect of T regulatory cells on T cell effector cells, dendritic cells, or T cell effector cells and dendritic cells.

22. The monoclonal anti-PD-L1 antibody or antigen-binding portion thereof of claim 1, which is a human or a humanized antibody or a portion thereof.

23. The monoclonal anti-PD-L1 antibody or antigen-binding portion thereof of claim 1, comprising:
  (a) the VH which comprises amino acids having the sequence set forth in SEQ ID NO:1 or a conservative sequence modification thereof and the VL which comprises amino acids having the sequence set forth in SEQ ID NO:11 or a conservative sequence modification thereof;
  (b) the VH which comprises amino acids having the sequence set forth in SEQ ID NO:2 or a conservative sequence modification thereof and the VL which comprises amino acids having the sequence set forth in SEQ ID NO:12 or a conservative sequence modification thereof;
  (c) the VH which comprises amino acids having the sequence set forth in SEQ ID NO:6 or a conservative sequence modification thereof and the VL which comprises amino acids having the sequence set forth in SEQ ID NO:16 or a conservative sequence modification thereof;
  (d) the VH which comprises amino acids having the sequence set forth in SEQ ID NO:7 or a conservative sequence modification thereof and the VL which comprises amino acids having the sequence set forth in SEQ ID NO:17 or a conservative sequence modification thereof;
  (e) the VH which comprises amino acids having the sequence set forth in SEQ ID NO:8 or a conservative sequence modification thereof and the VL which comprises amino acids having the sequence set forth in SEQ ID NO:18 or a conservative sequence modification thereof;
  (f) the VH which comprises amino acids having the sequence set forth in SEQ ID NO:9 or a conservative sequence modification thereof and the VL which comprises amino acids having the sequence set forth in SEQ ID NO:19 or a conservative sequence modification thereof; or
(g) the VH which comprises amino acids having the sequence set forth in SEQ ID NO:10 or a conservative sequence modification thereof and the VL which comprises amino acids having the sequence set forth in SEQ ID NO:20 or a conservative sequence modification thereof,
wherein the conservative sequence modification comprises one or more additions, deletions, or conservative amino acid substitutions,
and wherein the antibodies comprising a conservative sequence modification retain the functional characteristics of unmodified antibodies.

24. The monoclonal anti-PD-L1 antibody or antigen-binding portion thereof of claim 1, comprising the VH which comprises amino acids having the sequence set forth in SEQ ID NO:2 or a conservative sequence modification thereof and the VL which comprises amino acids having the sequence set forth in SEQ ID NO:12 or a conservative sequence modification thereof, wherein the conservative sequence modification comprises one or more additions, deletions, or conservative amino acid substitutions.

25. The monoclonal anti-PD-L1 antibody or antigen-binding portion thereof of claim 23, wherein the conservative sequence modification comprises a modification of one or more residues within one or more CDR regions, within one or more framework regions, or within one or more CDR regions and one or more framework regions.

26. The monoclonal anti-PD-L1 antibody or antigen-binding portion thereof of claim 23, wherein no more than three amino acid residues within a CDR region are modified.

27. A composition comprising the monoclonal anti-PD-L1 antibody or antigen-binding portion thereof of claim 1, formulated together with a pharmaceutically acceptable carrier.

28. The composition of claim 27, wherein the pharmaceutically acceptable carrier is suitable for intravenous administration.

29. A kit comprising the composition of claim 27, a label indicating the intended use of the contents of the kit and instructions for use.

30. The kit of claim A, further comprising at least one additional anti-neoplastic agent.

* * * * *

SEQUENCE LISTING

<160> NUMBER OF SEQ ID NOS: 120

<210> SEQ ID NO 1
<211> LENGTH: 117
<212> TYPE: PRT
<213> ORGANISM: Homo sapiens

<400> SEQUENCE: 1

```
Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Asp Tyr
             20                  25                  30
Gly Phe Ser Trp Val Arg Gln Ala Pro Gly Gln Gly Leu Glu Trp Met
         35                  40                  45
Gly Trp Ile Thr Ala Tyr Asn Gly Asn Thr Asn Tyr Ala Gln Lys Leu
     50                  55                  60
Gln Gly Arg Val Thr Met Thr Thr Asp Thr Ser Thr Ser Thr Val Tyr
 65                  70                  75                  80
Met Glu Leu Arg Ser Leu Arg Ser Asp Asp Thr Ala Val Tyr Tyr Cys
                 85                  90                  95
Ala Arg Asp Tyr Phe Tyr Gly Met Asp Val Trp Gly Gln Gly Thr Thr
            100                 105                 110
Val Thr Val Ser Ser
        115
```

<210> SEQ ID NO 2
<211> LENGTH: 123
<212> TYPE: PRT
<213> ORGANISM: Homo sapiens

<400> SEQUENCE: 2

```
Gln Val Gln Leu Val Gln Ser Gly Ala Glu Val Lys Lys Pro Gly Ser
 1               5                  10                  15
Ser Val Lys Val Ser Cys Lys Thr Ser Gly Asp Thr Phe Ser Thr Tyr
             20                  25                  30
Ala Ile Ser Trp Val Arg Gln Ala Pro Gly Gln Gly Leu Glu Trp Met
         35                  40                  45
Gly Gly Ile Ile Pro Ile Phe Gly Lys Ala His Tyr Ala Gln Lys Phe
     50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Phe Cys
                 85                  90                  95
Ala Arg Lys Phe His Phe Val Ser Gly Ser Pro Phe Gly Met Asp Val
            100                 105                 110
Trp Gly Gln Gly Thr Thr Val Thr Val Ser Ser
        115                 120
```

<210> SEQ ID NO 3
<211> LENGTH: 118
<212> TYPE: PRT
<213> ORGANISM: Homo sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Val His Trp Val Arg Gln Ala Pro Gly Gln Arg Leu Glu Trp Met
        35                  40                  45

Gly Trp Leu His Ala Asp Thr Gly Ile Thr Lys Phe Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Gln Leu Trp Phe Asp Tyr Trp Gly Gln Gly Thr
            100                 105                 110

Leu Val Thr Val Ser Ser
        115

<210> SEQ ID NO 4
<211> LENGTH: 120
<212> TYPE: PRT
<213> ORGANISM: Homo sapiens

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Val Ser Gly Ile Phe Ser Thr Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Thr Ala Asn His Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Gly Ile Ala Ala Ala Leu Phe Asp Tyr Trp Gly Gln
            100                 105                 110

Gly Thr Leu Val Thr Val Ser Ser
        115                 120

<210> SEQ ID NO 5
<211> LENGTH: 113
<212> TYPE: PRT
<213> ORGANISM: Homo sapiens

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Val Ser Gly Phe Thr Phe Asp Asp Tyr
            20                  25                  30

Val Val His Trp Val Arg Gln Ala Pro Gly Lys Gly Leu Glu Trp Val

```
                35                  40                  45
Ser Gly Ile Ser Gly Asn Ser Gly Asn Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Val Pro Phe Asp Tyr Trp Gly Gln Gly Thr Leu Val Thr Val Ser
                100                 105                 110

Ser
```

<210> SEQ ID NO 6
<211> LENGTH: 123
<212> TYPE: PRT
<213> ORGANISM: Homo sapiens

<400> SEQUENCE: 6

```
Gln Val Gln Leu Val Gln Ser Gly Ala Glu Val Lys Lys Pro Gly Ser
 1                5                  10                  15

Ser Val Lys Val Ser Cys Lys Thr Ser Gly Asp Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Arg Ala His Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Lys Phe His Phe Val Ser Gly Ser Pro Phe Gly Met Asp Val
                100                 105                 110

Trp Gly Gln Gly Thr Thr Val Thr Val Ser Ser
            115                 120
```

<210> SEQ ID NO 7
<211> LENGTH: 123
<212> TYPE: PRT
<213> ORGANISM: Homo sapiens

<400> SEQUENCE: 7

```
Gln Val Gln Leu Val Gln Ser Gly Ala Glu Val Lys Lys Pro Gly Ser
 1                5                  10                  15

Ser Val Lys Val Ser Cys Lys Thr Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Lys Ala His Tyr Ala Gln Lys Phe
 50                  55                  60

Gln Gly Arg Val Thr Ile Thr Ala Asp Glu Ser Thr Thr Thr Ala Tyr
 65                  70                  75                  80

Met Glu Leu Ser Ser Leu Arg Ser Glu Asp Thr Ala Val Tyr Tyr Cys
                 85                  90                  95

Ala Arg Lys Tyr Asp Tyr Val Ser Gly Ser Pro Phe Gly Met Asp Val
                100                 105                 110

Trp Gly Gln Gly Thr Thr Val Thr Val Ser Ser
            115                 120
```

<210> SEQ ID NO 8
<211> LENGTH: 121
<212> TYPE: PRT
<213> ORGANISM: Homo sapiens

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Gly Gly Thr Phe Ser Ser Tyr
                20                  25                  30

Ala Ile Asn Trp Val Arg Gln Ala Pro Gly Gln Gly Leu Glu Trp Met
            35                  40                  45

Gly Gly Ile Ile Pro Ile Phe Gly Ser Ala Asn Tyr Ala Gln Lys Phe
        50                  55                  60

Gln Asp Arg Val Thr Ile Thr Ala Asp Glu Ser Thr Ser Ala Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Gly Trp Ser Arg Tyr Tyr Met Asp Val Trp Gly
            100                 105                 110

Gln Gly Thr Thr Val Thr Val Ser Ser
        115                 120

<210> SEQ ID NO 9
<211> LENGTH: 123
<212> TYPE: PRT
<213> ORGANISM: Homo sapiens

<400> SEQUENCE: 9

Gln Val Gln Leu Val Gln Ser Gly Ala Glu Val Lys Glu Pro Gly Ser
1               5                   10                  15

Ser Val Lys Val Ser Cys Lys Ala Ser Gly Gly Thr Phe Asn Ser Tyr
                20                  25                  30

Ala Ile Ser Trp Val Arg Gln Ala Pro Gly Gln Gly Leu Glu Trp Met
            35                  40                  45

Gly Gly Ile Ile Pro Leu Phe Gly Ile Ala His Tyr Ala Gln Lys Phe
        50                  55                  60

Gln Gly Arg Val Thr Ile Thr Ala Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Lys Tyr Ser Tyr Val Ser Gly Ser Pro Phe Gly Met Asp Val
            100                 105                 110

Trp Gly Gln Gly Thr Thr Val Thr Val Ser Ser
        115                 120

<210> SEQ ID NO 10
<211> LENGTH: 121
<212> TYPE: PRT
<213> ORGANISM: Homo sapiens

<400> SEQUENCE: 10

Glu Val Gln Leu Val Glu Ser Gly Gly Gly Leu Val Gln Pro Gly Arg
1               5                   10                  15

Ser Leu Arg Leu Ser Cys Ala Ala Ser Gly Ile Thr Phe Asp Asp Tyr
                20                  25                  30

Gly Met His Trp Val Arg Gln Ala Pro Gly Lys Gly Leu Glu Trp Val
         35                  40                  45

Ser Gly Ile Ser Trp Asn Arg Gly Arg Ile Glu Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Gly Arg Phe Arg Tyr Phe Asp Trp Phe Leu Asp Tyr Trp Gly
                100                 105                 110

Gln Gly Thr Leu Val Thr Val Ser Ser
                115                 120

<210> SEQ ID NO 11
<211> LENGTH: 107
<212> TYPE: PRT
<213> ORGANISM: Homo sapiens

<400> SEQUENCE: 11

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Val Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Arg
                 85                  90                  95

Thr Phe Gly Gln Gly Thr Lys Val Glu Ile Lys
            100                 105

<210> SEQ ID NO 12
<211> LENGTH: 106
<212> TYPE: PRT
<213> ORGANISM: Homo sapiens

<400> SEQUENCE: 12

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Lys Val Glu Ile Lys
            100                 105

<210> SEQ ID NO 13
<211> LENGTH: 107

<212> TYPE: PRT
<213> ORGANISM: Homo sapiens

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105
```

<210> SEQ ID NO 14
<211> LENGTH: 108
<212> TYPE: PRT
<213> ORGANISM: Homo sapiens

<400> SEQUENCE: 14

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 15
<211> LENGTH: 107
<212> TYPE: PRT
<213> ORGANISM: Homo sapiens

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
```

```
                    85                  90                  95

Thr Phe Gly Gln Gly Thr Lys Leu Glu Ile Lys
                100                 105

<210> SEQ ID NO 16
<211> LENGTH: 106
<212> TYPE: PRT
<213> ORGANISM: Homo sapiens

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
                100                 105

<210> SEQ ID NO 17
<211> LENGTH: 106
<212> TYPE: PRT
<213> ORGANISM: Homo sapiens

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
                100                 105

<210> SEQ ID NO 18
<211> LENGTH: 106
<212> TYPE: PRT
<213> ORGANISM: Homo sapiens

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45
```

```
Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Phe Gly Gly Gly Thr Lys Val Glu Ile Lys
            100                 105
```

<210> SEQ ID NO 19
<211> LENGTH: 106
<212> TYPE: PRT
<213> ORGANISM: Homo sapiens

<400> SEQUENCE: 19

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Arg Leu Glu Ile Lys
            100                 105
```

<210> SEQ ID NO 20
<211> LENGTH: 107
<212> TYPE: PRT
<213> ORGANISM: Homo sapiens

<400> SEQUENCE: 20

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                 20                  25                  30

Leu Ala Trp Tyr Gln Gln Lys Pro Gly Lys Ala Pro Lys Leu Leu Ile
             35                  40                  45

Tyr Asp Ala Ser Ser Leu Glu Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Phe
                 85                  90                  95

Thr Phe Gly Pro Gly Thr Lys Val Asp Ile Lys
            100                 105
```

<210> SEQ ID NO 21
<211> LENGTH: 5
<212> TYPE: PRT
<213> ORGANISM: Homo sapiens

<400> SEQUENCE: 21

Asp Tyr Gly Phe Ser
1               5

<210> SEQ ID NO 22
<211> LENGTH: 5
<212> TYPE: PRT
<213> ORGANISM: Homo sapiens

<400> SEQUENCE: 22

Thr Tyr Ala Ile Ser
1               5

<210> SEQ ID NO 23
<211> LENGTH: 5
<212> TYPE: PRT
<213> ORGANISM: Homo sapiens

<400> SEQUENCE: 23

Ser Tyr Asp Val His
1               5

<210> SEQ ID NO 24
<211> LENGTH: 5
<212> TYPE: PRT
<213> ORGANISM: Homo sapiens

<400> SEQUENCE: 24

Thr Tyr Ala Ile Asn
1               5

<210> SEQ ID NO 25
<211> LENGTH: 5
<212> TYPE: PRT
<213> ORGANISM: Homo sapiens

<400> SEQUENCE: 25

Asp Tyr Val Val His
1               5

<210> SEQ ID NO 26
<211> LENGTH: 5
<212> TYPE: PRT
<213> ORGANISM: Homo sapiens

<400> SEQUENCE: 26

Ser Tyr Ala Ile Ser
1               5

<210> SEQ ID NO 27
<211> LENGTH: 5
<212> TYPE: PRT
<213> ORGANISM: Homo sapiens

<400> SEQUENCE: 27

Ser Tyr Ala Ile Ser
1               5

<210> SEQ ID NO 28
<211> LENGTH: 5
<212> TYPE: PRT
<213> ORGANISM: Homo sapiens

<400> SEQUENCE: 28

Ser Tyr Ala Ile Asn
1               5

```
<210> SEQ ID NO 29
<211> LENGTH: 5
<212> TYPE: PRT
<213> ORGANISM: Homo sapiens

<400> SEQUENCE: 29

Ser Tyr Ala Ile Ser
1               5

<210> SEQ ID NO 30
<211> LENGTH: 5
<212> TYPE: PRT
<213> ORGANISM: Homo sapiens

<400> SEQUENCE: 30

Asp Tyr Gly Met His
1               5

<210> SEQ ID NO 31
<211> LENGTH: 17
<212> TYPE: PRT
<213> ORGANISM: Homo sapiens

<400> SEQUENCE: 31

Trp Ile Thr Ala Tyr Asn Gly Asn Thr Asn Tyr Ala Gln Lys Leu Gln
1               5                   10                  15

Gly

<210> SEQ ID NO 32
<211> LENGTH: 17
<212> TYPE: PRT
<213> ORGANISM: Homo sapiens

<400> SEQUENCE: 32

Gly Ile Ile Pro Ile Phe Gly Lys Ala His Tyr Ala Gln Lys Phe Gln
1               5                   10                  15

Gly

<210> SEQ ID NO 33
<211> LENGTH: 17
<212> TYPE: PRT
<213> ORGANISM: Homo sapiens

<400> SEQUENCE: 33

Trp Leu His Ala Asp Thr Gly Ile Thr Lys Phe Ser Gln Lys Phe Gln
1               5                   10                  15

Gly

<210> SEQ ID NO 34
<211> LENGTH: 17
<212> TYPE: PRT
<213> ORGANISM: Homo sapiens

<400> SEQUENCE: 34

Gly Ile Ile Pro Ile Phe Gly Thr Ala Asn His Ala Gln Lys Phe Gln
1               5                   10                  15

Gly

<210> SEQ ID NO 35
<211> LENGTH: 17
<212> TYPE: PRT
```

<213> ORGANISM: Homo sapiens

<400> SEQUENCE: 35

Gly Ile Ser Gly Asn Ser Gly Asn Ile Gly Tyr Ala Asp Ser Val Lys
1               5                   10                  15

Gly

<210> SEQ ID NO 36
<211> LENGTH: 17
<212> TYPE: PRT
<213> ORGANISM: Homo sapiens

<400> SEQUENCE: 36

Gly Ile Ile Pro Ile Phe Gly Arg Ala His Tyr Ala Gln Lys Phe Gln
1               5                   10                  15

Gly

<210> SEQ ID NO 37
<211> LENGTH: 17
<212> TYPE: PRT
<213> ORGANISM: Homo sapiens

<400> SEQUENCE: 37

Gly Ile Ile Pro Ile Phe Gly Lys Ala His Tyr Ala Gln Lys Phe Gln
1               5                   10                  15

Gly

<210> SEQ ID NO 38
<211> LENGTH: 17
<212> TYPE: PRT
<213> ORGANISM: Homo sapiens

<400> SEQUENCE: 38

Gly Ile Ile Pro Ile Phe Gly Ser Ala Asn Tyr Ala Gln Lys Phe Gln
1               5                   10                  15

Asp

<210> SEQ ID NO 39
<211> LENGTH: 17
<212> TYPE: PRT
<213> ORGANISM: Homo sapiens

<400> SEQUENCE: 39

Gly Ile Ile Pro Leu Phe Gly Ile Ala His Tyr Ala Gln Lys Phe Gln
1               5                   10                  15

Gly

<210> SEQ ID NO 40
<211> LENGTH: 17
<212> TYPE: PRT
<213> ORGANISM: Homo sapiens

<400> SEQUENCE: 40

Gly Ile Ser Trp Asn Arg Gly Arg Ile Glu Tyr Ala Asp Ser Val Lys
1               5                   10                  15

Gly

<210> SEQ ID NO 41
<211> LENGTH: 8
<212> TYPE: PRT
<213> ORGANISM: Homo sapiens

<400> SEQUENCE: 41

Asp Tyr Phe Tyr Gly Met Asp Val
1               5

<210> SEQ ID NO 42
<211> LENGTH: 14
<212> TYPE: PRT
<213> ORGANISM: Homo sapiens

<400> SEQUENCE: 42

Lys Phe His Phe Val Ser Gly Ser Pro Phe Gly Met Asp Val
1               5                   10

<210> SEQ ID NO 43
<211> LENGTH: 9
<212> TYPE: PRT
<213> ORGANISM: Homo sapiens

<400> SEQUENCE: 43

Glu Arg Ile Gln Leu Trp Phe Asp Tyr
1               5

<210> SEQ ID NO 44
<211> LENGTH: 11
<212> TYPE: PRT
<213> ORGANISM: Homo sapiens

<400> SEQUENCE: 44

Asp Gln Gly Ile Ala Ala Ala Leu Phe Asp Tyr
1               5                   10

<210> SEQ ID NO 45
<211> LENGTH: 4
<212> TYPE: PRT
<213> ORGANISM: Homo sapiens

<400> SEQUENCE: 45

Pro Phe Asp Tyr
1

<210> SEQ ID NO 46
<211> LENGTH: 14
<212> TYPE: PRT
<213> ORGANISM: Homo sapiens

<400> SEQUENCE: 46

Lys Phe His Phe Val Ser Gly Ser Pro Phe Gly Met Asp Val
1               5                   10

<210> SEQ ID NO 47
<211> LENGTH: 14
<212> TYPE: PRT
<213> ORGANISM: Homo sapiens

<400> SEQUENCE: 47

Lys Tyr Asp Tyr Val Ser Gly Ser Pro Phe Gly Met Asp Val
1               5                   10

<210> SEQ ID NO 48
<211> LENGTH: 12
<212> TYPE: PRT
<213> ORGANISM: Homo sapiens

<400> SEQUENCE: 48

```
Asp Ser Ser Gly Trp Ser Arg Tyr Tyr Met Asp Val
1               5                   10
```

<210> SEQ ID NO 49
<211> LENGTH: 14
<212> TYPE: PRT
<213> ORGANISM: Homo sapiens

<400> SEQUENCE: 49

```
Lys Tyr Ser Tyr Val Ser Gly Ser Pro Phe Gly Met Asp Val
1               5                   10
```

<210> SEQ ID NO 50
<211> LENGTH: 12
<212> TYPE: PRT
<213> ORGANISM: Homo sapiens

<400> SEQUENCE: 50

```
Gly Arg Phe Arg Tyr Phe Asp Trp Phe Leu Asp Tyr
1               5                   10
```

<210> SEQ ID NO 51
<211> LENGTH: 11
<212> TYPE: PRT
<213> ORGANISM: Homo sapiens

<400> SEQUENCE: 51

```
Arg Ala Ser Gln Ser Val Ser Ser Tyr Leu Val
1               5                   10
```

<210> SEQ ID NO 52
<211> LENGTH: 11
<212> TYPE: PRT
<213> ORGANISM: Homo sapiens

<400> SEQUENCE: 52

```
Arg Ala Ser Gln Ser Val Ser Ser Tyr Leu Ala
1               5                   10
```

<210> SEQ ID NO 53
<211> LENGTH: 11
<212> TYPE: PRT
<213> ORGANISM: Homo sapiens

<400> SEQUENCE: 53

```
Arg Ala Ser Gln Gly Ile Ser Ser Trp Leu Ala
1               5                   10
```

<210> SEQ ID NO 54
<211> LENGTH: 12
<212> TYPE: PRT
<213> ORGANISM: Homo sapiens

<400> SEQUENCE: 54

```
Arg Ala Ser Gln Ser Val Ser Ser Ser Tyr Leu Ala
1               5                   10
```

<210> SEQ ID NO 55
<211> LENGTH: 11
<212> TYPE: PRT
<213> ORGANISM: Homo sapiens

<400> SEQUENCE: 55

```
Arg Ala Ser Gln Gly Ile Ser Ser Trp Leu Ala
```

1               5                   10

<210> SEQ ID NO 56
<211> LENGTH: 11
<212> TYPE: PRT
<213> ORGANISM: Homo sapiens

<400> SEQUENCE: 56

Arg Ala Ser Gln Ser Val Ser Ser Tyr Leu Ala
1               5                   10

<210> SEQ ID NO 57
<211> LENGTH: 11
<212> TYPE: PRT
<213> ORGANISM: Homo sapiens

<400> SEQUENCE: 57

Arg Ala Ser Gln Ser Val Ser Ser Tyr Leu Ala
1               5                   10

<210> SEQ ID NO 58
<211> LENGTH: 12
<212> TYPE: PRT
<213> ORGANISM: Homo sapiens

<400> SEQUENCE: 58

Arg Ala Ser Gln Ser Val Ser Ser Ser Tyr Leu Ala
1               5                   10

<210> SEQ ID NO 59
<211> LENGTH: 11
<212> TYPE: PRT
<213> ORGANISM: Homo sapiens

<400> SEQUENCE: 59

Arg Ala Ser Gln Ser Val Ser Ser Tyr Leu Ala
1               5                   10

<210> SEQ ID NO 60
<211> LENGTH: 11
<212> TYPE: PRT
<213> ORGANISM: Homo sapiens

<400> SEQUENCE: 60

Arg Ala Ser Gln Gly Ile Ser Ser Ala Leu Ala
1               5                   10

<210> SEQ ID NO 61
<211> LENGTH: 7
<212> TYPE: PRT
<213> ORGANISM: Homo sapiens

<400> SEQUENCE: 61

Asp Ala Ser Asn Arg Ala Thr
1               5

<210> SEQ ID NO 62
<211> LENGTH: 7
<212> TYPE: PRT
<213> ORGANISM: Homo sapiens

<400> SEQUENCE: 62

Asp Ala Ser Asn Arg Ala Thr
1               5

<210> SEQ ID NO 63
<211> LENGTH: 7
<212> TYPE: PRT
<213> ORGANISM: Homo sapiens

<400> SEQUENCE: 63

Ala Ala Ser Ser Leu Gln Ser
1               5

<210> SEQ ID NO 64
<211> LENGTH: 7
<212> TYPE: PRT
<213> ORGANISM: Homo sapiens

<400> SEQUENCE: 64

Gly Ala Ser Ser Arg Ala Thr
1               5

<210> SEQ ID NO 65
<211> LENGTH: 7
<212> TYPE: PRT
<213> ORGANISM: Homo sapiens

<400> SEQUENCE: 65

Ala Ala Ser Ser Leu Gln Ser
1               5

<210> SEQ ID NO 66
<211> LENGTH: 7
<212> TYPE: PRT
<213> ORGANISM: Homo sapiens

<400> SEQUENCE: 66

Asp Ala Ser Asn Arg Ala Thr
1               5

<210> SEQ ID NO 67
<211> LENGTH: 7
<212> TYPE: PRT
<213> ORGANISM: Homo sapiens

<400> SEQUENCE: 67

Asp Ala Ser Asn Arg Ala Thr
1               5

<210> SEQ ID NO 68
<211> LENGTH: 7
<212> TYPE: PRT
<213> ORGANISM: Homo sapiens

<400> SEQUENCE: 68

Gly Ala Ser Ser Arg Ala Thr
1               5

<210> SEQ ID NO 69
<211> LENGTH: 7
<212> TYPE: PRT
<213> ORGANISM: Homo sapiens

<400> SEQUENCE: 69

Asp Ala Ser Asn Arg Ala Thr
1               5

<210> SEQ ID NO 70

```
<211> LENGTH: 7
<212> TYPE: PRT
<213> ORGANISM: Homo sapiens

<400> SEQUENCE: 70

Asp Ala Ser Ser Leu Glu Ser
1               5

<210> SEQ ID NO 71
<211> LENGTH: 9
<212> TYPE: PRT
<213> ORGANISM: Homo sapiens

<400> SEQUENCE: 71

Gln Gln Arg Ser Asn Trp Pro Arg Thr
1               5

<210> SEQ ID NO 72
<211> LENGTH: 8
<212> TYPE: PRT
<213> ORGANISM: Homo sapiens

<400> SEQUENCE: 72

Gln Gln Arg Ser Asn Trp Pro Thr
1               5

<210> SEQ ID NO 73
<211> LENGTH: 9
<212> TYPE: PRT
<213> ORGANISM: Homo sapiens

<400> SEQUENCE: 73

Gln Gln Tyr Asn Ser Tyr Pro Tyr Thr
1               5

<210> SEQ ID NO 74
<211> LENGTH: 9
<212> TYPE: PRT
<213> ORGANISM: Homo sapiens

<400> SEQUENCE: 74

Gln Gln Tyr Gly Ser Ser Pro Trp Thr
1               5

<210> SEQ ID NO 75
<211> LENGTH: 9
<212> TYPE: PRT
<213> ORGANISM: Homo sapiens

<400> SEQUENCE: 75

Gln Gln Tyr Asn Ser Tyr Pro Tyr Thr
1               5

<210> SEQ ID NO 76
<211> LENGTH: 8
<212> TYPE: PRT
<213> ORGANISM: Homo sapiens

<400> SEQUENCE: 76

Gln Gln Arg Ser Asn Trp Pro Thr
1               5

<210> SEQ ID NO 77
<211> LENGTH: 8
<212> TYPE: PRT
```

<213> ORGANISM: Homo sapiens

<400> SEQUENCE: 77

Gln Gln Arg Ser Asn Trp Pro Thr
1               5

<210> SEQ ID NO 78
<211> LENGTH: 7
<212> TYPE: PRT
<213> ORGANISM: Homo sapiens

<400> SEQUENCE: 78

Gln Gln Tyr Gly Ser Ser Pro
1               5

<210> SEQ ID NO 79
<211> LENGTH: 8
<212> TYPE: PRT
<213> ORGANISM: Homo sapiens

<400> SEQUENCE: 79

Gln Gln Arg Ser Asn Trp Pro Thr
1               5

<210> SEQ ID NO 80
<211> LENGTH: 9
<212> TYPE: PRT
<213> ORGANISM: Homo sapiens

<400> SEQUENCE: 80

Gln Gln Phe Asn Ser Tyr Pro Phe Thr
1               5

<210> SEQ ID NO 81
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 81

```
cag gtt cag ctg gtg cag tct gga gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc gac tat      96
Ser Val Lys Val Ser Cys Lys Ala Ser Gly Tyr Thr Phe Thr Asp Tyr
            20                  25                  30 ggt ttc agc tgg gtg cga cag gcc cct gga caa ggg ctt gag tgg atg     144
Gly Phe Ser Trp Val Arg Gln Ala Pro Gly Gln Gly Leu Glu Trp Met
        35                  40                  45 gga tgg atc acc gct tac aat ggt aac aca aac tat gca cag aag ctc     192
Gly Trp Ile Thr Ala Tyr Asn Gly Asn Thr Asn Tyr Ala Gln Lys Leu
    50                  55                  60 cag ggc aga gtc acc atg acc aca gac aca tcc acg agc aca gtc tac     240
Gln Gly Arg Val Thr Met Thr Thr Asp Thr Ser Thr Ser Thr Val Tyr
65                  70                  75                  80 atg gag ctg agg agc ctg aga tct gac gac acg gcc gtg tat tac tgt     288
Met Glu Leu Arg Ser Leu Arg Ser Asp Asp Thr Ala Val Tyr Tyr Cys
                85                  90                  95 gcg aga gac tac ttc tac ggt atg gac gtc tgg ggc caa ggg acc acg     336
Ala Arg Asp Tyr Phe Tyr Gly Met Asp Val Trp Gly Gln Gly Thr Thr
            100                 105                 110
```

```
gtc acc gtc tcc tca                                                    351
Val Thr Val Ser Ser
        115
```

<210> SEQ ID NO 82
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 82

```
cag gtc cag ctg gtg cag tct ggg gct gag gtg aag aag cct ggg tcc        48
Gln Val Gln Leu Val Gln Ser Gly Ala Glu Val Lys Lys Pro Gly Ser
1               5                   10                  15 tcg gtg aag gtc tcc tgc aag act tct gga gac acc ttc agc acc tat        96
Ser Val Lys Val Ser Cys Lys Thr Ser Gly Asp Thr Phe Ser Thr Tyr
            20                  25                  30 gct atc agc tgg gtg cga cag gcc cct gga caa ggg ctt gag tgg atg       144
Ala Ile Ser Trp Val Arg Gln Ala Pro Gly Gln Gly Leu Glu Trp Met
        35                  40                  45 gga ggg atc atc cct ata ttt ggt aaa gca cac tac gca cag aag ttc       192
Gly Gly Ile Ile Pro Ile Phe Gly Lys Ala His Tyr Ala Gln Lys Phe
    50                  55                  60 cag ggc aga gtc acg att acc gcg gac gaa tcc acg agc aca gcc tac       240
Gln Gly Arg Val Thr Ile Thr Ala Asp Glu Ser Thr Ser Thr Ala Tyr
65                  70                  75                  80 atg gag ctg agc agc ctg aga tct gag gac acg gcc gtg tat ttt tgt       288
Met Glu Leu Ser Ser Leu Arg Ser Glu Asp Thr Ala Val Tyr Phe Cys
                85                  90                  95 gcg aga aag ttt cac ttt gtt tcg ggg agc ccc ttc ggt atg gac gtc       336
Ala Arg Lys Phe His Phe Val Ser Gly Ser Pro Phe Gly Met Asp Val
            100                 105                 110 tgg ggc caa ggg acc acg gtc acc gtc tcc tca                           369
Trp Gly Gln Gly Thr Thr Val Thr Val Ser Ser
        115                 120
```

<210> SEQ ID NO 83
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 83

```
cag gtc caa ctt gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtt tcc tgc aag gct tct gga tac acc ttc act agc tat        96
Ser Val Lys Val Ser Cys Lys Ala Ser Gly Tyr Thr Phe Thr Ser Tyr
            20                  25                  30 gat gta cat tgg gtg cgc cag gcc ccc gga caa agg ctt gag tgg atg       144
Asp Val His Trp Val Arg Gln Ala Pro Gly Gln Arg Leu Glu Trp Met
        35                  40                  45 gga tgg ctc cac gct gac act ggt atc aca aaa ttt tca cag aag ttc       192
Gly Trp Leu His Ala Asp Thr Gly Ile Thr Lys Phe Ser Gln Lys Phe
    50                  55                  60 cag ggc aga gtc acc att acc agg gac aca tcc gcg agc aca gcc tac       240
Gln Gly Arg Val Thr Ile Thr Arg Asp Thr Ser Ala Ser Thr Ala Tyr
65                  70                  75                  80 atg gag ctg agc agc ctg aga tct gaa gac acg gct gtg tat tac tgt       288
Met Glu Leu Ser Ser Leu Arg Ser Glu Asp Thr Ala Val Tyr Tyr Cys
```

```
Met Glu Leu Ser Ser Leu Arg Ser Glu Asp Thr Ala Val Tyr Tyr Cys
                85                  90                  95 gcg agg gag agg ata cag cta tgg ttt gac tac tgg ggc cag gga acc      336
Ala Arg Glu Arg Ile Gln Leu Trp Phe Asp Tyr Trp Gly Gln Gly Thr
            100                 105                 110 ctg gtc acc gtc tcc tca                                              354
Leu Val Thr Val Ser Ser
        115

<210> SEQ ID NO 84
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 84 cag gtc cag ctg gtg cag tct ggg gct gag gtg aag aag cct ggg tcc      48
Gln Val Gln Leu Val Gln Ser Gly Ala Glu Val Lys Lys Pro Gly Ser
1               5                   10                  15 tcg gtg aag gtc tcc tgc aag gtt tct gga ggc atc ttc agc acc tat      96
Ser Val Lys Val Ser Cys Lys Val Ser Gly Gly Ile Phe Ser Thr Tyr
            20                  25                  30 gct atc aac tgg gtg cga cag gcc cct gga caa ggg ctt gag tgg atg      144
Ala Ile Asn Trp Val Arg Gln Ala Pro Gly Gln Gly Leu Glu Trp Met
        35                  40                  45 gga ggg atc atc cct atc ttt ggt aca gca aac cac gca cag aag ttc      192
Gly Gly Ile Ile Pro Ile Phe Gly Thr Ala Asn His Ala Gln Lys Phe
    50                  55                  60 cag ggc aga gtc acg att acc gcg gac gaa tcc acg agc aca gcc tac      240
Gln Gly Arg Val Thr Ile Thr Ala Asp Glu Ser Thr Ser Thr Ala Tyr
65                  70                  75                  80 atg gag ctg agc agc ctg aga tct gag gac acg gcc gtg tat tac tgt      288
Met Glu Leu Ser Ser Leu Arg Ser Glu Asp Thr Ala Val Tyr Tyr Cys
                85                  90                  95 gcg aga gat cag ggt ata gca gca gcc ctt ttt gac tac tgg ggc cag      336
Ala Arg Asp Gln Gly Ile Ala Ala Ala Leu Phe Asp Tyr Trp Gly Gln
            100                 105                 110 gga acc ctg gtc acc gtc tcc tca                                      360
Gly Thr Leu Val Thr Val Ser Ser
        115                 120

<210> SEQ ID NO 85
<211> LENGTH: 339
<212> TYPE: DNA
<213> ORGANISM: Homo sapiens
<220> FEATURE:
<221> NAME/KEY: CDS
<222> LOCATION: (1)..(339)

<400> SEQUENCE: 85 gaa gtg cag ctg gtg gag tct ggg gga ggc ttg gta cag cct ggc agg      48
Glu Val Gln Leu Val Glu Ser Gly Gly Gly Leu Val Gln Pro Gly Arg
1               5                   10                  15 tcc ctg aga ctc tcc tgt gca gtc tct gga ttc acc ttt gat gat tat      96
Ser Leu Arg Leu Ser Cys Ala Val Ser Gly Phe Thr Phe Asp Asp Tyr
            20                  25                  30 gtc gtg cac tgg gtc cgg caa gct cca ggg aag ggc ctg gag tgg gtc      144
Val Val His Trp Val Arg Gln Ala Pro Gly Lys Gly Leu Glu Trp Val
        35                  40                  45 tca ggt att agt ggg aat agt ggt aac ata ggc tat gcg gac tct gtg      192
Ser Gly Ile Ser Gly Asn Ser Gly Asn Ile Gly Tyr Ala Asp Ser Val
```

```
                    50                  55                  60
aag ggc cga ttc acc atc tcc aga gac aac gcc aag aac tcc ctg tat          240
Lys Gly Arg Phe Thr Ile Ser Arg Asp Asn Ala Lys Asn Ser Leu Tyr
 65                  70                  75                  80 ctg caa atg aac agt ctg aga gct gag gac acg gcc ttg tat tac tgt          288
Leu Gln Met Asn Ser Leu Arg Ala Glu Asp Thr Ala Leu Tyr Tyr Cys
                     85                  90                  95 gcg gtc ccc ttt gac tac tgg ggc cag gga acc ctg gtc acc gtc tcc          336
Ala Val Pro Phe Asp Tyr Trp Gly Gln Gly Thr Leu Val Thr Val Ser
                100                 105                 110 tca                                                                      339
Ser <210> SEQ ID NO 86
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 86 cag gtc cag ctg gtg cag tct ggg gct gag gtg aag aag cct ggg tcc           48
Gln Val Gln Leu Val Gln Ser Gly Ala Glu Val Lys Lys Pro Gly Ser
  1               5                  10                  15 tcg gtg aag gtc tcc tgc aag act tct gga gac acc ttc agc agc tat           96
Ser Val Lys Val Ser Cys Lys Thr Ser Gly Asp Thr Phe Ser Ser Tyr
                 20                  25                  30 gct atc agc tgg gtg cga cag gcc cct gga caa ggg ctt gag tgg atg          144
Ala Ile Ser Trp Val Arg Gln Ala Pro Gly Gln Gly Leu Glu Trp Met
             35                  40                  45 gga ggg atc atc cct atc ttt ggt aga gca cac tac gca cag aag ttc          192
Gly Gly Ile Ile Pro Ile Phe Gly Arg Ala His Tyr Ala Gln Lys Phe
         50                  55                  60 cag ggc aga gtc acg att acc gcg gac gaa tcc acg agc aca gcc tac          240
Gln Gly Arg Val Thr Ile Thr Ala Asp Glu Ser Thr Ser Thr Ala Tyr
 65                  70                  75                  80 atg gag ctg agc agc ctg aga tct gag gac acg gcc gtg tat ttt tgt          288
Met Glu Leu Ser Ser Leu Arg Ser Glu Asp Thr Ala Val Tyr Phe Cys
                     85                  90                  95 gcg aga aag ttt cac ttt gtt tcg ggg agc ccc ttc ggt atg gac gtc          336
Ala Arg Lys Phe His Phe Val Ser Gly Ser Pro Phe Gly Met Asp Val
                100                 105                 110 tgg ggc caa ggg acc acg gtc acc gtc tcc tca                              369
Trp Gly Gln Gly Thr Thr Val Thr Val Ser Ser
            115                 120

<210> SEQ ID NO 87
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 87 cag gtc cag ctg gtg cag tct ggg gct gag gtg aag aag cct ggg tcc           48
Gln Val Gln Leu Val Gln Ser Gly Ala Glu Val Lys Lys Pro Gly Ser
  1               5                  10                  15 tcg gtg aag gtc tcc tgc aag act tct gga ggc acc ttc agc agc tat           96
Ser Val Lys Val Ser Cys Lys Thr Ser Gly Gly Thr Phe Ser Ser Tyr
                 20                  25                  30
```

```
gct atc agc tgg gtg cga cag gcc cct gga caa ggg ctt gag tgg atg       144
Ala Ile Ser Trp Val Arg Gln Ala Pro Gly Gln Gly Leu Glu Trp Met
        35                  40                  45 gga ggg atc atc cct atc ttt ggt aaa gca cac tac gca cag aag ttc       192
Gly Gly Ile Ile Pro Ile Phe Gly Lys Ala His Tyr Ala Gln Lys Phe
 50                  55                  60 cag ggc aga gtc acg att acc gcg gac gaa tcc acg acc aca gcc tac       240
Gln Gly Arg Val Thr Ile Thr Ala Asp Glu Ser Thr Thr Thr Ala Tyr
 65                  70                  75                  80 atg gag ctg agc agc ctg aga tct gag gac acg gcc gtg tat tac tgt       288
Met Glu Leu Ser Ser Leu Arg Ser Glu Asp Thr Ala Val Tyr Tyr Cys
                85                  90                  95 gcg aga aag tat gac tat gtt tcg ggg agc ccc ttc ggt atg gac gtc       336
Ala Arg Lys Tyr Asp Tyr Val Ser Gly Ser Pro Phe Gly Met Asp Val
            100                 105                 110 tgg ggc caa ggg acc acg gtc acc gtc tcc tca                           369
Trp Gly Gln Gly Thr Thr Val Thr Val Ser Ser
        115                 120

<210> SEQ ID NO 88
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 88 cag gtc cag ctg gtg cag tct ggg gct gag gtg aag aag cct ggg tcc        48
Gln Val Gln Leu Val Gln Ser Gly Ala Glu Val Lys Lys Pro Gly Ser
 1               5                  10                  15 tcg gtg aag gtc tcc tgc aag gct tct gga ggc acc ttc agc agc tat        96
Ser Val Lys Val Ser Cys Lys Ala Ser Gly Gly Thr Phe Ser Ser Tyr
                20                  25                  30 gct atc aac tgg gtg cga cag gcc cct gga caa ggg ctt gag tgg atg       144
Ala Ile Asn Trp Val Arg Gln Ala Pro Gly Gln Gly Leu Glu Trp Met
        35                  40                  45 gga ggg atc atc cct atc ttt ggt tca gca aac tac gca cag aag ttc       192
Gly Gly Ile Ile Pro Ile Phe Gly Ser Ala Asn Tyr Ala Gln Lys Phe
 50                  55                  60 cag gac aga gtc acg att acc gcg gac gaa tcc acg agc gca gcc tac       240
Gln Asp Arg Val Thr Ile Thr Ala Asp Glu Ser Thr Ser Ala Ala Tyr
 65                  70                  75                  80 atg gag ctg agc agc ctg aga tct gag gac acg gcc gta tat tac tgt       288
Met Glu Leu Ser Ser Leu Arg Ser Glu Asp Thr Ala Val Tyr Tyr Cys
                85                  90                  95 gcg aga gac agc agt ggc tgg tct cgg tac tat atg gac gtc tgg ggc       336
Ala Arg Asp Ser Ser Gly Trp Ser Arg Tyr Tyr Met Asp Val Trp Gly
            100                 105                 110 caa ggg acc acg gtc acc gtc tcc tca                                   363
Gln Gly Thr Thr Val Thr Val Ser Ser
        115                 120

<210> SEQ ID NO 89
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 89 cag gtc cag ctg gtg cag tct ggg gct gag gtg aag gag cct ggg tcc        48
```

```
                Gln Val Gln Leu Val Gln Ser Gly Ala Glu Val Lys Glu Pro Gly Ser
                1               5                   10                  15 tcg gtg aag gtc tcc tgc aag gct tct gga ggc acc ttc aac agc tat           96
Ser Val Lys Val Ser Cys Lys Ala Ser Gly Gly Thr Phe Asn Ser Tyr
            20                  25                  30 gct atc agc tgg gtg cga cag gcc cct gga caa ggg ctt gag tgg atg          144
Ala Ile Ser Trp Val Arg Gln Ala Pro Gly Gln Gly Leu Glu Trp Met
        35                  40                  45 gga ggg atc atc cct ctt ttc ggt ata gca cac tac gca cag aag ttc          192
Gly Gly Ile Ile Pro Leu Phe Gly Ile Ala His Tyr Ala Gln Lys Phe
    50                  55                  60 cag ggc aga gtc acg att acc gcg gac gaa tcc acg aac aca gcc tat          240
Gln Gly Arg Val Thr Ile Thr Ala Asp Glu Ser Thr Asn Thr Ala Tyr
65                  70                  75                  80 atg gac ctg agc agc ctg aga tct gag gac acg gcc gta tat tat tgt          288
Met Asp Leu Ser Ser Leu Arg Ser Glu Asp Thr Ala Val Tyr Tyr Cys
                85                  90                  95 gcg aga aag tat tcc tat gtt tcg ggg agc ccc ttc ggt atg gac gtc          336
Ala Arg Lys Tyr Ser Tyr Val Ser Gly Ser Pro Phe Gly Met Asp Val
            100                 105                 110 tgg ggc caa ggg acc acg gtc acc gtc tcc tca                              369
Trp Gly Gln Gly Thr Thr Val Thr Val Ser Ser
        115                 120

<210> SEQ ID NO 90
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 90 gaa gtg cag ttg gtg gag tct ggg gga ggc ttg gta cag cct ggc agg           48
Glu Val Gln Leu Val Glu Ser Gly Gly Gly Leu Val Gln Pro Gly Arg
1               5                   10                  15 tcc ctg aga ctc tcc tgt gca gcc tct gga atc acc ttt gat gat tat           96
Ser Leu Arg Leu Ser Cys Ala Ala Ser Gly Ile Thr Phe Asp Asp Tyr
            20                  25                  30 ggc atg cac tgg gtc cgg caa gct cca ggg aag ggc ctg gag tgg gtc          144
Gly Met His Trp Val Arg Gln Ala Pro Gly Lys Gly Leu Glu Trp Val
        35                  40                  45 tca ggt att agc tgg aat aga ggt aga ata gag tat gcg gac tct gtg          192
Ser Gly Ile Ser Trp Asn Arg Gly Arg Ile Glu Tyr Ala Asp Ser Val
    50                  55                  60 aag ggc cga ttc acc atc tcc aga gac aac gcc aag aac tcc ctg tat          240
Lys Gly Arg Phe Thr Ile Ser Arg Asp Asn Ala Lys Asn Ser Leu Tyr
65                  70                  75                  80 ctg caa atg aac agt ctg aga gct gag gac acg gcc ttg tat tac tgt          288
Leu Gln Met Asn Ser Leu Arg Ala Glu Asp Thr Ala Leu Tyr Tyr Cys
                85                  90                  95 gca aaa ggg cgg ttc cga tat ttt gac tgg ttt ctt gac tac tgg ggc          336
Ala Lys Gly Arg Phe Arg Tyr Phe Asp Trp Phe Leu Asp Tyr Trp Gly
            100                 105                 110 cag gga acc ctg gtc acc gtc tcc tca                                      363
Gln Gly Thr Leu Val Thr Val Ser Ser
        115                 120

<210> SEQ ID NO 91
<211> LENGTH: 321
<212> TYPE: DNA
<213> ORGANISM: Homo sapiens
```

<220> FEATURE:
<221> NAME/KEY: CDS
<222> LOCATION: (1)..(321)

<400> SEQUENCE: 91

```
gaa att gtg ttg aca cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
            20                  25                  30 tta gtc tgg tac caa cag aaa cct ggc cag gct ccc agg ctc ctc atc     144
Leu Val Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg cct cgg     288
Glu Asp Phe Ala Val Tyr Tyr Cys Gln Gln Arg Ser Asn Trp Pro Arg
                85                  90                  95 acg ttc ggc caa ggg acc aag gtg gaa atc aaa                         321
Thr Phe Gly Gln Gly Thr Lys Val Glu Ile Lys
                100                 105
```

<210> SEQ ID NO 92
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 92

```
gaa att gtg ttg aca cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg ccg acg     288
Glu Asp Phe Ala Val Tyr Tyr Cys Gln Gln Arg Ser Asn Trp Pro Thr
                85                  90                  95 ttc ggc caa ggg acc aag gtg gaa atc aaa                             318
Phe Gly Gln Gly Thr Lys Val Glu Ile Lys
                100                 105
```

<210> SEQ ID NO 93
<211> LENGTH: 321
<212> TYPE: DNA
<213> ORGANISM: Homo sapiens
<220> FEATURE:

<221> NAME/KEY: CDS
<222> LOCATION: (1)..(321)

<400> SEQUENCE: 93

```
gac atc cag atg acc cag tct cca tcc tca ctg tct gca tct gta gga      48
Asp Ile Gln Met Thr Gln Ser Pro Ser Ser Leu Ser Ala Ser Val Gly
1               5                   10                  15 gac aga gtc acc atc act tgt cgg gcg agt cag ggt att agc agc tgg      96
Asp Arg Val Thr Ile Thr Cys Arg Ala Ser Gln Gly Ile Ser Ser Trp
                20                  25                  30 tta gcc tgg tat cag cag aaa cca gag aaa gcc cct aag tcc ctg atc     144
Leu Ala Trp Tyr Gln Gln Lys Pro Glu Lys Ala Pro Lys Ser Leu Ile
            35                  40                  45 tat gct gca tcc agt ttg caa agt ggg gtc cca tca agg ttc agc ggc     192
Tyr Ala Ala Ser Ser Leu Gln Ser Gly Val Pro Ser Arg Phe Ser Gly
        50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
65                  70                  75                  80 gaa gat ttt gca act tat tac tgc caa cag tat aat agt tac ccg tac     288
Glu Asp Phe Ala Thr Tyr Tyr Cys Gln Gln Tyr Asn Ser Tyr Pro Tyr
                85                  90                  95 act ttt ggc cag ggg acc aag ctg gag atc aaa                         321
Thr Phe Gly Gln Gly Thr Lys Leu Glu Ile Lys
            100                 105
```

<210> SEQ ID NO 94
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 94

```
gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
                20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
            35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
        50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca ccg     288
Pro Glu Asp Phe Ala Val Tyr Tyr Cys Gln Gln Tyr Gly Ser Ser Pro
                85                  90                  95 tgg acg ttc ggc caa ggg acc aag gtg gaa atc aaa                     324
Trp Thr Phe Gly Gln Gly Thr Lys Val Glu Ile Lys
            100                 105
```

<210> SEQ ID NO 95
<211> LENGTH: 321
<212> TYPE: DNA
<213> ORGANISM: Homo sapiens
<220> FEATURE:
<221> NAME/KEY: CDS

<222> LOCATION: (1)..(321)

<400> SEQUENCE: 95

```
gac atc cag atg acc cag tct cca tcc tca ctg tct gca tct gta gga      48
Asp Ile Gln Met Thr Gln Ser Pro Ser Ser Leu Ser Ala Ser Val Gly
1               5                   10                  15 gac aga gtc acc atc act tgt cgg gcg agt cag ggt att agc agc tgg      96
Asp Arg Val Thr Ile Thr Cys Arg Ala Ser Gln Gly Ile Ser Ser Trp
            20                  25                  30 tta gcc tgg tat cag cag aaa cca gag aaa gcc cct aag tcc ctg atc     144
Leu Ala Trp Tyr Gln Gln Lys Pro Glu Lys Ala Pro Lys Ser Leu Ile
        35                  40                  45 tat gct gca tcc agt ttg caa agt ggg gtc cca tca agg ttc agc ggc     192
Tyr Ala Ala Ser Ser Leu Gln Ser Gly Val Pro Ser Arg Phe Ser Gly
    50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
65                  70                  75                  80 gaa gat ttt gca act tat tac tgc caa cag tat aat agt tac ccg tac     288
Glu Asp Phe Ala Thr Tyr Tyr Cys Gln Gln Tyr Asn Ser Tyr Pro Tyr
                85                  90                  95 act ttt ggc cag ggg acc aag ctg gag atc aaa                         321
Thr Phe Gly Gln Gly Thr Lys Leu Glu Ile Lys
            100                 105
```

<210> SEQ ID NO 96
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 96

```
gaa att gtg ttg aca cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg ccg acg     288
Glu Asp Phe Ala Val Tyr Tyr Cys Gln Gln Arg Ser Asn Trp Pro Thr
                85                  90                  95 ttc ggc caa ggg acc aag gtg gaa atc aaa                             318
Phe Gly Gln Gly Thr Lys Val Glu Ile Lys
            100                 105
```

<210> SEQ ID NO 97
<211> LENGTH: 318
<212> TYPE: DNA
<213> ORGANISM: Homo sapiens
<220> FEATURE:
<221> NAME/KEY: CDS
<222> LOCATION: (1)..(318)

```
<400> SEQUENCE: 97 gaa att gtg ttg aca cag tct cca gcc acc ctg tct ttg tct cca ggg     48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac     96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc    144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc    192
Tyr Asp Ala Ser Asn Arg Ala Thr Gly Ile Pro Ala Arg Phe Ser Gly
50                  55                  60 agt ggg tct ggg aca gac ttc act ctc acc atc agc agc cta gag cct    240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg ccg acg    288
Glu Asp Phe Ala Val Tyr Tyr Cys Gln Gln Arg Ser Asn Trp Pro Thr
                85                  90                  95 ttc ggc caa ggg acc aag gtg gaa atc aaa                            318
Phe Gly Gln Gly Thr Lys Val Glu Ile Lys
            100                 105

<210> SEQ ID NO 98
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 98 gaa att gtg ttg acg cag tct cca ggc acc ctg tct ttg tct cca ggg     48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc     96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt    192
Ile Tyr Gly Ala Ser Ser Arg Ala Thr Gly Ile Pro Asp Arg Phe Ser
50                  55                  60 ggc agt ggg tct ggg aca gac ttc act ctc acc atc agc aga ctg gag    240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca cct    288
Pro Glu Asp Phe Ala Val Tyr Tyr Cys Gln Gln Tyr Gly Ser Ser Pro
                85                  90                  95 ttc ggc gga ggg acc aag gtg gag atc aaa                            318
Phe Gly Gly Gly Thr Lys Val Glu Ile Lys
            100                 105

<210> SEQ ID NO 99
<211> LENGTH: 318
<212> TYPE: DNA
<213> ORGANISM: Homo sapiens
<220> FEATURE:
<221> NAME/KEY: CDS
<222> LOCATION: (1)..(318)
```

-continued

<400> SEQUENCE: 99

```
gaa att gtg ttg aca cag tct cca gcc acc ctg tct ttg tct cca ggg    48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac    96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc   144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc   192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct   240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg ccc acc   288
Glu Asp Phe Ala Val Tyr Tyr Cys Gln Gln Arg Ser Asn Trp Pro Thr
                85                  90                  95 ttc ggc caa ggg aca cga ctg gag att aaa                           318
Phe Gly Gln Gly Thr Arg Leu Glu Ile Lys
            100                 105
```

<210> SEQ ID NO 100
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 100

```
gcc atc cag ttg acc cag tct cca tcc tcc ctg tct gca tct gta gga    48
Ala Ile Gln Leu Thr Gln Ser Pro Ser Ser Leu Ser Ala Ser Val Gly
1               5                   10                  15 gac aga gtc acc atc act tgc cgg gca agt cag ggc att agc agt gct    96
Asp Arg Val Thr Ile Thr Cys Arg Ala Ser Gln Gly Ile Ser Ser Ala
            20                  25                  30 tta gcc tgg tat cag cag aaa cca ggg aaa gct cct aag ctc ctg atc   144
Leu Ala Trp Tyr Gln Gln Lys Pro Gly Lys Ala Pro Lys Leu Leu Ile
        35                  40                  45 tat gat gcc tcc agt ttg gaa agt ggg gtc cca tca agg ttc agc ggc   192
Tyr Asp Ala Ser Ser Leu Glu Ser Gly Val Pro Ser Arg Phe Ser Gly
    50                  55                  60 agt gga tct ggg aca gat ttc act ctc acc atc agc agc ctg cag cct   240
Ser Gly Ser Gly Thr Asp Phe Thr Leu Thr Ile Ser Ser Leu Gln Pro
65                  70                  75                  80 gaa gat ttt gca act tat tac tgt caa cag ttt aat agt tac cca ttc   288
Glu Asp Phe Ala Thr Tyr Tyr Cys Gln Gln Phe Asn Ser Tyr Pro Phe
                85                  90                  95 act ttc ggc cct ggg acc aaa gtg gat atc aaa                       321
Thr Phe Gly Pro Gly Thr Lys Val Asp Ile Lys
            100                 105
```

<210> SEQ ID NO 101
<211> LENGTH: 98
<212> TYPE: PRT
<213> ORGANISM: Homo sapiens

<400> SEQUENCE: 101

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 102
<211> LENGTH: 98
<212> TYPE: PRT
<213> ORGANISM: Homo sapiens

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 103
<211> LENGTH: 98
<212> TYPE: PRT
<213> ORGANISM: Homo sapiens

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 104
<211> LENGTH: 97
<212> TYPE: PRT
<213> ORGANISM: Homo sapiens
```

<400> SEQUENCE: 104

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala

<210> SEQ ID NO 105
<211> LENGTH: 95
<212> TYPE: PRT
<213> ORGANISM: Homo sapiens

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 106
<211> LENGTH: 95
<212> TYPE: PRT
<213> ORGANISM: Homo sapiens

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 107
<211> LENGTH: 96
<212> TYPE: PRT

<213> ORGANISM: Homo sapiens

<400> SEQUENCE: 107

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 108
<211> LENGTH: 95
<212> TYPE: PRT
<213> ORGANISM: Homo sapiens

<400> SEQUENCE: 108

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95

<210> SEQ ID NO 109
<211> LENGTH: 107
<212> TYPE: PRT
<213> ORGANISM: Homo sapiens

<400> SEQUENCE: 109

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys
                100                 105

<210> SEQ ID NO 110

```
<211> LENGTH: 16
<212> TYPE: PRT
<213> ORGANISM: Homo sapiens

<400> SEQUENCE: 110

Tyr Gly Met Asp Val Trp Gly Gln Gly Thr Thr Val Thr Val Ser Ser
1               5                   10                  15

<210> SEQ ID NO 111
<211> LENGTH: 14
<212> TYPE: PRT
<213> ORGANISM: Homo sapiens

<400> SEQUENCE: 111

Phe Asp Tyr Trp Gly Gln Gly Thr Leu Val Thr Val Ser Ser
1               5                   10

<210> SEQ ID NO 112
<211> LENGTH: 16
<212> TYPE: PRT
<213> ORGANISM: Homo sapiens

<400> SEQUENCE: 112

Tyr Tyr Met Asp Val Trp Gly Gln Gly Thr Thr Val Thr Val Ser Ser
1               5                   10                  15

<210> SEQ ID NO 113
<211> LENGTH: 13
<212> TYPE: PRT
<213> ORGANISM: Homo sapiens

<400> SEQUENCE: 113

Asp Tyr Trp Gly Gln Gly Thr Leu Val Thr Val Ser Ser
1               5                   10

<210> SEQ ID NO 114
<211> LENGTH: 12
<212> TYPE: PRT
<213> ORGANISM: Homo sapiens

<400> SEQUENCE: 114

Trp Thr Phe Gly Gln Gly Thr Lys Val Glu Ile Lys
1               5                   10

<210> SEQ ID NO 115
<211> LENGTH: 11
<212> TYPE: PRT
<213> ORGANISM: Homo sapiens

<400> SEQUENCE: 115

Thr Phe Gly Gln Gly Thr Lys Val Glu Ile Lys
1               5                   10

<210> SEQ ID NO 116
<211> LENGTH: 12
<212> TYPE: PRT
<213> ORGANISM: Homo sapiens

<400> SEQUENCE: 116

Tyr Thr Phe Gly Gln Gly Thr Lys Leu Glu Ile Lys
1               5                   10

<210> SEQ ID NO 117
<211> LENGTH: 10
<212> TYPE: PRT
```

```
<213> ORGANISM: Homo sapiens

<400> SEQUENCE: 117

Phe Gly Gly Gly Thr Lys Val Glu Ile Lys
1               5                   10

<210> SEQ ID NO 118
<211> LENGTH: 11
<212> TYPE: PRT
<213> ORGANISM: Homo sapiens

<400> SEQUENCE: 118

Thr Phe Gly Gly Gly Thr Lys Val Glu Ile Lys
1               5                   10

<210> SEQ ID NO 119
<211> LENGTH: 11
<212> TYPE: PRT
<213> ORGANISM: Homo sapiens

<400> SEQUENCE: 119

Thr Phe Gly Gln Gly Thr Arg Leu Glu Ile Lys
1               5                   10

<210> SEQ ID NO 120
<211> LENGTH: 12
<212> TYPE: PRT
<213> ORGANISM: Homo sapiens

<400> SEQUENCE: 120

Phe Thr Phe Gly Pro Gly Thr Lys Val Asp Ile Lys
1               5                   10
```

UNITED STATES PATENT AND TRADEMARK OFFICE
CERTIFICATE OF CORRECTION

| | |
|---|---|
| PATENT NO. | : 9,580,507 B2 |
| APPLICATION NO. | : 15/188860 |
| DATED | : February 28, 2017 |
| INVENTOR(S) | : Korman et al. |

It is certified that error appears in the above-identified patent and that said Letters Patent is hereby corrected as shown below:

In the Claims

In Claim 7, at Column 144, Line 4, please replace "set forth in SEQ ID NO 14" with --set forth in SEQ ID NO: 14--.

In Claim 30, at Column 150, Line 20, please replace "The kit of claim A," with --The kit of claim 29,--.

Signed and Sealed this
Twenty-third Day of May, 2017

Michelle K. Lee
*Director of the United States Patent and Trademark Office*